US011591415B2

(12) United States Patent
Wood et al.

(10) Patent No.: US 11,591,415 B2
(45) Date of Patent: Feb. 28, 2023

(54) COMPOSITIONS AND METHODS FOR DIFFERENTIAL RELEASE OF 1-METHYLCYCLOPROPENE

(71) Applicant: Verdant Technologies, LLC, Saint Paul, MN (US)

(72) Inventors: Willard E. Wood, Arden Hills, MN (US); Joseph Frank Sarageno, Jr., New Richmond, WI (US); Joseph S. Keute, East Bethel, MN (US); Amanda Lundgren, Hudson, WI (US)

(73) Assignee: Verdant Technologies, LLC, Saint Paul, MN (US)

( * ) Notice: Subject to any disclaimer, the term of this patent is extended or adjusted under 35 U.S.C. 154(b) by 0 days.

(21) Appl. No.: 16/863,629

(22) Filed: Apr. 30, 2020

(65) Prior Publication Data

US 2021/0332158 A1 Oct. 28, 2021

Related U.S. Application Data

(63) Continuation of application No. 16/859,399, filed on Apr. 27, 2020.

(51) Int. Cl.
*C08B 37/00* (2006.01)
*C07C 7/148* (2006.01)
(Continued)

(52) U.S. Cl.
CPC ............ *C08B 37/0015* (2013.01); *A01N 3/00* (2013.01); *A01N 25/22* (2013.01); *A01N 27/00* (2013.01);
(Continued)

(58) Field of Classification Search
CPC ............................ C08B 37/0015; C07C 7/148
See application file for complete search history.

(56) References Cited

U.S. PATENT DOCUMENTS 3,940,667 A 2/1976 Pearce
3,943,103 A 3/1976 Borden et al.
(Continued)

FOREIGN PATENT DOCUMENTS

CN 109527081 A 3/2019
EP 250871 A1 1/1988
(Continued)

OTHER PUBLICATIONS

Collaborative International Pesticides Analytical Council (CIPAC) Information Sheet No. 767 (2009).
(Continued)

*Primary Examiner* — Youngsul Jeong
(74) *Attorney, Agent, or Firm* — Kagan Binder, PLLC

(57) ABSTRACT

A clathrate of 1-methylcyclopropene with α-cyclodextrin, obtained as a solid particulate product, is modified by comminuting, classifying, or both to obtain a modified particulate. When subjected to identical atmospheric disgorgement conditions of humidity and temperature, identical masses of the modified and unmodified particulates exhibit different rates of 1-methylcyclopropene disgorgement. Specifically, we have found that a smaller mean particle size is inversely related to a greater rate of 1-methylcyclopropene release.

15 Claims, 6 Drawing Sheets

(51) Int. Cl.

| | | |
|---|---|---|
| *A01N 3/00* | (2006.01) | |
| *C08B 37/16* | (2006.01) | |
| *A01N 25/22* | (2006.01) | |
| *A01N 27/00* | (2006.01) | |
| *C07C 13/04* | (2006.01) | |
| *A23B 7/152* | (2006.01) | |
| *A23B 7/154* | (2006.01) | |
| *A23B 7/159* | (2006.01) | |
| *C09D 11/17* | (2014.01) | |
| *A01N 25/34* | (2006.01) | |

(52) U.S. Cl.
CPC .............. *A23B 7/152* (2013.01); *A23B 7/154* (2013.01); *A23B 7/159* (2013.01); *C07C 7/148* (2013.01); *C07C 13/04* (2013.01); *C08B 37/0012* (2013.01); *C09D 11/17* (2013.01); *A01N 25/34* (2013.01); *A23V 2002/00* (2013.01); *C07C 2601/02* (2017.05)

(56) References Cited

U.S. PATENT DOCUMENTS

| | | | |
|---|---|---|---|
| 4,181,752 A | | 1/1980 | Martens et al. |
| 5,619,324 A | * | 4/1997 | Harvill ............... G01N 15/0211 356/336 |
| 5,658,968 A | | 8/1997 | Catena et al. |
| 6,017,849 A | | 1/2000 | Daly et al. |
| 6,232,365 B1 | | 5/2001 | Weiss et al. |
| 6,271,127 B1 | | 8/2001 | Liu et al. |
| 6,313,068 B1 | | 11/2001 | Daly et al. |
| 6,358,670 B1 | | 3/2002 | Wong et al. |
| 6,444,619 B1 | * | 9/2002 | Kostansek ............. A01N 27/00 504/357 |
| 6,548,448 B2 | | 4/2003 | Kostansek |
| 6,599,673 B2 | | 7/2003 | Kumar et al. |
| 7,569,160 B2 | | 8/2009 | Oldenzijl et al. |
| 7,799,885 B2 | | 9/2010 | Shustack et al. |
| 7,842,746 B2 | | 11/2010 | Bloom et al. |
| 8,414,989 B2 | | 4/2013 | Wood et al. |
| 8,580,140 B2 | | 11/2013 | Jacobson et al. |
| 9,320,288 B2 | | 4/2016 | Wood et al. |
| 9,381,163 B2 | | 7/2016 | Loo et al. |
| 9,421,793 B2 | * | 8/2016 | Wood ...................... B32B 3/10 |
| 2011/0143004 A1 | | 6/2011 | Wood et al. |
| 2012/0107459 A1 | | 5/2012 | Wood et al. |
| 2014/0080710 A1 | | 3/2014 | Zhang et al. |
| 2014/0080712 A1 | | 3/2014 | Lao et al. |
| 2016/0095311 A1 | | 4/2016 | Lu et al. |
| 2016/0130198 A1 | | 5/2016 | Mir |

FOREIGN PATENT DOCUMENTS

| | | |
|---|---|---|
| EP | 1593306 A2 | 11/2005 |
| KR | 20160010460 | 1/2016 |
| WO | 2008/089140 A1 | 7/2008 |
| WO | 2014040288 | 3/2014 |

OTHER PUBLICATIONS

Neoh, T.L. et al., "Dissociation characteristic of the inclusion complex of cyclomaltohexaose (α-cyclodextrin) with 1-methylcyclopropene in response to stepwise rising relative humidity", Carbohydrate Research, vol. 345, No. 14 (2010) pp. 2085-2089.
Neoh, T.L. et al., "Kinetic Study of Thermally Stimulated Dissociation of Inclusion Complex of 1-Methylcyclopropene with α-Cyclodextrin by Thermal Analysis", J. Phys. Chem. B2008, vol. 112, No. 49 (2008) pp. 15914-15920.
Neoh, T.L. et al., "Kinetics of Molecular Encapsulation of 1-Methylcyclopropene into α-Cyclodextrin", J. Agric. Food Chem. vol. 55, No. 26 (2007) pp. 11020-11026.
Weiss et al., "Pulsed Electron Beam Polymerization", posted Jan. 1, 2006 (http://www.adhesivesmag.com/Articles/Feature_Article/47965fdd41bc8010VgnVCM100000f932a8c0___).
Collaborative International Pesticides Analytical Council (CIPAC) Information Sheet No. 282 (2009).
ASTM D96-88(1998), Standard Test Methods for Water and Sediment in Crude Oil by Centrifuge Method (Field Procedure) (Withdrawn 2000), ASTM International, West Conshohocken, PA, 1998, www.astm.org.
ASTM D7334-08(2013), Standard Practice for Surface Wettability of Coatings, Substrates and Pigments by Advancing Contact Angle Measurement, ASTM International, West Conshohocken, PA, 2013, www.astm.org.
Dodziuk, Helena, "Cyclodextrins and Their Complexes: Chemistry, Analytical Methods, Applications", pp. 162-170, 2006.
Sjeizli, Jozsef, "Cyclodextrin Technology", Kluwer Academic Publishers, pp. 6,7,154,155,1988.
International Search Report mailed in International Application No. PCT/US2021/029148, dated Oct. 18, 2021, 11 pages.
Written Opinion mailed in International Application No. PCT/US2021/029148, dated Oct. 18, 2021, 36 pages.
Choi et al "Facile Fabrication of Core-in-Shell Particles by the Slow Removal of the Core and Its Use in the Encapsulation of Metal Nanoparticles", Langmuir, 2008, 24(9), pp. 4633-4636.
Chen Xi: "Development of liquid 1-methylcyclopropene delivery formulations for modifying ethylene response of fresh produce", 2015, pp. 1-4, 23-104.
International Searching Authority, "International Search Report", issued in connection with international patent application No. PCT/US2021/029133 dated Jul. 19, 2021, 7 pages.
International Searching Authority, "Written Opinion", issued in connection with international patent application No. PCT/US2021/029133 dated Jul. 19, 2021, 13 pages.

* cited by examiner

COMPOSITIONS AND METHODS FOR DIFFERENTIAL RELEASE OF 1-METHYLCYCLOPROPENE

CROSS-REFERENCE TO RELATED APPLICATIONS

This application is a continuation application of U.S. patent application Ser. No. 16/859,399 entitled "COMPOSITIONS AND METHODS FOR DIFFERENTIAL RELEASE OF 1-METHYLCYCLOPROPENE", which is incorporated by reference herein the entirety and for all purposes.

BACKGROUND

Exposure of living plant tissues to 1-methylcyclopropene (1-MCP) is known to slow or even halt ripening or senescence thereof 1-MCP is an ethylene antagonist and a gas at common ambient temperatures (boiling point reported as 4.7° C.). The gas can become affixed within ethylene receptors on the surface of a living plant or a portion thereof (collectively, "living plant materials"), effectively blocking ethylene insertion while failing to trigger the biological response of senescence. For this reason, 1-MCP is useful as an anti-senescence treatment for post-harvest preservation of ethylene-responsive fresh vegetables and fruits, capable of slowing or even halting senescence during storage and transportation.

Daly et. al., U.S. Pat. Nos. 6,017,849 and 6,313,068 teach a clathrate of 1-methylcyclopropene with α-cyclodextrin with ("1-MCP/c/CD" or "1-MCP clathrate"). The 1-MCP gas complexes readily with α-cyclodextrin to form a crystalline solid that is easily collected as a powder. The crystalline character of the clathrate may be confirmed, for example, by x-ray diffraction analysis. The clathrate is disrupted by dissolution in liquid water, wherein disgorgement of 1-MCP from the clathrate is achieved by dissolving the 1-MCP clathrate in a large amount of liquid water situated within a large volume containment, for example a silo, truck bed, warehouse, or another such storage facility where 1-MCP gas can be contained together with the living plant materials in order to achieve the anti-senescence treatment.

In addition to dissolution in liquid water, contacting the clathrate with sufficient water vapor and/or elevated temperatures also leads to disgorgement of 1-MCP from the clathrate. Neoh, T. L. et al., *Carbohydrate Research* 345 (2010) 2085-2089; and Neoh, T. L. et al., *J. Phys. Chem. B* 2008, 112, 15914-15920 showed that humidity and heat respectively bring about release of 1-MCP from the 1-MCP clathrate. And Kostansek, U.S. Pat. No. 6,548,448, showed that 1-MCP clathrate within a pouch formed of polyvinyl-alcohol or low-density polyethylene, and sealed by edge-melting will release 1-MCP when the pouch is placed in a high-humidity environment.

Wood et al. teach in various embodiments that 1-MCP/c/CD may be blended with a carrier material and subsequently coated or printed on a substrate, using conditions targeting avoidance of 1-MCP disgorgement. The coated substrate is then positioned proximal to living plant material, where the humidity of biological respiration causes 1-MCP disgorgement. The coated substrates may be configured near, within, or integral to a packaging material or container, such as sheet wrapping, cartons, punnets, and the like where living plant tissue is packaged or will be packaged. The water vapor proximal to the coated substrate, such as that provided naturally by respiration of the living plant material, initiates the anti-senescence treatment.

Thus, for example, Wood et al., U.S. Pat. No. 8,414,989 and related counterparts, which are incorporated by reference herein for all purposes, teach that liquid α,β-unsaturated monomers and blends of such monomers are suitable carriers for a 1-MCP clathrate, wherein the liquid monomers are mixed with the 1-MCP clathrate, then the mixture is coated or printed followed by irradiating with electromagnetic irradiation. No 1-MCP disgorgement is observed during the mixing, coating, or curing.

Wood et al., U.S. Pat. No. 9,320,288 and related counterparts, which are incorporated by reference herein for all purposes, teach that low-melting waxes such as petrolatum and similar materials are a suitable carriers for the 1-MCP clathrate, obtaining viscosities of e.g. 30 cP or less at 80° C. to meet the requirements for flexographic printing, and can be cooled to "set up" or solidify once printed, without curing. After printing, the printed substrate is covered with a second layer to provide a laminate construction. The second layer may be the same substrate as the first layer, or it may be different; for example, the second layer may be a polymer coated and/or cured on top of the printed surface.

Even further, Wood et al., U.S. Pat. No. 9,421,793 and related counterparts, incorporated by reference herein for all purposes, teach that electrostatically printable particles—that is, toner particles—are suitable carriers for electrostatically printing and affixing an image containing the 1-MCP clathrate on a substrate, wherein the clathrate is mixed with or applied to an electrostatically printable particle which functions as the carrier. Electrostatic printing of individualized 1-MCP clathrate-bearing package inserts or labels, for example based on weight, are enabled by conventional "toner cartridge" delivery.

According to the foregoing teachings, when 1-MCP/c/CD particulate embedded within a coated or printed carrier is located proximal to living plant materials, diffusion of gaseous water vapor through the substrate/coating is sufficient to disrupt the clathrate, disgorging 1-MCP gas which then diffuses back into the atmosphere proximal to the living plant material where it can interact with an ethylene receptor. In each of these product formats, rate of 1-MCP disgorgement is differentiated by changing the physicochemical characteristics of the carrier and/or substrate, or by selection of product constructions such as laminated coatings and the like, or some combination of these approaches. Release of 1-MCP from the coatings depends not only on temperature and humidity, but also on the rate of diffusion of water vapor into the coating and the rate of 1-MCP diffusion from the coating/substrate—properties inherent to the coating/substrate and not the clathrate itself.

Controlling the rate of disgorgement of 1-MCP from 1-MCP clathrate embedded in a coating therefore depends not only on ambient atmospheric conditions, but also on diffusion of sufficient water vapor into the coating to disgorge 1-MCP from the embedded 1-MCP clathrate; and further still on the rate of diffusion of the disgorged 1-MCP from the coating to reach the living plant material.

It would be highly desirable to provide differential rate of 1-MCP disgorgement from a 1-MCP clathrate, without the need to use a carrier or to obtain a coating having the 1-MCP clathrate incorporated therein. It would be highly desirable to provide differential rate of 1-MCP disgorgement from a 1-MCP clathrate itself, without the need to use a carrier or to obtain a coating having the 1-MCP clathrate incorporated in the coating. It would be highly desirable to provide coatings having a 1-MCP clathrate incorporated therein, further wherein differential rate of 1-MCP disgorgement from a 1-MCP clathrate does not require reformulating the carrier, changing substrates, changing product configuration, or any combination of these.

It would be desirable from both the technical and manufacturing viewpoints to provide products capable of releasing 1-MCP at variable rates without the need to change the substrate or reformulate the carrier employed to coat or print the 1-MCP/c/CD clathrate.

SUMMARY OF THE INVENTION

Described herein are methods, uses, and compositions related to modifying the rate of disgorgement of 1-MCP from a 1-MCP/c/CD clathrate. The 1-MCP clathrate, obtained as a solid particulate product, is modified to obtain a modified particulate. When subjected to identical atmospheric conditions, further wherein the atmospheric conditions are disgorgement conditions of humidity, temperature, pressure, identical masses of the modified and unmodified particulates exhibit different rates of 1-MCP disgorgement. Specifically, we have found that a smaller mean particle size is inversely related to a greater rate of 1-MCP release.

Thus, in first through fourth embodiments described herein, a 1-MCP/c/CD particulate is modified by classifying, comminuting, or both comminuting and classifying to provide a modified particulate. First through fourth embodiments further includes blends of two or more modified particulates, and blends of one or more modified particulate with an unmodified particulate. The modified particulates of first through fourth embodiments are further suitably enclosed in a pouch, forming modified particulate pouches of fifth embodiments. The modified particulates of first through fourth embodiments are further suitably affixed to a substrate by coating a mixture of particulates and a carrier on a substrate, forming coated substrates of sixth embodiments herein. The modified particulates of first through fourth embodiments, the modified particulate pouches of fifth embodiments, or the coated substrates of sixth embodiments are subjected to disgorgement conditions in seventh embodiments herein.

In first embodiments, the modifying comprises, consists essentially of, or consists of classifying. Classifying means separating a particulate product into two or more portions having different mean particle sizes, different median particle sizes, or different particle size distributions. In such first embodiments, a method comprises, consists essentially of, or consists of classifying a particulate product to form two or more classified particulate portions. Some suitable methods of classifying include sieving or filtration, gravitational separation, fluidized bed separation, and combinations of these.

Further in first embodiments, a modified particulate composition comprises, consists essentially of, or consists of a classified particulate, wherein the classified particulate is a first classified particulate portion, a second classified particulate portion, or optionally a third or a higher order classified particulate portion, further wherein each of the classified particulate portions is one portion of a particulate product physically separated from the remainder thereof.

In second embodiments, the modifying comprises, consists essentially of, or consists of comminuting. Comminuting means physically reducing a particle size of a particulate product to form a comminuted particulate. Some suitable methods of comminuting include grinding, fluidized bed milling, jet milling, ultrasonic milling, ball milling, hammer milling, cryogenic milling, and combinations of these.

Further in second embodiments, the modified particulate comprises, consists essentially of, or consists of a comminuted particulate. In such second embodiments, the particulate product and the comminuted particulate have one or more of: different mean particle sizes, different median particle sizes, and different particle size dispersity.

In third embodiments, the modifying comprises, consists essentially of, or consists of comminuting followed by classifying. In third embodiments, a method comprises, consists essentially of, or consists of comminuting a particulate product to form a comminuted particulate, followed by classifying the comminuted particulate to form two or more comminuted classified particulates. In some third embodiments, the comminuting and the classifying are accomplished in a single process. In other such third embodiments, the comminuting and the classifying are accomplished contemporaneously. In embodiments the method further includes subjecting a comminuted classified particulate to disgorgement conditions.

Further in third embodiments, the modified particulate comprises, consists essentially of, or consists of a comminuted classified particulate. The comminuted classified particulate is a first comminuted classified particulate portion, a second comminuted classified particulate portion, or optionally a third or a higher order comminuted classified particulate portion, wherein each of the classified particulate portions is one portion of a particulate product physically separated from the remainder thereof.

In fourth embodiments, a method comprises, consists essentially of, or consists of mixing two or more modified particulates, or mixing one or more modified particulates with a particulate product to form a combined modified particulate. In embodiments the method further includes subjecting a combined modified particulate to disgorgement conditions.

Further in fourth embodiments, the modified particulate comprises, consists essentially of, or consists of a combined modified particulate. The combined modified particulate comprises, consists essentially of, or consists of an admixture of two or more modified particulates, or an admixture of one or more modified particulates with a particulate product. The combined modified particulate comprises a selected weight ratio of two or more modified particulates, or of one or more modified particulates with a particulate product (unmodified particulate). The weight ratio of the two or more modified particulates, or of the one or more modified particulates with a particulate product present in the combined modified particulate is not limited, and is selected by an operator to achieve a targeted rate of 1-MCP disgorgement when the combined modified particulate is subjected to disgorgement conditions. In some fourth embodiments, by way of example, about 1 to 1000 parts by weight of a first modified particulate is admixed with about 1 to 1000 parts by weight of a second modified particulate to form a combined modified particulate; in another example, about 1 to 1000 parts by weight of a modified particulate is admixed with 1 to 1000 parts by weight of an unmodified particulate to form a combined modified particulate.

In fifth embodiments, a modified particulate according to one of the first through fourth embodiments above is incorporated within a pouch (also called an envelope or sachet) to form a modified particulate pouch. The modified particulate pouch of fifth embodiments comprises, consists essentially of, or consists of a pouch comprising an interior volume sealed to prevent the free exchange of the interior volume with atmospheric air; and a modified particulate disposed within the interior volume, further wherein the pouch is permeable to water vapor and to 1-MCP gas. In fifth embodiments, the pouch comprises a thermoplastic sheet or film permeable to water vapor and to 1-MCP gas.

Thus, in fifth embodiments, a method includes forming a modified particulate pouch by enclosing a modified particulate of one of the first through fourth embodiments above within the interior volume of a pouch. Such methods may include contacting a modified particulate with a thermoplastic sheet or film, the thermoplastic sheet or film permeable to water vapor and to 1-MCP gas; and configuring the thermoplastic sheet or film to form an interior volume surrounding the modified particulate, further wherein the interior volume is excluded from the free exchange with atmospheric air. Methods of configuring are not particularly limited by may include one or more of cutting, folding, crimping, heat bonding or heat sealing, stapling, and stitching.

In sixth embodiments, a method comprises, consists essentially of, or consists of mixing a carrier with a modified particulate of any of the first through fourth embodiments to form a coating composition; coating the coating composition on a surface of a substrate; and affixing the coated composition to the substrate to provide a coated substrate. In some sixth embodiments, the coating composition further includes one or more non-aqueous solvents. In sixth embodiments, the coating composition includes less than 5 wt % of water based on the weight of the coating composition; in some embodiments the coating composition includes 2 wt % of water or less based on the weight of the coating composition. In some sixth embodiments one or more of the mixing, coating, or affixing is accomplished in a continuous process; in some such embodiments, the coating, and affixing are accomplished serially in a continuous process; in still other such embodiments mixing, coating, and affixing are accomplished serially in a continuous process.

In sixth embodiments, the carrier comprises, consists essentially of, or consists of: a polymer carrier, a polymerizable carrier, a wax carrier, or an electrostatically printable particulate carrier. The polymer carrier comprises, consists essentially of, or consists of one or more polymers, that is, one or more compounds having two or more repeating units. In embodiments the coating composition comprising the polymer carrier further comprises one or more non-aqueous solvents. The polymerizable carrier comprises, consists essentially of, or consists of one or more α,β-unsaturated monomers that are liquids within a temperature range of 0° C. to 50° C. at atmospheric pressure and are capable of polymerization when irradiated with electromagnetic radiation. The wax carrier comprises, consists essentially of, or consists of one or more waxes. In some such embodiments, the wax carrier comprises, consists essentially of, or consists of a petrolatum or a petrolatum-like material. The electrostatically printable particulate carrier comprises, consists essentially of, or consists of an electrostatically printable particulate.

Additionally, combinations of the foregoing carriers or individual components thereof are suitably mixed to form a coating composition. Non-limiting examples of such coating composition mixtures include a polymerizable carrier mixed with a wax or a polymer; a wax carrier mixed with a non-aqueous solvent; and the like without limitation. Coating compositions as defined herein include any such coating composition mixtures without limit. In some sixth embodiments, the coating composition comprises less than 5 wt % of water based on the weight of the coating composition.

In sixth embodiments, mixing the carrier with a modified particulate to form a coating composition is accomplished by one more methods comprising, consisting essentially of, or consisting of static mixing and mechanical mixing such as stirring, or a combination thereof. In some such embodiments, mixing the carrier with the modified particulate to form a coating composition is accomplished at a temperature at or below about 80° C. Where a coating composition includes more than two components, order of mixing the components is not limited except as required by the coating composition components and their interactions. For example, it may be advantageous to mix a polymer with a non-aqueous solvent prior to mixing the modified particulate with the polymer/solvent combination, in order to fully disperse or dissolve the polymer in the solvent prior to mixing the modified particulate with the polymer/solvent combination.

In sixth embodiments, a coating composition comprises, consists essentially of, or consists of a carrier and a modified particulate of any of first through fourth embodiments. In sixth embodiments, the coating composition comprises about 5 wt % or less of water based on the weight of the coating composition. In some sixth embodiments, the coating composition further includes a non-aqueous solvent. The amount of the modified particulate in the coating composition is selected by the user without limitation; in some industrially useful embodiments, the coating composition comprises, consists essentially of, or consists of about 0.01 wt % to about 50 wt % of the modified particulate based on the weight of the coating composition.

In some sixth embodiments, the substrate comprises, consists essentially of, or consists of a thermoplastic sheet or film, or a woven or nonwoven fabric or paper. The substrate is defined by having at least one surface that is substantially planar and coatable using one or more industrially useful methods of coating selected from die coating, slot coating, brush coating, spray coating, flood coating, curtain coating, screen printing, inkjet printing, gravure or reverse gravure coating, flexographic printing, or electrostatic printing.

In sixth embodiments, the coating composition is coated on a substrate surface using one or more methods well known to those of skill in the coating and/or printing industry, further wherein specific coating methodology is determined by the physicochemical properties of the carrier. Coating the coating composition is carried out at a temperature at or below about 80° C. Coating methods suitably employed to coat the coating compositions include but are not limited to die coating, slot coating, brush coating, spray coating, flood coating, screen printing, fluidized bed coating, inkjet printing, gravure or reverse gravure coating, flexographic printing, electrostatic printing, and the like. Coating is continuous coating, which is coating of all or substantially all of a coatable substrate surface with the coating composition; or discontinuous coating, which is coating only a selected portion of the coatable substrate surface with the coating composition.

In sixth embodiments, affixing the coating composition on the substrate surface is accomplished using one or more methods well known to those of skill in the coating and/or printing industry, further wherein specific affixing methodology is determined by the physicochemical properties of the carrier. In some such embodiments, affixing is carried out at a temperature at or below about 80° C. Affixing methods suitably employed to affix the coating compositions to the substrate surface include evaporating (drying), irradiating, cooling, and applying heat and pressure. In sixth embodiments where the carrier includes a polymer and a non-aqueous solvent, affixing comprises or consists of evaporating the solvent from the coated composition. In sixth embodiments where the carrier includes one or more α,β-unsaturated monomers, affixing comprises or consists of irradiating the coated composition with electromagnetic radiation. In sixth embodiments where the carrier includes a wax, affixing may include cooling the coated composition and in some embodiments additionally laminating the coated composition. In sixth embodiments where the carrier is an electrostatically printable particulate, affixing mean applying heat and pressure to the coated composition.

Accordingly, in sixth embodiments, affixing the coating composition to the substrate results in a coated substrate. The coated substrates of sixth embodiments comprise, consist essentially of, or consist of a substrate having a coating affixed to at least a portion of a surface thereof, wherein the coating comprises, consists essentially of, or consists of a carrier and a modified particulate. The coating thickness and coating weight of the coating are selected by the user in accord with one or more commercially useful embodiments, further in accord with the physicochemical properties of the carrier and the weight percent of modified particulate in the carrier. In some sixth embodiments, the coating thickness is between 0.1 micron and 50 microns on all or a portion of the coated substrate surface. In some sixth embodiments, the coating obtains a coating weight of between 0.1 and 100 g/m$^2$.

Seventh embodiments are methods of disgorging 1-MCP from the modified particulate of first through fourth embodiments, the modified particulate pouches of fifth embodiments, or the coated substrates of sixth embodiments by subjecting the modified particulate of first through sixth embodiments to disgorgement conditions.

Disgorgement conditions refer to the atmospheric conditions of ambient pressure (about 1 atm), temperature between 0° C. and about 50° C., and relative humidity of about 80% to 100%. Disgorgement conditions of the modified particulates of first through fourth embodiments, pouches of fifth embodiments, and coated substrates of sixth embodiments are the same as disgorgement conditions for the (unmodified) particulate products previously reported in the art, including pouches and substrates having coatings comprising unmodified particulate products. When subjected to identical disgorgement conditions of humidity, temperature, and pressure, the modified and unmodified particulates exhibit different rates of 1-MCP disgorgement. When subjected to identical disgorgement conditions of humidity, temperature, and pressure, pouches or coated substrates comprising a modified particulate exhibit different rates of 1-MCP disgorgement from pouches or coated substrates comprising the unmodified particulate.

While further presence of liquid water proximal to or even in contact with the modified particulates of first through fourth embodiments, pouches of fifth embodiments, and coated substrates of sixth embodiments is not excluded in the methods of the seventh embodiment, it is not necessary to include or use liquid water to obtain disgorgement of 1-MCP.

In some seventh embodiments, a portion of the water vapor contacting the modified particulates of first through fourth embodiments, pouches of fifth embodiments, or coated substrates of sixth embodiments is supplied by biological respiration of a living plant or portion thereof, wherein the living plant or portion thereof is situated proximal to the modified particulates of first through fourth embodiments, pouches of fifth embodiments, or coated substrates of sixth embodiments.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
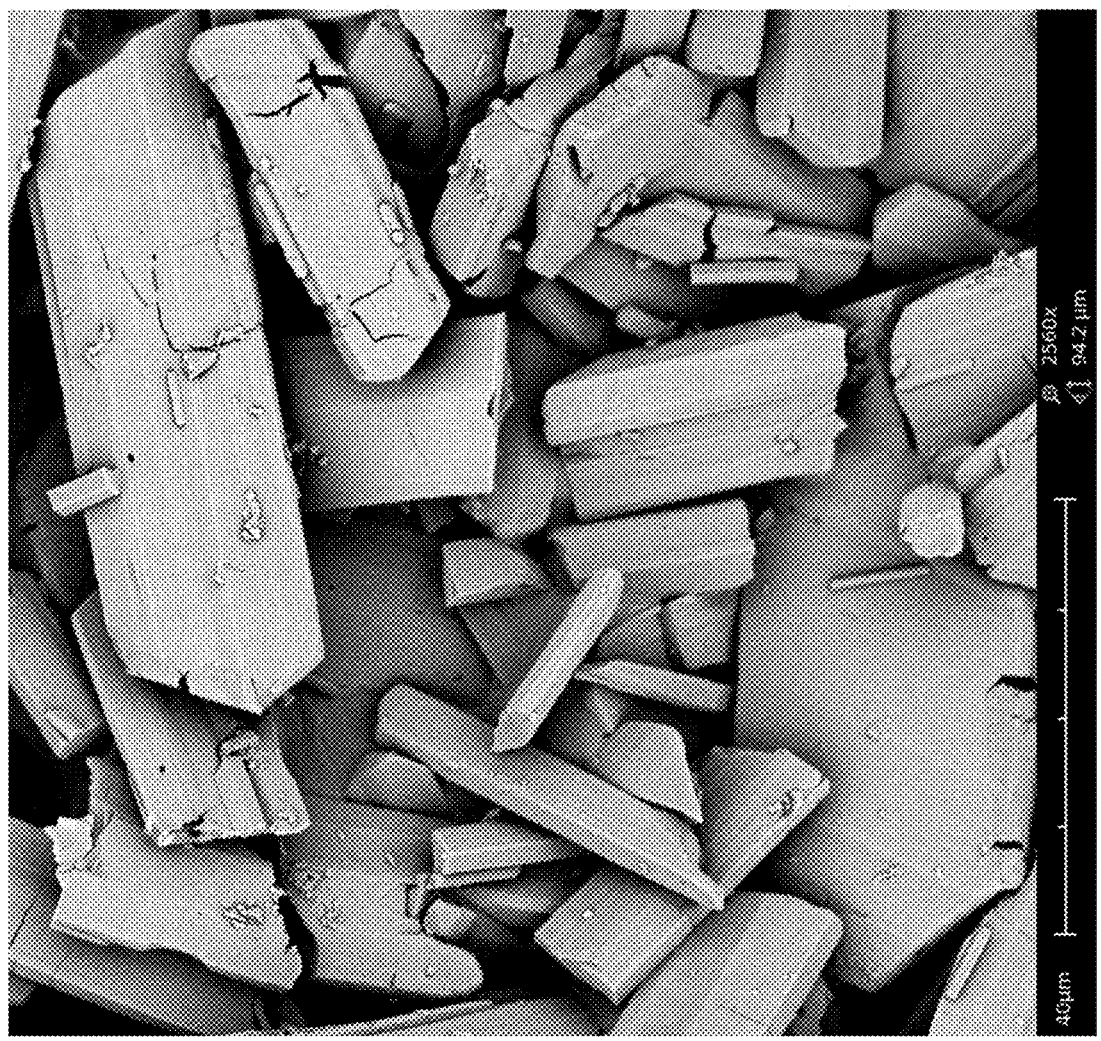
FIG. 1 is a micrographic image of an unmodified particulate as described herein.

Although the present disclosure provides references to preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein, "particulate" refers to a discrete group or mass of particles characterized by a particle size of 1000 microns or less.

As used herein, "particle size" refers to an average particle size, a median particle size, a mean particle size, or a particle size dispersity of a particulate, as specified or determined by context and further as such particle sizes are determined by a method of particle size analysis known by those of ordinary skill in the art of analyzing particles having dimensions of 1000 microns or less. Such methods include light scattering analysis and Coulter counter methods, for example. Unless specified otherwise, "particle size" generally refers to a volume-based average or method of measuring a volume-based average assuming spherical particles. When comparing two or more particulates, differences in median particle sizes and/or other particle size parameters are determined based on the respective individually determined median particle sizes and/or other specified parameters.

As used herein, "modified particulate" means a classified particulate, a comminuted particulate, a comminuted classified particulate, or a combined modified particulate. The unmodified source particulate from which the modified particulate is derived may be referred to herein as the "unmodified particulate" or the "particulate product" or other similar terms.

As used herein, the terms "classify", "classified", "classification" and like terms refer to physically separating a particulate into two or more portions that differ according to a particle size; and to the particulate portions that result from the separating. Classifying a particulate results in at least two classified particulate portions, wherein each classified particulate portion is characterized as having a different average particle size, mean particle size, or median particle size.

As used herein, "comminute", "comminuting" and like terms refer to methods of reducing an average particle size of a particulate by mechanical methods such as grinding, milling, and the like.

As used herein, the term "substrate" means a solid article having at least one surface capable of receiving a coating composition. Substrates are not particularly limited as to makeup, shape, or regarding parameters such as size or thickness. In embodiments, the substrate is a thermoplastic sheet or film or a woven or nonwoven fabric or paper. In embodiments, the substrate is disposed in a "web" format, that is, characterized by top and bottom major surfaces defining a thickness between the major surfaces of about 10 microns to 1000 microns.

As used herein, the term "container" means a containment defining an interior volume and sealed to exclude the free exchange of the interior volume with atmospheric air.

As used herein, a "pouch" is a containment that is permeable to water vapor and to 1-methylcyclopropene (1-MCP) gas.

As used herein, "permeable" as related to 1-methylcyclopropene gas indicates 1-MCP permeability of equal to or greater than 0.01 (cm$^3$·mm/m$^2$ 0.24 hrs·bar) at standard temperature and pressure (STP) and 0% relative humidity; and as related to water vapor indicates permeability of equal to or greater than 0.1 (g·mm/m$^2$·24 hr) at 38° C. and 90% relative humidity, when measured according to ASTM D96. "Permeability" or "permeable" may refer to water vapor, 1-MCP, or both as determined by context.

As used herein, the term "disgorgement conditions" refers to atmospheric conditions proximal to a particulate. Such conditions include ambient pressure (typically about 1 atm), temperature between 0° C. and about 50° C., and relative humidity between about 80% and 100%.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the term "substantially" means "consisting essentially of", as that term is construed in U.S. patent law, and includes "consisting of" as that term is construed in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Discussion

In any of the embodiments described herein, a particulate is suitably characterized by mean particle size, median particle size, mode size, specific surface area, diameter on cumulative, and one or more other such particle size parameters as suitably determined using analytical methods familiar to those of skill in measuring particle sizes in the range of 1 nm to 1000 μm. For purposes of consistency herein, references below to particle size generally, as well as more specific references to mean particle size, collectively refer to mean particle size as measured by laser light analysis, such as by using a HORIBA LA-950 Laser Particle Size Analyzer, available from Horiba Scientific, unless otherwise specified or determined by context.

In any of the embodiments described herein, a "particulate product" means, refers to, or indicates a crystalline particulate form of the clathrate of 1-methylcyclopropene with α-cyclodextrin, as received, for example from AgroFresh Inc. of Philadelphia, Pa.; or as obtained from contacting α-cyclodextrin with 1-methylcyclopropene gas according to a procedure outlined in one or more of the following: U.S. Pat. Nos. 8,580,140; 6,548,448; 6,017,849; and Neoh, T. Z. et al., *J. Agric. Food Chem.* 2007, 55, 11020-11026. Such particulate products are also referred to as "unmodified particulate" in embodiments below for context.

In any of the embodiments herein, an particulate product obtained in accordance with the foregoing known methods is characterized by a mean particle size between 30 μm and 100 μm, for example between 40 μm and 70 μm or between 40 μm and 50 μm, a diameter on cumulative d10 ranging from about 5 μm to about 20 μm, a diameter on cumulative d50 ranging from about 30 μm to about 60 μm, a diameter on cumulative d90 ranging from about 60 μm to about 150 μm, or two or more thereof. Particles having one or more dimensions of 300 μm to 500 μm have been observed by microscopic analysis of particulate products generated by one of the known methods disclosed above.

The particulate products are further characterized as having a substantially dry powder form, that is sufficiently dry and free of impurities that the does not disgorge 1-MCP when the particulate product is enclosed in a sealed container that is impermeable to water vapor, further wherein the temperature of the particulate product is maintained below 90° C., preferably 80° C. or below, and more preferably 50° C. or below. Such particulate products consist of or consist essentially of the clathrate of 1-methylcyclopropene with α-cyclodextrin. A particulate product consisting essentially of the clathrate also includes free α-cyclodextrin in an amount of up to about 15 wt % of the particulate product; and less than 1 ppm by weight of chlorinated impurities, which are 1-chloromethylpropene and 3-chloromethylpropene.

Particulate products having the properties above are crystalline, and as synthesized obtain a mean particle size between 30 μm and 100 μm, often between 40 μm and 70 μm.

The particulate product includes an amount of 1-MCP trapped within the crystalline clathrate wherein at least 85 wt % of the particulate product is 1-MCP clathrate and not α-cyclodextrin—that is, "empty" cyclodextrin. The quantity of 1-MCP in any particulate product or modified particulate described herein is suitably determined using the gas chromatographic method described in Collaborative International Pesticides Analytical Council (CIPAC) Information Sheet Number 282.

FIG. 1 is a scanning electron micrograph of a representative particulate product. The particulate product of FIG. 1 has a mean particle size of 46.2 μm, d10 11.1 μm, d50 40.2 μm, and d90 88.9 μm as determined by laser light scattering analysis (HORIBA LA-950 Laser Particle Size Analyzer, available from Horiba Scientific of Edison, N.J.).

In first through fourth embodiments described herein, a particulate product as described above is modified by comminuting, classifying, or both comminuting and classifying; and in some embodiments further mixing portions of particulates to provide a modified particulate. In fifth embodiments described herein, a modified particulate of any one of first through fourth embodiments is enclosed in a pouch. In sixth embodiments described herein, a modified particulate of any one of first through fourth embodiments is incorporated into a coating composition which is coated on a substrate to obtain a coated substrate.

In seventh embodiments described herein, a modified particulate of any one of first through fourth embodiments, a pouch of any of fifth embodiments, or a coated substrate of any of sixth embodiments is subjected to disgorgement conditions. When subjected to identical disgorgement conditions, a modified particulate of first, second, third, or fourth embodiments disgorges 1-MCP at a modified rate—that is, a different rate—when compared to the same mass of the unmodified particulate. Thus, under identical disgorgement conditions, identical masses of 1-MCP/c/α-cyclodextrin clathrate particulates release 1-MCP gas at different rates, depending on particle size of the clathrate particulate.

Further, we have determined that the relative rate of disgorgement of 1-MCP from a modified particulate under disgorgement conditions is inversely related to the mean particle size of the modified particulate. Thus, decreasing the mean particle size of a 1-MCP/c/α-cyclodextrin clathrate particulate causes the rate of 1-MCP disgorgement to increase under identical disgorgement conditions. Further, in fifth embodiments, the foregoing finding applies to the modified particulates of first through fourth embodiments enclosed in a pouch that is permeable to water vapor and to 1-MCP. Still further, in sixth embodiments, the foregoing finding applies to the modified particulates of first through fourth embodiments when entrained (embedded, dispersed) in a coating affixed to a substrate.

First Embodiments

In first embodiments a particulate product is modified by classifying. Thus, in first embodiments, modifying comprises, consists essentially of, or consists of classifying. In such first embodiments, a method comprises, consists essentially of, or consists of classifying a particulate product to form one or more classified particulate portions. Some suitable methods of classifying include sieving, gravitational sedimentation or separation, fluidized bed separation including countercurrent flow separation, and combinations of these methods. In some embodiments the classifying includes applying a force, such as a central force (e.g. cyclonic or centrifugal methods); while in other embodiments only gravitational force is applied (that is, 1 g). In embodiments an applied force is 1.1 g to 10 g.

In embodiments, a first classified particulate portion is selected to have a mean particle size that is different from the mean particle size of the unmodified particulate product. In some embodiments, second, third, or higher classified particulate portions are selected from a single particulate product, wherein each of the classified particulate portions have a modified mean particle size, which means a particle size that is different from the mean particle size of the unmodified particulate product.

The classifying is carried out in the absence of liquid water and under conditions of temperature and humidity that avoid disgorgement of 1-MCP. Such conditions include but are not limited to temperatures of less than 90° C., preferably less than 80° C.; and relative humidity of 50% or less. In embodiments, one of skill may determine whether classifying results in disgorgement of 1-MCP by quantifying the amount of 1-MCP in the particulate product and the classifying product using the procedure outlined in Collaborative International Pesticides Analytical Council (CIPAC) Information Sheet Number 282, and comparing the amount of 1-MCP in each of the particulates. We have found that classifying a 1-MCP clathrate particulate in accordance with the methods disclosed herein does not lead to measurable loss of 1-MCP therefrom. Accordingly, modified particulates of first embodiments have the same, or substantially the same amount of 1-MCP as the particulate product. Stated differently, the methods of first embodiments do not lead to loss of 1-MCP gas from a 1-MCP clathrate of α-cyclodextrin.

In some first embodiments, a classified particulate is characterized as having a mean particle size that differs by at least 20% from the mean particle size of the unmodified particulate. In some first embodiments, a classified particulate is characterized as having a mean particle size that is at least 20% and up to 200% greater the mean particle size of the unmodified particulate, for example 20% to 100% greater, or 20% to 50% greater, or 50% to 100% greater, or 50% to 200% greater, or 100% to 200% greater than the mean particle size of the unmodified particulate. In some first embodiments, a classified particulate is characterized as having a mean particle size that is at least 20% lower and up to 99.9% lower than the mean particle size of the unmodified particulate, for example 20% to 95% lower, or 20% to 90% lower, or 20% to 80% lower, or 20% to 70% lower, or 20% to 60% lower, or 20% to 50% lower, or 50% to 99.9% lower, or 50% to 95% lower, or 50% to 90% lower, or 50% to 80% lower, or 50% to 70% lower, or 70% to 99.9% lower, or 70% to 95% lower, or 70% to 90% lower than the mean particle size of the unmodified particulate. In embodiments, one or more classified particulate portions are selected to have a specific mean particle size; such specific mean particle size is about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, 30 μm to 35 μm, 35 μm to 40 μm, 40 μm to 45 μm, 45 μm to 50 μm, 50 μm to 55 μm, 55 μm to 60 μm, 60 μm to 65 μm, 65 μm to 70 μm, 70 μm to 75 μm, 75 μm to 80 μm, 80 μm to 85 μm, 85 μm to 90 μm, 90 μm to 95 μm, 95 μm to 100 μm, or even greater than 100 μm. In embodiments, one or more classified particulate portions are selected to have a mean particle size targeted in a range between 1 μm and 3 μm, between 2 μm and 4 μm, between 3 μm and 5 μm, between 4 μm and 6 μm, between 5 μm and 7 μm, between 6 μm and 8 μm, between 7 μm and 9 μm, between 8 μm and 10 μm, between 9 μm and 11 μm, between 10 μm and 12 μm, between 11 μm and 13 μm, between 12 μm and 14 μm, or between 13 μm and 15 μm; or between 1 μm and 5 μm, between 5 μm and 10 μm, between 10 μm and 15 μm, or between 15 μm and 20 μm; or between 1 μm and 10 μm, between 2 μm and 15 μm, between 2 μm and 10 μm, between 3 μm and 15 μm, between 3 μm and 14 μm, between 3 μm and 13 μm, between 3 μm and 12 μm, between 3 μm and 11 μm, between 3 μm and 10 μm, between 3 μm and 9 μm, between 3 μm and 8 μm, between 3 μm and 7 μm, or between 10 μm and 20 μm.

To further illustrate the foregoing, in a nonlimiting example of first embodiments herein, a particulate product is obtained from a supplier and characterized as having a mean particle size of 50 μm, diameter on cumulative d10 of 20 μm, diameter on cumulative d50 of 40 μm, and diameter on cumulative d90 of 100 μm. Further in the representative example, the particulate product is classified using gravitational separation to obtain first, second, and third classified particulate portions. The first classified particulate portion is characterized as having a mean particle size of 5 μm, diameter on cumulative d10 of 2 μm, diameter on cumulative d50 of 4 μm, and diameter on cumulative d90 of 8 μm; the second classified particulate portion is characterized as having a mean particle size of 10 μm, diameter on cumulative d10 of 5 μm, diameter on cumulative d50 of 15 μm, and diameter on cumulative d90 of 20 μm; and the third classified particulate is characterized as having a mean particle size of 80 μm, diameter on cumulative d10 of 50 μm, diameter on cumulative d50 of 90 μm, and diameter on cumulative d90 of 110 μm. Further in the foregoing representative embodiment, the unmodified (source) particulate and the first, second, and third classified particulate portions selected therefrom are subjected to identical disgorgement conditions of 1 atm, 20° C., 95% relative humidity, whereupon first and second classified particulate portions disgorge 1-MCP faster than the unmodified particulate and the third classified particulate portion disgorges 1-MCP at a slower rate than the unmodified particulate.

Other methods of classifying the particulate products, and additional representative examples will be readily apparent to one of skill in the art of classifying particulates. In embodiments, any such methods are limited by excluding the addition of liquid water and excluding conditions wherein temperature exceeds 90° C., more preferably excluding conditions wherein temperature exceeds about 80° C. Such limitations are necessary to avoid causing disgorgement of 1-MCP during the classifying.

Second Embodiments

In second embodiments a particulate product is modified by comminuting. Comminuting means reducing a particle size of a particulate product using mechanical methodology. Thus, in second embodiments, modifying a particulate product comprises, consists essentially of, or consists of comminuting the particulate product. Further in second embodiments, a modified particulate comprises, consists essentially of, or consists of a comminuted particulate. The comminuted particulate is characterized as having a mean particle size that is less than the mean particle size of the unmodified particulate. In second embodiments, a comminuted particulate is characterized as having a mean particle size that is at least 20% less, and as much as 99.9% less than the mean particle size of the unmodified particulate, for example 25% to 99.9% less, or 30% to 99.9% less, or 35% to 99.9% less, or 40% to 99.9% less, or 45% to 99.9% less, or 50% to 99.9% less, or 55% to 99.9% less, or 60% to 99.9% less, or 65% to 99.9% less, or 70% to 99.9% less, or 75% to 99.9% less, or 80% to 99.9% less, or 85% to 99.9% less, or 90% to 99.9% less, or 95% to 99.9% less, or 96% to 99.9% less, or 97% to 99.9% less, or 98% to 99.9% less, or 99% to 99.9% less than the mean particle size of the unmodified particulate.

Some suitable methods of comminuting include grinding, fluidized bed milling, jet milling, ultrasonic milling, sand milling, bead milling, ball milling, hammer milling, cryogenic milling, and combinations of these. The comminuting is carried out in the absence of liquid water and under conditions of temperature and humidity that avoid disgorgement of 1-MCP. Such conditions include but are not limited to temperatures of less than 90° C., preferably less than 80° C.; and relative humidity of 50% or less. In embodiments, one of skill may determine whether comminuting results in disgorgement of 1-MCP by quantifying the amount of 1-MCP in the particulate product and the comminuted product using the procedure outlined in Collaborative International Pesticides Analytical Council (CIPAC) Information Sheet Number 282, and comparing the amount of 1-MCP in each of the particulates. We have found that one of skill comminuting a 1-MCP clathrate particulate in accordance with the methods disclosed herein may easily avoid measurable loss of 1-MCP therefrom. Accordingly, modified particulates of second embodiments have the same, or substantially the same amount of 1-MCP as the particulate product. Stated differently, the methods of second embodiments do not lead to loss of 1-MCP gas from a 1-MCP clathrate of α-cyclodextrin.

In a representative but nonlimiting example of second embodiments herein, a particulate product is synthesized according to the methods described in U.S. Pat. No. 8,580,140 and the synthesized product is characterized as having a mean particle size of 50 μm, diameter on cumulative d10 of 20 μm, diameter on cumulative d50 of 40 μm, and diameter on cumulative d90 of 100 μm. Further in the representative example, the particulate product (unmodified particulate) is comminuted by jet milling to obtain a comminuted particulate characterized as having a mean particle size of 10 μm (that is, an 80% reduction in particle size), diameter on cumulative d10 of 5 μm, diameter on cumulative d50 of 15 μm, and diameter on cumulative d90 of 20 μm.

Other methods of comminuting the particulate products, and additional representative examples will be readily apparent to one of skill in the art of comminuting particulates having dimensions of 1000 microns or less.

Third Embodiments

In third embodiments, the modifying comprises, consists essentially of, or consists of comminuting as described in second embodiments above, followed by classifying as described in first embodiments above. In third embodiments, a method comprises, consists essentially of, or consists of comminuting a particulate product to form a comminuted particulate, followed by classifying the comminuted particulate to form two or more comminuted classified particulate portions. In some third embodiments, comminuting is accomplished separately from classifying, in which one or more comminuted particulates are classified serially or batchwise. In other third embodiments, the comminuting and the classifying are accomplished in a single step or process, by comminuting while also collecting particulates having a desired particle size range as they are formed, while allowing larger particulates to be retained for further comminuting. In some such third embodiments, the comminuting is jet milling and the classifying is sieving (filtration type method).

Thus, in third embodiments, a modified particulate comprises, consists essentially of, or consists of a comminuted classified particulate. The comminuted classified particulate is a first comminuted classified particulate portion, a second comminuted classified particulate portion, or optionally a third or a higher order comminuted classified particulate portion.

In embodiments, a first comminuted classified particulate portion is selected to have a mean particle size that is different from the mean particle size of the comminuted particulate. In some embodiments, second, third, or higher comminuted classified particulate portions are selected from a single comminuted particulate, wherein each of the comminuted classified particulate portions have a mean particle size that is different from the mean particle size of the comminuted particulate.

In some third embodiments, any one comminuted classified particulate portion may be referred to in context as a comminuted classified particulate. Thus, in third embodiments, a comminuted classified particulate is characterized as having a mean particle size that differs by at least 20% from the mean particle size of the unmodified particulate. In some third embodiments, a comminuted classified particulate is characterized as having a mean particle size that is at least 20% and up to 200% greater the mean particle size of the unmodified particulate, for example 20% to 100% greater, or 20% to 50% greater, or 50% to 100% greater, or 50% to 200% greater, or 100% to 200% greater than the mean particle size of the unmodified particulate. In some third embodiments, a comminuted classified particulate is characterized as having a mean particle size that is at least 20% lower and up to 99.9% lower than the mean particle size of the unmodified particulate, for example 20% to 95% lower, or 20% to 90% lower, or 20% to 80% lower, or 20% to 70% lower, or 20% to 60% lower, or 20% to 50% lower, or 50% to 99.9% lower, or 50% to 95% lower, or 50% to 90% lower, or 50% to 80% lower, or 50% to 70% lower, or 70% to 99.9% lower, or 70% to 95% lower, or 70% to 90% lower than the mean particle size of the unmodified particulate.

In embodiments, a comminuted classified particulate is selected to have a specific mean particle size. Such specific mean particle size is about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, or about 30 μm. In embodiments, a comminuted classified particulate is selected to have a mean particle size targeted in a range between 1 μm and 3 μm, between 2 μm and 4 μm, between 3 μm and 5 μm, between 4 μm and 6 μm, between 5 μm and 7 μm, between 6 μm and 8 μm, between 7 μm and 9 μm, between 8 μm and 10 μm, between 9 μm and 11 μm, between 10 μm and 12 μm, between 11 μm and 13 μm, between 12 μm and 14 μm, or between 13 μm and 15 μm; or between 1 μm and 5 μm, between 5 μm and 10 μm, between 10 μm and 15 μm, or between 15 μm and 20 μm; or between 1 μm and 10 μm, between 2 μm and 15 μm, between 2 μm and 10 μm, between 3 μm and 15 μm, between 3 μm and 14 μm, between 3 μm and 13 μm, between 3 μm and 12 μm, between 3 μm and 11 μm, between 3 μm and 10 μm, between 3 μm and 9 μm, between 3 μm and 8 μm, between 3 μm and 7 μm, or between 10 μm and 20 μm.

The comminuting and classifying methods of third embodiments are carried out in the absence of liquid water and under conditions of temperature and humidity that avoid disgorgement of 1-MCP. Such conditions include but are not limited to those described for classifying in accordance with first embodiments and comminuting in accordance with second embodiments. We have found that one of skill comminuting and classifying a 1-MCP clathrate particulate in accordance with the methods disclosed herein may easily avoid measurable loss of 1-MCP therefrom. Accordingly, modified particulates of third embodiments have the same, or substantially the same amount of 1-MCP as the particulate product. Stated differently, the methods of third embodiments do not lead to loss of 1-MCP gas from a 1-MCP clathrate of α-cyclodextrin.

Fourth Embodiments

In fourth embodiments, a method comprises, consists essentially of, or consists of mixing two or more of the modified particulates of any of first through third embodiments, or mixing one or more modified particulates with an unmodified particulate to form a combined modified particulate. Thus, in fourth embodiments, the modified particulate comprises, consists essentially of, or consists of a combined modified particulate. The combined modified particulate comprises, consists essentially of, or consists of an admixture of two or more modified particulates of first through third embodiments above, or an admixture of one or more modified particulates of first through third embodiments above with an unmodified particulate.

The combined modified particulate is characterized by the mass ratio of the two or more modified particulates of the first through third embodiments, or of one or more modified particulates with an unmodified particulate. The weight ratio of the two or more modified particulates, or of the one or more modified particulates with a particulate product present in the combined modified particulate is not limited, and is selected by an operator freely and without limitation to achieve a targeted rate of 1-MCP disgorgement under disgorgement conditions.

In some fourth embodiments, by way of example, about 1 part by weight of a first modified particulate is admixed with about 1 to 1000 parts by weight of a second modified particulate to form a combined modified particulate; in another example, about 1 to 1000 parts by weight of a modified particulate is admixed with 1 to 1000 parts by weight of an unmodified particulate to form a combined modified particulate. Such combinations are made freely and without limitation. In some embodiments, 1 part by weight of a first modified particulate is admixed with 1 part, 2 parts, 3 parts, 4 parts, 5 parts, 6 parts, 7 parts, 8 parts, 9 parts, 10 parts, 15 parts, 20 parts, 25 parts, 30 parts, 35 parts, 40 parts, 45 parts, 50 parts, 55 parts, 60 parts, 65 parts, 70 parts, 75 parts, 80 parts, 85 parts, 90 parts, 95 parts, 100 parts, 200 parts, 300 parts, 400 parts, 500 parts, 600 parts, 700 parts, 800 parts, 900 parts, or 1000 parts of a second modified particulate to form a combined modified particulate. In some embodiments, 1 part by weight of an unmodified particulate is admixed with 1 part, 2 parts, 3 parts, 4 parts, 5 parts, 6 parts, 7 parts, 8 parts, 9 parts, 10 parts, 15 parts, 20 parts, 25 parts, 30 parts, 35 parts, 40 parts, 45 parts, 50 parts, 55 parts, 60 parts, 65 parts, 70 parts, 75 parts, 80 parts, 85 parts, 90 parts, 95 parts, 100 parts, 200 parts, 300 parts, 400 parts, 500 parts, 600 parts, 700 parts, 800 parts, 900 parts, or 1000 parts of a modified particulate to form a combined modified particulate. In some embodiments, 1 part by weight of a modified particulate is admixed with 1 part, 2 parts, 3 parts, 4 parts, 5 parts, 6 parts, 7 parts, 8 parts, 9 parts, 10 parts, 15 parts, 20 parts, 25 parts, 30 parts, 35 parts, 40 parts, 45 parts, 50 parts, 55 parts, 60 parts, 65 parts, 70 parts, 75 parts, 80 parts, 85 parts, 90 parts, 95 parts, 100 parts, 200 parts, 300 parts, 400 parts, 500 parts, 600 parts, 700 parts, 800 parts, 900 parts, or 1000 parts of an unmodified particulate to form a combined modified particulate.

The combined modified particulate is admixed in the absence of liquid water and under conditions of temperature and humidity that avoid disgorgement of 1-MCP. Such conditions include but are not limited to those described as suitable in first, second, or third embodiments above. Admixing the combined modified particulates is accomplished using conditions that do not lead to loss of 1-MCP gas from a 1-MCP clathrate of α-cyclodextrin. Accordingly, the modified particulates of fourth embodiments include the same, or substantially the same amount of 1-MCP as the particulate product. Stated differently, the methods of fourth embodiments do not lead to loss of 1-MCP gas from a 1-MCP clathrate of α-cyclodextrin.

We have found that the combined modified particulates of fourth embodiments are characterized by a rate of 1-MCP disgorgement that is related to the mass ratio of the combined particulates. Thus, in a representative but nonlimiting example of fourth embodiments herein, a particulate product is obtained from a supplier and characterized as having a mean particle size of 50 µm. A portion of the particulate product (unmodified particulate) is set aside, and the rest is comminuted by jet milling to obtain a comminuted particulate characterized as having a mean particle size of 10 µm. Then 1 g of the comminuted particulate is admixed with 1 g of the unmodified particulate to form a combined modified particulate. Then 0.05 g of the comminuted particulate, 0.05 g of the unmodified particulate, and 0.05 g of the combined modified particulate are separately subjected to identical disgorgement conditions. The release rate of 1-MCP from the comminuted particulate is faster than that of the combined modified particulate; and the release rate of 1-MCP from the combined modified particulate is faster than that of the unmodified particulate.

Fifth Embodiments

In fifth embodiments, a modified particulate according to one of the first through fourth embodiments above is incorporated within a pouch (also called an envelope or sachet) to form a modified particulate pouch. The modified particulate pouch of fifth embodiments comprises, consists essentially of, or consists of a pouch comprising an interior volume sealed to prevent the free exchange of the interior volume with atmospheric air; and a modified particulate disposed within the interior volume, further wherein the pouch is permeable to water vapor and to 1-MCP gas. In some fifth embodiments, the pouch comprises a thermoplastic sheet or film permeable to water vapor and to 1-MCP gas.

In fifth embodiments herein, the permeable thermoplastic sheet or film is characterized as having 1-MCP permeability of equal to or greater than 0.01 ($cm^3 \cdot mm/m^2 \cdot 24$ hrs·bar) at standard temperature and pressure (STP) and 0% relative humidity; and water vapor permeability of equal to or greater than 0.1 ($g \cdot mm/m^2 \cdot 24$ hr) at 38° C. and 90% relative humidity when measured according to ASTM D96. In fifth embodiments, the modified particulate pouch suitably isolates the modified particulate from direct contact with a living plant material while still allowing for placement of the pouch proximal to the living plant material. Since the thermoplastic surrounding the modified particulate is permeable to water vapor and to 1-MCP, a modified particulate pouch placed proximal to living plant material obtains disgorgement of 1-MCP therefrom to treat the living plant material.

Thus, in fifth embodiments, a method includes forming a modified particulate pouch by enclosing a modified particulate of one of the first through fourth embodiments above within the interior volume of a pouch. In such embodiments suitable methods include selecting a mass of a modified particulate; contacting the mass of modified particulate with a thermoplastic sheet or film, the thermoplastic sheet or film permeable to water vapor and to 1-MCP gas; and configuring the thermoplastic sheet or film to form a pouch defining an interior volume surrounding the selected mass of modified particulate, wherein the interior volume is excluded from the free exchange with atmospheric air.

The amount of modified particulate in the modified particulate pouch is selected to target a type of living plant material and mass of the living plant material to be treated by disgorgement of 1-MCP from the modified particulate. Living plant material to be treated can include, for example, a single living plant portion (e.g. a head of broccoli or lettuce) packaged for consumer use; a carton or stack of cartons including living plant material within each carton (such as cartons of mangoes or broccoli harvested in the field); or a truck bed, silo, or warehouse including dozens, hundreds, even thousands of individual living plants or plant portions.

Thermoplastic sheets and films useful in fifth embodiments are characterized as permeable to water and to 1-MCP in accord with defined permeabilities herein. Suitable thermoplastic sheets and films include commercially available "web" format sheet or film articles characterized as having two major surfaces defining a thickness therebetween of about 10 µm to 1 mm, such as 25 µm to 1 mm, or 50 µm to 1 mm, or 75 µm to 1 mm, or 100 µm to 1 mm, or 125 µm to 1 mm, or 150 µm to 1 mm, or 200 µm to 1 mm, or 250 µm to 1 mm, or 500 µm to 1 mm, or 10 µm to 800 µm, or 10 µm to 500 µm, or 10 µm to 400 µm, or 10 µm to 300 µm, or 10 µm to 200 µm, or 10 µm to 100 µm, or 50 µm to 300 µm, or 50 µm to 200 µm, or 50 µm to 150 µm.

Suitable thermoplastics useful for making the pouches include films and sheets formed from polymeric compounds including but not limited to polyvinyl halides such as poly(vinyl chloride) (plasticized and unplasticized) and copolymers thereof; polyvinylidene halides such as polyvinylidene chloride and copolymers thereof; polyolefins such as polyethylene, polypropylene, copolymers thereof, and morphological variations thereof including LLDPE, LDPE, HDPE, UHMWPE, metallocene polymerized polypropylene, and the like; polyesters such as polyethylene terephthalate (PET) or polylactic acid (PLA) and plasticized variations thereof; polystyrene and copolymers thereof including HIPS; polyvinyl alcohol and copolymers thereof; copolymers of ethylene and vinyl acetate; and the like. Blends, alloys, composites, crosslinked versions of the foregoing, and recycled versions thereof are also useful in various embodiments. A thermoplastic film or sheet may be processed by orienting the film or sheet, such as by biaxially orienting the film or sheet. Thermoplastic coated nonwovens such as paper or cardboard extrusion coated with one of the foregoing thermoplastics are also useful in forming the pouches of fifth embodiments. Two or more layers of such thermoplastics are present in some embodiments as multilayer films or sheets.

The dimensions of the major surfaces of the thermoplastic sheets and films useful in fifth embodiments are not particularly limited and may be selected from "sheets" which generally refer to major surface dimensions of 1 meter or less in any direction; and "films" which generally refer to roll type formats wherein the major surfaces are characterized by a width of about 2 cm to 2 m and a length of 10 m to 1 km or even more. Films and sheets are suitably subjected to one or more of die cutting, blade cutting, laser cutting, slicing, stamping, embossing, and the like as necessary to provide a suitable shape and configuration of the thermoplastic film or sheet for pouch formation.

The pouches of fifth embodiments are made in the absence of liquid water and under conditions of temperature and humidity that avoid disgorgement of 1-MCP. Such conditions include but are not limited to temperatures of less than 90° C., preferably less than 80° C.; and relative humidity of 50% or less. Accordingly, the modified particulates disposed within the interior volume of the pouches of fifth embodiments have the same, or substantially the same amount of 1-MCP as the particulate product. Stated differently, the methods of fifth embodiments do not lead to loss of 1-MCP gas from the modified particulate.

Methods of configuring the pouch are not particularly otherwise limited and may include one or more of cutting, folding, crimping, heat bonding or heat sealing, stapling, and stitching and other related methods of configuring thermoplastic materials to form pouch or envelope type containers sealed from the free exchange with the surrounding atmosphere. In some such embodiments, configuring includes but is not limited to folding and heat sealing the edges of the thermoplastic sheet or film to surround a selected mass of modified particulate to form a modified particulate pouch. In some such embodiments, configuring includes disposing a selected mass of modified particulate between two thermoplastic sheets or films, and heat sealing a perimeter around the modified particulate to form a modified particulate pouch.

In embodiments, the mass of modified particulate selected for disposition within a pouch or for enclosing within a pouch is selected by one of skill in determining the amount of 1-MCP needed for treatment of a living plant material, further as limited in practicality by e.g. available equipment and/or thermoplastic sheet or film format for obtaining a desired pouch size, configuration, or format. Any amount of a modified particulate may be selected by an operator in conjunction with the interior volume of the pouch. In some commercially useful embodiments, 1 g or less of a modified particulate is selected for disposition within a pouch, such as 0.001 g to 1.000 g, or 0.001 g to 0.900 g, or 0.001 g to 0.800 g, or 0.001 g to 0.700 g, or 0.001 g to 0.600 g, or 0.001 g to 0.500 g, or 0.001 g to 0.400 g, or 0.001 g to 0.300 g, or 0.001 g to 0.200 g, or 0.001 g to 0.100 g, or 0.001 g to 0.090 g, or 0.001 g to 0.080 g, or 0.001 g to 0.070 g, or 0.001 g to 0.060 g, or 0.001 g to 0.050 g, or 0.001 g to 0.040 g, or 0.001 g to 0.030 g, or 0.001 g to 0.020 g, or 0.001 g to 0.010 g, or 0.001 g to 0.005 g.

In embodiments, one or more inactive powders are further included in the pouch, the inactive powder(s) being unreactive with the modified particulates and useful as fillers. Such inactive powders include saccharides and polysaccharides such as dextrins, celluloses, starches, and the like.

Pouches having a set mass of modified particulate per pouch may be continuously manufactured using conventional methodology. Further, individual pouches with different masses of modified particulates may also be manufactured at the discretion of an operator depending on commercial demand and ability to configure manufacturing equipment to desired specifications. End use may include use of a single pouch; or multiple pouches may be deployed serially or contemporaneously as selected by the user to obtain customized treatment for a living plant material targeted for 1-MCP treatment.

Sixth Embodiments

In sixth embodiments, a method comprises, consists essentially of, or consists of mixing a carrier with a modified particulate of any of the first through fourth embodiments to form a coating composition; coating the coating composition on a surface of a substrate; and affixing the coated composition to the substrate to provide a coated substrate. In some sixth embodiments, the coating composition further includes one or more non-aqueous solvents. In sixth embodiments, the coating composition includes 5 wt % of water or less based on the weight of the coating composition, and in some such embodiments 2 wt % of water or less based on the weight of the coating composition. In some sixth embodiments one or more of the mixing, coating, or affixing is accomplished in a continuous process; in some such embodiments, the coating, and affixing are accomplished serially in a continuous process; in still other such embodiments mixing, coating, and affixing are accomplished serially in a continuous process. In sixth embodiments, a coated substrate comprises, consists essentially of, or consists of a substrate having a coated composition affixed to a surface thereof.

In sixth embodiments, the mixing, coating, and affixing are limited by the need to avoid disgorgement of 1-MCP. Accordingly, in all methodologies of sixth embodiments, liquid water is substantially excluded from the modified particulates or the coating compositions; and liquid water is substantially excluded from all methodologies of sixth embodiments. "Substantially excluded" herein recognizes that a coating composition may include up to 5 wt % water content, particularly since cyclodextrin itself, present as part of the clathrate in the modified particulate, naturally associates with water in its crystalline form and this water will be brought into any coating composition employed in sixth embodiments. In the event that a coating composition is found to include more than 5 wt % water, the composition, individual components thereof, or any mixture of the components may be dried to remove water using conventional methods such as zeolite adsorption, oven drying, and the like as determined by the specific material to be dried. Further in all methodologies of sixth embodiments, temperature proximal to the modified particulate should not exceed 90° C. and preferably should be about 80° C. or less.

The coating methods of sixth embodiments are carried out in the absence of liquid water and under conditions of temperature and humidity that avoid disgorgement of 1-MCP. Such conditions include but are not limited to temperatures of less than 90° C., preferably less than 80° C.; and relative humidity of 50% or less. In embodiments, one of skill may quantify the amount of 1-MCP in a modified particulate present in a coating composition using a modified version of the procedure outlined in Collaborative International Pesticides Analytical Council (CIPAC) Information Sheet Number 282, wherein the modification is measuring a coating composition or a coated substrate instead of the modified particulate itself and comparing the amount of 1-MCP in the particulate product to the amount of 1-MCP in the modified particulate present within the coating composition or the coated substrate. Such methods of quantifying 1-MCP present in a coating composition are demonstrated in one or more examples in the sections below. We have found that one of skill coating in accordance with the methods disclosed in sixth embodiments herein may easily avoid measurable loss of 1-MCP therefrom. Accordingly, the modified particulates present in the coating compositions and the coated substrates of sixth embodiments have the same, or substantially the same amount of 1-MCP as the particulate product. Stated differently, the methods of sixth embodiments do not lead to loss of 1-MCP gas from a 1-MCP clathrate of α-cyclodextrin.

In sixth embodiments, the carrier comprises, consists essentially of, or consists of: a polymer carrier, a polymerizable carrier, a wax carrier, or an electrostatically printable particulate carrier. In embodiments, components further included in the carrier are nucleating agents, oils, water scavengers, desiccants, adhesion promoters, antifouling agents, thermal or oxidative stabilizers, colorants, adjuvants, plasticizers, or two more thereof. Components are not generally limited in nature and are dictated by the particular end use of the cyclodextrin compositions and treated substrates, further within the boundaries for the carrier properties set forth above.

In sixth embodiments, the polymer carrier comprises, consists essentially of, or consists of one or more polymers, that is, one or more compounds having two or more repeating units; and one or more non-aqueous solvents. The amounts of polymer and solvent are selected by the user to provide a targeted viscosity or other physical property suitable for coating the coating composition on a substrate.

In embodiments, the one or more polymers comprise, consist of, or consist essentially of homopolymers, copolymers (herein construed to include any polymers comprising more than one type of monomer residue such as terpolymers, tetra polymers and the like), or a combination thereof. The copolymers may be block copolymers, random copolymers, and/or alternating copolymers. The polymers are linear polymers, branched polymers, radial polymers, dendritic polymers, or any combination thereof. In embodiments, the one or more polymers comprises one or more addition polymers, one or more condensation polymers, or any combination thereof.

In embodiments, a polymer is selected from poly(alpha hydroxy acids) (i.e. poly(alpha hydroxy carboxylic acids), polysaccharides, chemically modified polysaccharides, polyamides, polyolefins, thermoplastic polyurethanes, polyureas, polyacrylates, polystyrenes, polyesters, polybutadienes, polysiloxanes, polyalkylsilanes, polyvinyl halides, polyvinylidene halides, polyacrylonitriles, polycarbonates, polyethers, polyglycerols, polyethylene imines, nucleic acids, poly(phenylene oxide)s, polymethacrylamides, poly (N-alkylacrylamides), poly(divinyl ether), polyvinyl acetate, polyvinyl alcohol and copolymers thereof, furan resin (poly (2-furanmethanol)), polyhydroxyalkanoates, polyindole, polymethacrylonitrile, and any combination thereof.

In embodiments, a polymer is selected from poly(lactic acid), polyamide, nitrocellulose, polyvinyl butyral, vinyl formal vinyl acetate copolymer, styrene acrylate copolymer, styrene divinyl benzene copolymer, polyester resin, styrene butadiene copolymer, and any combination thereof. In some such embodiments, the polymer is selected from the group consisting of polyamide, nitrocellulose, and a combination thereof. In some such embodiments, the polymer comprises, consists of, or consists essentially of a polyamide that is a condensation product of a diamine and a dibasic acid mixture comprising dibasic acid dimers. In some such embodiments, the dibasic acid mixture comprises, consists of, or consists essentially of C20-C44 dibasic acid dimers, a C6-C12 dibasic acid, or a combination thereof. In some such embodiments, the C20-C44 dibasic acid dimers comprise, consist of, or consist essentially of a C36 dibasic acid dimer. In embodiments, the C6-C12 dibasic acid comprises, consists of, or consists essentially of azelaic acid.

In embodiments, the polymer comprises, consists of, or consists essentially of nitrocellulose, a polyamide, or a combination thereof. In some such embodiments, the polymer is a polyamide disclosed in U.S. Pat. No. 5,658,968. In embodiments, the polyamide is a product of a diamine composition and a dibasic acid composition. In embodiments, the diamine composition comprises, consists of, or consists essentially of a C2-C5 diamine, a C6-C12 alkyl diamine, or a combination thereof. In embodiments, the C2-C5 diamine comprises, consists of, or consists essentially of ethylene diamine and hexamethylene diamine. In embodiments, the dibasic acid composition comprises, consists of, or consists essentially of a C20-C44 dibasic acid dimers, a C6-C12 dibasic acid, or a combination thereof. In embodiments, the dibasic acid composition comprises, consists of, or consists essentially of a C36 dibasic acid dimer, azelaic acid, and n-propanoic acid. In embodiments, the organic solvent comprises, consists of, or consists essentially of ethyl acetate, ethanol, isopropyl acetate, 1-propoxy-2-propanol, heptane, naphtha, propan-1-ol, toluene, or any combination thereof. In embodiments, the polyamide has a weight average molecular weight of about 8,000 to about 12,000.

Non-aqueous solvents useful in the polymer carriers of sixth embodiments include ketones, esters, aldehydes, ketals, acetals, hydrocarbon solvents, amides, ethers, polyols, alcohols, and any combination thereof.

Ketones include but are not limited to aromatic, linear, branched, cyclic or alicyclic saturated or unsaturated ketones having 3 to 10 carbons. exemplary ketones include but are not limited to acetone, methyl ethyl ketone (butanone), 2-pentanone, 3-pentanone, methyl isopropyl ketone, ethyl isopropyl ketone, methyl isobutyl ketone, 2-hexanone, acetophenone, cyclopentanone, isophorone, and any combination thereof.

Ketals include but are not limited to 2-methyl-2-ethyl-1, 3-dioxolane; and any one or more ketal reaction products of ethylene glycol, propylene glycol, a sugar alcohol (including glycerol and erythritol) or a sugar with any one or more ketones, ketoesters, and any combination thereof. Acetals include dimethoxymethane, dioxolane, paraldehyde, and any one or more ketal reaction products of ethylene glycol, propylene glycol, a sugar alcohol (including glycerol and erythritol) or a sugar with any one or more of a ketone, ketoester, and any combination thereof.

Amides include but are not limited to formamide, N-methyl formamide, dimethyl formamide, dimethylacetamide, 2-pyrrolidone, N-methyl-2-pyrrolidone, N-vinylacetamide, N-vinylpyrrolidone, and any combination thereof. Aldehydes include but are not limited to formaldehyde, acetaldehyde, propionaldehyde, dimethyl formamide, dimethyl carbonate, N-methylmorpholine N-oxide, and any combination thereof. Ethers include but are not limited to dimethyl ether, tetrahydrofuran, glycol ethers, diethyl ether, and any combination thereof Polyols include but are not limited to glycols and sugar alcohols such as glycerol and erythritol. Esters include but are not limited to aromatic, linear, branched, cyclic or alicyclic saturated or unsaturated alkyl esters having 4 to 20 carbons. Esters include but are not limited to ethyl acetate, ethyl propionate, animal or plant triglycerides, biodiesel, glycol esters, and any combination thereof. Alcohols include but are not limited to ethanol, n-propanol, isopropanol, n-butanol, isobutanol, t-butyl alcohol, and any combination thereof.

Hydrocarbon solvents include but are not limited to aromatic, linear, branched, cyclic or alicyclic saturated or unsaturated compounds having 6 to 20 carbons or mixtures thereof, or halogenated versions thereof such as chlorinated, fluorinated, or brominated versions thereof; halogenated hydrocarbons having 1 to 5 carbons; and cyclic aliphatic or aromatic compounds having one or more N, S, or O atoms incorporated within the ring, such as furans, pyrroles, thiophenes, pyridines, morpholines, dioxanes, and pyrans, alkylated or hydrogenated versions thereof, and mixtures thereof, petroleum distillates of crude oil such as mineral spirits, kerosene, white spirits, naphtha, and Stoddard solvent (CAS ID #: 8052-41-3); paraffinic distillates, and isoparaffinic fluids such as ISOPAR® fluids manufactured by ExxonMobil Chemical Co. of Houston, Tex.

In some embodiments, a solvent compound includes two more functional groups such as two or more ester, amide, keto, aldehyde, hydroxyl, ketal, acetal, or other such functional group. Examples of such compounds include β-hydroxy aldehydes, β-hydroxy ketones, β-hydroxy esters, β-keto esters, semialdehydes, ketal esters, and the like. Generally such compounds have between 3 and 12 carbons.

In embodiments, the organic solvent comprises, consists of, or consists essentially of ethyl acetate, heptane, methanol, ethanol, propan-1-ol, isopropanol, n-propyl acetate, isopropyl acetate, 1-propoxy-2-propanol, 1-pentene, n-pentane, 1-hexene, n-hexane, benzene, cyclohexane, 3-methylhexane, 1-heptene, n-heptane, 2,5-dimethylcyclohexane, toluene, 1-octene, n-octane, ethylbenzene, m-xylene, p-xylene, 1-decene, n-decane, or any combination thereof. In embodiments, the organic solvent comprises, consists of, or consists essentially of one or more solvents selected from the group consisting of ethyl acetate, heptane, ethanol, methanol, naphtha, propan-1-ol, isopropanol, isopropyl acetate, or any combination thereof.

Naphtha is a mixture of liquid hydrocarbons. As used herein, it may include light naphtha (a fraction boiling between 30° C. and 90° C. at 1 atmosphere of pressure), heavy naphtha (a fraction boiling between 90° C. and 200° C.), or a combination thereof. In embodiments, the naphtha comprises, consists of, or consists essentially of light naphtha. In embodiments, the naphtha comprises or consists essentially of n-pentane, 1-hexene, n-hexane, cyclohexane, 3-methyl heptane, 1-heptene, n-heptane, toluene, 1-octene, n-octane, ethylcyclohexane, ethylbenzene, m-xylene, p-xylene, 1-decene, n-decane, or any combination thereof.

In sixth embodiments, a polymer carrier is formed by admixing one or more polymers with one or more non-aqueous solvents, employing conventional mixing methodology for obtaining polymer solutions or dispersions. In embodiments, the polymer carrier includes about 1 wt % to about 80 wt % total of the one or more polymers in the polymer carrier, for example 1 wt % to 75 wt %, or 1 wt % to 70 wt %, or 1 wt % to 65 wt %, or 1 wt % to 60 wt %, or 1 wt % to 55 wt %, or 1 wt % to 50 wt %, or 1 wt % to 45 wt %, or 1 wt % to 40 wt %, or 1 wt % to 35 wt %, or 1 wt % to 30 wt %, or 1 wt % to 25 wt %, or 1 wt % to 20 wt %, or 1 wt % to 15 wt %, or 1 wt % to 10 wt %, or 1 wt % to 9 wt %, or 1 wt % to 8 wt %, or 1 wt % to 7 wt %, or 1 wt % to 6 wt %, or 1 wt % to 5 wt %, or 5 wt % to 75 wt %, or 10 wt % to 75 wt %, or 15 wt % to 75 wt %, or 20 wt % to 75 wt %, or 25 wt % to 75 wt %, or 30 wt % to 75 wt %, or 35 wt % to 75 wt %, or 40 wt % to 75 wt %, or 45 wt % to 75 wt %, or 50 wt % to 75 wt % total of the one or more polymers in the polymer carrier.

In sixth embodiments, the polymerizable carrier comprises, consists essentially of, or consists of one or more α,β-unsaturated monomers that are liquids within a temperature range of 0° C. to 50° C. at atmospheric pressure and are capable of polymerization when irradiated with electromagnetic radiation. The α,β-unsaturated monomers useful in the polymerizable carriers are selected from acrylates, methacrylates, acrylamides, methacrylamides, allylic monomers, α-olefins, butadiene, styrene and styrene derivatives, acrylonitrile, and the like. Some examples of useful monomers include acrylic acid, methacrylic acid, and alkyl esters of acrylic or methacrylic acid wherein the ester groups have between 1 and 18 carbons, in some embodiments between 1 and 8 carbons, and are linear, branched, or cyclic. In embodiments, the polymerizable carrier includes blends of two or more monomers. In some such embodiments, one or more monomers are selected to target specific permeability properties to water vapor, 1-MCP gas, or both.

In some sixth embodiments, the polymerizable carrier comprises one or more monomers having two or more unsaturated and polymerizable bonds. Such polyfunctional monomers, which function as crosslinkers, include diacrylates such as ethylene glycol diacrylate, hexanediol diacrylate, and tripropyleneglycol diacrylate; triacrylates such as glycerol triacrylate and trimethylolpropane triacrylate; and tetraacrylates such as erythritol tetraacrylate and pentaerythritol tetraacrylate; divinyl benzene and derivatives thereof, and the like. Such monomers provide crosslinking to the cured cyclodextrin composition.

In some such embodiments, a crosslinker or mixture thereof, is present at less than about 10% by weight of the polymerizable carrier, for example at about 0.1% to 5% by weight of the polymerizable carrier or even 0.01% to 1% by weight of the polymerizable carrier.

In some embodiments the polymerizable carrier further includes a photoinitiator. In some embodiments where affixing (discussed below) is carried out by UV irradiation, the photoinitiator absorbs the UV radiation and becomes activated, thereby initiating the polymerization or of the monomers. In such embodiments, the photoinitiator is selected based on the wavelength of UV radiation to be employed. Where a photoinitiator is present in the polymerizable carrier, it is included in the cyclodextrin compositions at about 0.01% by weight to 5% by weight based on the weight of the coating composition, for example 0.5% by weight to 2% by weight based on the weight of the coating composition. Examples of suitable photoinitiators include those sold under the trade name IRGACURE® by Ciba Specialty Chemicals Corp. of Tarrytown, N.Y.; those sold under the trade name CHEMCURE® by Sun Chemical Company of Tokyo, Japan; and LUCIRIN® TPO sold by BASF Corporation of Charlotte, N.C.

In sixth embodiments, the wax carrier comprises, consists essentially of, or consists of one or more waxes. A wax comprises, consists essentially of, or consists of a mixture of compounds characterized by melting transition onsets, of 23° C. to about 60° C., such as 23° C. to 50° C. or 23° C. to 40° C.; and water contact angle of 90° or greater when measured according to ASTM D7334-08 or alternatively solubility in water of less than 1 wt % at 25° C. In some embodiments, the wax comprises, consists essentially of, or consists of a petrolatum or a petrolatum-like material. Petrolatum (Merkur; mineral jelly; petroleum jelly; CAS No. [8009-03-8]; EINECS No. 232-373-2) is a purified mixture of semisolid saturated hydrocarbons having the general formula $C_nH_{2n+2}$, and is obtained from petroleum sources. The hydrocarbons consist mainly of branched and unbranched chains although some cyclic alkanes and aromatic molecules with alkyl side chains may also be present.

In some embodiments, the wax comprises, consists essentially of, or consists of petrolatum-like material that is sourced from vegetable matter. Such materials are described, for example, in U.S. Pat. No. 7,842,746. The vegetable based petrolatum-like materials are made from hydrogenated polymerized vegetable oils, such as hydrogenated blown oils or hydrogenated copolymerized oils. The petrolatum-like materials are formulated to have a targeted range of properties and thus are suitably formulated to have melting transition onset of between about 23° C. and 40° C., as well as water contact angle to the surface of 90° or greater, measured according to ASTM D7334-08, and/or solubility in water of less than 1 wt % at 25° C.

In some embodiments, oils are included in the wax carrier. Oils are hydrophobic compounds that are liquids at 25° C., wherein hydrophobic means solubility in water of less than 1 wt % at 25° C. In some embodiments, the oil is a hydrocarbon or silicone oil; in other embodiments the oil is a plant oil such as peanut oil, walnut oil, canola oil, linseed oil, and the like. In some embodiments, the oil is a "drying oil", that is, the oil reacts with oxygen in the atmosphere to form crosslinks. In embodiments, one or more oils are added to the wax carrier at about 0.1 wt % to 10 wt % of the weight of the carrier, or about 0.5 wt % to 5 wt % of the weight of the carrier, or about 0.1 wt % to 5 wt % of the weight of the carrier.

In sixth embodiments, the electrostatically printable carrier comprises, consists essentially of, or consists of an electrostatically printable particulate. The electrostatically printable particulate is a mixture of one or more polymers (selected in embodiments from the polymers listed above regarding the polymer carrier) in a particulate form, that is, a polymer particulate; the polymer particulate optionally includes one or more additional components associated with electrophotographic toner compositions, such as charge control agents and colorants. Useful polymer particles suitably employed in electrostatically printable carriers include styrene acrylate copolymers, styrene divinyl benzene copolymers, polyester resins, styrene butadiene copolymers, and polyolefins, wherein the polymer particles have particle sizes in the range of about 5 µm to 50 µm in the largest direction. In some embodiments the electrostatically printable carrier is a previously manufactured toner composition employed for electrostatic printing.

Further in sixth embodiments, combinations of the foregoing carriers or individual components thereof are suitably mixed to form a carrier blend. Non-limiting examples of such carrier blends include a polymerizable carrier mixed with a wax or a polymer or both; a wax carrier mixed with a non-aqueous solvent, and the like without limitation. Coating compositions as defined herein include any such carrier blends without limit. In some embodiments carrier may further include one or more fillers, which include but not limited to polymer beads and bubbles; glass or ceramic beads or bubbles; mineral particulates such as silicas, calcium carbonate; and similar inert materials.

In sixth embodiments, a carrier as described above is mixed with a modified particulate to form a coating composition. The mixing is accomplished by one more methods known to those of skill in mixing powders with liquids or in mixing two particulate solids. nonlimiting examples of useful mixing methods include static mixing, injection mixing, stirring, blade mixing, sonicating, or a combination thereof. Where a coating composition includes more than two components, order of mixing the components is not limited except as required by the specific coating composition targeted, that is, the components thereof and their interactions. For example, it may be advantageous to mix a polymer with a non-aqueous solvent prior to mixing the modified particulate with the polymer/solvent combination, in order to fully disperse or dissolve the polymer in the solvent prior to mixing the modified particulate with the polymer/solvent combination. Further, it may be useful to heat one or more carrier components to facilitate mixing; heating without limitation is useful except, however, that when the modified particulate is mixed with the carrier or component thereof, the carrier or component thereof should have a temperature of 90° C. or less, preferably 80° C. or less. Further, it may be advantageous to dry a carrier or carrier component in order to obtain a coating composition having less than 5 wt % water after the mixing is completed.

In sixth embodiments, a coating composition comprises, consists essentially of, or consists of a carrier and a modified particulate of any of first through fourth embodiments. The amount of the modified particulate in the coating composition is not particularly limited; however, in some industrially useful embodiments the coating composition includes between about 0.001 g/L and 500 g/L of the modified particulate based on the volume of the coating composition, or similarly 0.001 g/kg to 500 g/kg of the modified particulate based on the weight of the coating composition, for example 0.0001 wt % to 45 wt %, or 0.0001 wt % to 40 wt %, or 0.0001 wt % to 35 wt %, or 0.0001 wt % to 30 wt %, or 0.0001 wt % to 25 wt %, or 0.0001 wt % to 20 wt %, or 0.0001 wt % to 15 wt %, or 0.0001 wt % to 10 wt %, or 0.0001 wt % to 5 wt %, or 0.0001 wt % to 1 wt %, or 0.001 wt % to 50 wt %, or 0.001 wt % to 45 wt %, or 0.001 wt % to 40 wt %, or 0.001 wt % to 35 wt %, or 0.001 wt % to 30 wt %, or 0.001 wt % to 25 wt %, or 0.001 wt % to 20 wt %, or 0.001 wt % to 15 wt %, or 0.001 wt % to 10 wt %, or 0.001 wt % to 5 wt %, or 0.001 wt % to 1 wt %, or 0.01 wt % to 50 wt %, or 0.01 wt % to 45 wt %, or 0.01 wt % to 40 wt %, or 0.01 wt % to 35 wt %, or 0.01 wt % to 30 wt %, or 0.01 wt % to 25 wt %, or 0.01 wt % to 20 wt %, or 0.01 wt % to 15 wt %, or 0.01 wt % to 10 wt %, or 0.01 wt % to 5 wt %, or 0.01 wt % to 1 wt %, or 1 wt % to 50 wt %, or 1 wt % to 45 wt %, or 1 wt % to 40 wt %, or 1 wt % to 35 wt %, or 1 wt % to 30 wt %, or 1 wt % to 25 wt %, or 1 wt % to 20 wt %, or 1 wt % to 15 wt %, or 1 wt % to 10 wt %, or 1 wt % to 9 wt %, or 1 wt % to 8 wt %, or 1 wt % to 7 wt %, or 1 wt % to 6 wt %, or 1 wt % to 5 wt %, or 1 wt % to 4 wt %, or 1 wt % to 3 wt % of the modified particulate based on the weight of the coating composition.

In sixth embodiments, coating the coating composition onto a substrate includes coating using one or more industrially useful methods selected from die coating including drop die and horizontal die coating, slot coating, brush coating, spray coating, flood coating, curtain coating, screen printing, inkjet printing, gravure or reverse gravure coating, flexographic printing, or electrostatic printing. Coating the coating composition includes use of temperatures of 90° C. or less, preferably 80° C. or less, during and throughout the coating process.

Substrates usefully employed to form the coated substrates of the invention include any substrate suitable for disposition of the coating composition on at least a portion of a surface thereof. In some embodiments, the substrate surface is the surface of a plate, film, or sheet and thus is substantially planar and well suited for continuous industrial coating operations. In other embodiments, the coating composition is disposed on a non-planar substrate surface or an irregular substrate surface to form a coated substrate. In some embodiments, the substrate is a container. Suitable substrates include cellulosic and other natural and synthetic biomass-based substrates, as well as synthetic petroleum-based thermoplastic polymeric films, sheets, fibers, or woven, felted, or nonwoven fabrics, and composite materials including one or more thereof. Some examples of substrates usefully employed to form coated substrates include paper, paperboard, cardboard, carton board such as corrugated cardboard, coated paper or cardboard such as extrusion coated paper or cardboard, chipboard, nonwoven, felted, or woven fabrics, wood, netting, wood/thermoplastic composites, glass, metals, polyvinyl halides such as poly (vinyl chloride) (plasticized and unplasticized) and copolymers thereof polyvinylidene halides such as polyvinylidene chloride and copolymers thereof polyolefins such as polyethylene, polypropylene, copolymers thereof, and morphological variations thereof including LLDPE, LDPE, HDPE, UHMWPE, metallocene polymerized polypropylene, and the like; polyesters such as polyethylene terephthalate (PET) or polylactic acid (PLA) and plasticized variations thereof polystyrene and copolymers thereof including HIPS; polyvinyl alcohol and copolymers thereof; copolymers of ethylene and vinyl acetate; and the like. Blends, alloys, composites, crosslinked versions thereof, and recycled versions thereof are also useful in various embodiments. Two or more layers of such substrates are present in some embodiments as multilayer films or sheets. In some embodiments, the substrates are substantially continuous. In some embodiments the substrates are permeable, porous, microporous, perforated, meshed, foamed (open- or closed-cell), woven or nonwoven fabrics, or netting.

In embodiments, the substrate is or includes a polyolefin, polyolefin plastomer, a styrene butadiene copolymer, or a polyester. In some such embodiments the substrate is oriented in one direction or in two directions (biaxially oriented). In embodiments, the substrate is an oriented polypropylene film.

In some embodiments the substrates contain one or more fillers, stabilizers, colorants, and the like. In some embodiments the substrates have one or more surface coatings thereon. In some embodiments the substrate has a surface coating thereon prior to coating the coating composition. Surface coatings include protective coatings such as wax, acrylic polymer, vinyl acetate/ethylene copolymer and ethylene/vinyl chloride copolymer coatings, and the like; coatings to render surfaces printable; coatings to render otherwise permeable substrates impermeable; adhesive coatings; primers; tie layer coatings; metalized or reflective coatings; and the like. The type and function of surface coatings are not particularly limited within the scope of this disclosure; likewise the manner in which the surface coatings are applied is not particularly limited. In various embodiments where a surface coating will be exposed to an enclosed or partially enclosed volume within a produce package, the surface coating is subsequently coated with the coating composition.

In some embodiments, the substrate is polyethylene extrusion coated recyclable paperboard, corrugated cardboard, or carton board packaging, for shipment of produce. Printed paperboard or corrugated cardboard packaging ranges from bulk bins to specialized display cartons. The extrusion coated surface provides an opportunity to dispose a coating composition thereon.

In some embodiments the substrate is pretreated with a plasma or corona treatment prior to disposing the coating composition thereon. Such surface treatments are well known in the industry and are often employed in the industry to modify the surface energy of substrates, for example to improve wetting or adhesion of coatings or printed materials to the surface of a substrate. Such surface treatments are likewise useful in some embodiments to improve wetting and adhesion of the coating compositions to the substrate.

In some embodiments, the substrate is treated with a primer prior to disposing the coating composition thereon. In some such embodiments films and sheets of thermoplastics used as substrates are obtained or purchased already pre-coated with a primer; a wide variety of such films and sheets are available in the industry and are targeted for improving adhesion of various types of coatings thereto. In some embodiments a plain film or sheet is coated "in line" with a primer. A plethora of such coatings and technologies are available and one of skill will understand that primer coatings are optimized for each application and for the composition to be disposed thereon. Some examples of primer compositions suitably disposed between the substrate surface and the coating compositions include polyethyleneimine polymers such as polyethyleneimine, alkyl-modified polyethyleneimines in which the alkyl has 1 to 12 carbon atoms, poly(ethyleneimineurea), ethyleneimine adducts of polyaminepolyamides, and epichlorohydrin adducts of polyaminepolyamides, acrylic ester polymers such as acrylamide/acrylic ester copolymers, acrylamide/acrylic ester/methacrylic ester copolymers, polyacrylamide derivatives, acrylic ester polymers containing oxazoline groups, and poly(acrylic ester)s. In embodiments, the primer composition is an acrylic resin, a polyurethane resin, or mixture thereof.

An alternative method to treat or "prime" materials is via a glow discharge using either corona or atmospheric plasma. Both methods are typically used in an air atmosphere but other gases or gas mixtures can also be used and may include, and not limited to, oxygen, nitrogen, argon, helium, carbon dioxide, ammonia, water vapor, etc. The glow discharge treatment has the ability to "clean" material surfaces by removal of contaminants and to create polar moieties on surfaces. In some embodiments, such treatments promote adhesion of disposed materials thereto, uniformity of disposed coatings, or both. Examples of corona and plasma systems are those available from Enercon Industries, Vetaphone, and Plasmatreat. Advantages of corona and plasma treatment include: a) there is no need to add another chemical to the substrate, b) there is no need for drying or post curing of the substrate, c) glow discharge is a highly efficient process from gas utilization efficiency, and d) such processes are well aligned with sustainability guidelines regarding product, occupational and environmental safety.

In sixth embodiments, a coating composition is coated on a substrate surface using one or more methods well known to those of skill in the coating and/or printing industry, further wherein specific coating methodology is determined by the physicochemical properties of the carrier. Coating is carried out using conventional apparatus and condition, excluding conditions wherein the temperature of the modified particulate exceeds 90° C., and preferably excluding conditions wherein the temperature of the modified particulate exceeds 80° C. Coating methods suitably employed to coat the coating compositions include but are not limited to die coating, slot coating, brush coating, spray coating, flood coating, screen printing, fluidized bed coating, inkjet printing, gravure or reverse gravure coating, flexographic printing, electrostatic printing, and the like.

In some embodiments the coating composition is heated to lower the viscosity thereof prior to and/or during the coating. In such embodiments, the heating is heating to a temperature of less than 90° C., preferably to 80° C. or less. The coating method may be continuous coating, which is coating of all or substantially all of a substrate surface with the coating composition; or discontinuous coating, which is coating only a selected portion of the coatable substrate surface with the coating composition. In some embodiments, the discontinuous coating is a pattern coating.

Coating of the coating compositions includes selecting a coating weight of the coating composition on the substrate. Such selection is not particularly limited and in some embodiments is selected for use with a known method or known coating apparatus requirement or limitation. In embodiments the coating is selected to provide 0.1 g/m$^2$ to 100 g/m$^2$ of the coating composition on the substrate, for example 0.1 g/m$^2$ to 90 g/m$^2$, or 0.1 g/m$^2$ to 80 g/m$^2$, or 0.1 g/m$^2$ to 70 g/m$^2$, or 0.1 g/m$^2$ to 60 g/m$^2$, or 0.1 g/m$^2$ to 50 g/m$^2$, or 0.1 g/m$^2$ to 40 g/m$^2$, or 0.1 g/m$^2$ to 30 g/m$^2$, or 0.1 g/m$^2$ to 20 g/m$^2$, or 0.1 g/m$^2$ to 15 g/m$^2$, or 0.1 g/m$^2$ to 10 g/m$^2$, or 1 g/m$^2$ to 90 g/m$^2$, or 1 g/m$^2$ to 80 g/m$^2$, or 1 g/m$^2$ to 70 g/m$^2$, or 1 g/m$^2$ to 60 g/m$^2$, or 1 g/m$^2$ to 50 g/m$^2$, or 1 g/m$^2$ to 40 g/m$^2$, or 1 g/m$^2$ to 30 g/m$^2$, or 1 g/m$^2$ to 20 g/m$^2$, or 1 g/m$^2$ to 15 g/m$^2$, or 1 g/m$^2$ to 10 g/m$^2$ of the coating composition on the substrate.

In sixth embodiments, affixing the coating composition on the substrate surface is accomplished using one or more methods known to those of skill in the coating and/or printing industry, further wherein specific affixing methodology is determined by the physicochemical properties of the carrier and the coating method employed to coat the coating composition on the substrate. Affixing methods suitably employed to affix the coating compositions to the substrate surface include evaporating (drying), irradiating, cooling, and applying heat and pressure.

In sixth embodiments where the carrier includes a polymer and a non-aqueous solvent, affixing comprises or consists of evaporating the solvent from the coated composition. In some embodiments, evaporating comprises or consists of heating the coating composition using set temperatures of 90° C. or below, in embodiments 80° C. or below. In some embodiments, evaporating comprises or consists of convecting by applying a gas such as air, dry air, or dry nitrogen gas to the coating composition. In some embodiments, affixing comprises or consists of a combination of evaporating and convecting.

In sixth embodiments where the carrier includes one or more α,β-unsaturated monomers, affixing comprises or consists of irradiating the coated composition with electromagnetic radiation. In some such embodiments, affixing is accomplished employing UV radiation. UV radiation is electromagnetic radiation having a wavelength of between 10 nm and 400 nm. In embodiments, wavelengths between about 100 nm and 400 nm are useful; in other embodiments wavelengths between about 200 nm and 380 nm are useful. Wavelength, as well as radiation intensity and time of exposure, is selected based on processing parameters such as the absorption characteristics of the photoinitiator employed and polymerization kinetics of the monomer(s) selected. Useful methodologies and criteria to consider in UV curing are described, for example, in U.S. Pat. No. 4,181,752.

In embodiments, affixing by irradiation is accomplished in an environment that is substantially free of atmospheric moisture, air, or both. Such an environment is achieved, in some embodiments, by purging the coated area with an inert gas such as carbon dioxide or nitrogen during the curing. In other embodiments, water and air are suitably excluded by applying a UV-transparent, water impermeable liner on top of the coating composition and prior to the affixing. The liner material is not particularly limited in composition or thickness and is selected for UV transparency at the desired wavelength.

In other embodiments, affixing by irradiation is accomplished employing electron beam, or e-beam, radiation. E-beam methods employed to polymerize the cyclodextrin composition are described, for example, in the web article by Weiss et al., *"Pulsed Electron Beam Polymerization"*, posted Jan. 1, 2006 (http://www.adhesivesmag.com/Articles/Feature Article/ 47965fdd41bc8010VgnVCM100000f932a8c0). Additional information is available as disclosed in U.S. Pat. Nos. 3,940,667; 3,943,103; 6,232,365; 6,271,127; 6,358,670; 7,569,160; 7,799,885, and the like.

In sixth embodiments where the carrier includes a wax, affixing may include cooling the coated composition and in some embodiments additionally laminating the coated composition with a second substrate which is a thermoplastic sheet or film that is the same or different from the substrate onto which the coated composition is affixed.

In sixth embodiments where the carrier is an electrostatically printable particulate, affixing means fusing, wherein fusing means applying pressure and/or heat to the coating composition. Conventional electrostatic printing includes a fusing step wherein a substrate coated with polymer particles (toner) is passed through a heated nip (fusing rollers) to heat and "fuse" the polymer particles to the substrate (partially melt and coalesce the polymer particles of the toner). Such fusing is a suitable method for affixing the coating composition to the substrate, where the coating composition comprises, consists essentially of, or consists of a polymer particulate and a modified particulate.

In embodiments, the fusing comprises passing the substrate and coated composition between the fusing rollers to obtain an applied pressure to the coating composition. In such embodiments, the fusing comprises or consists of providing a physical pressure point to compress the coating composition against the substrate, affixing the coating composition thereto to result in a coated composition. In other embodiments, the fusing rollers are heated, for example by setting the temperature of fusing rollers to about 80° C. to 200° C., or about 100° C. to 190° C., or about 110° C. to 180° C., or about 120° C. to 170° C., or about 130° C. to 160° C., or about 130° C. to 150° C. For example, in some embodiments where the substrate includes a wax coating thereon, the fusing rollers are not heated or are heated to a temperature of about 100° C. or less, such as 60° C. to 90° C.

Accordingly, in sixth embodiments, affixing the coating composition to the substrate results in a coated substrate. The coated substrates of sixth embodiments comprise, consist essentially of, or consist of a substrate having a coating affixed to at least a portion of a surface thereof, wherein the affixed coating comprises, consists essentially of, or consists of a polymer, a wax, or a combination thereof; and a modified particulate of any of first through fourth embodiments dispersed within the coating. The polymer or wax is present as a result of affixing methods that include evaporating, irradiating, or fusing.

In sixth embodiments, the thickness and coating weight of the affixed coating are selected by the user in accord with one or more commercially useful embodiments, further in accord with the physicochemical properties of the carrier and the weight percent of modified particulate dispersed in the coating. In some sixth embodiments, the coating thickness is between 0.01 μm and 50 μm thick on all or a portion of the coated substrate surface, for example 0.01 μm to 40 μm, or 0.01 μm to 30 μm, or 0.01 μm to 25 μm, or 0.01 μm to 20 μm, or 0.01 μm to 15 μm, or 0.01 μm to 10 μm, or 0.01 μm to 9 μm, or 0.01 μm to 8 μm, or 0.01 μm to 7 μm, or 0.01 μm to 6 μm, or 0.01 μm to 5 μm, or 0.01 μm to 4 μm, or 0.01 μm to 3 μm, or 0.01 μm to 2 μm, or 0.01 μm to 1 μm, or 0.1 μm to 40 μm, or 0.1 μm to 30 μm, or 0.1 μm to 25 μm, or 0.1 μm to 20 μm, or 0.1 μm to 15 μm, or 0.1 μm to 10 μm, or 0.1 μm to 9 μm, or 0.1 μm to 8 μm, or 0.1 μm to 7 μm, or 0.1 μm to 6 μm, or 0.1 μm to 5 μm, or 0.1 μm to 4 μm, or 0.1 μm to 3 μm, or 0.1 μm to 2 μm, or 0.1 μm to 1 μm, or 1 μm to 50 μm, or 1 μm to 40 μm, or 1 μm to 30 μm, or 1 μm to 20 μm, or 1 μm to 10 μm, or 1 μm to 5 μm, or 5 μm to 50 μm, or 5 μm to 40 μm, or 5 μm to 30 μm, or 5 μm to 20 μm, or 5 μm to 10 μm thick on all or a portion of the coated substrate surface.

In some sixth embodiments, the coating obtains a coating weight of 0.01 $g/m^2$ to 10 $g/m^2$ on the substrate, for example 0.01 $g/m^2$ to 9 $g/m^2$, or 0.01 $g/m^2$ to 8 $g/m^2$, or 0.01 $g/m^2$ to 7 $g/m^2$, or 0.01 $g/m^2$ to 6 $g/m^2$, or 0.01 $g/m^2$ to 5 $g/m^2$, or 0.01 $g/m^2$ to 4 $g/m^2$, or 0.01 $g/m^2$ to 3 $g/m^2$, or 0.01 $g/m^2$ to 2 $g/m^2$, or 0.01 $g/m^2$ to 1 $g/m^2$, or 0.1 $g/m^2$ to 10 $g/m^2$, or 0.1 $g/m^2$ to 9 $g/m^2$, or 0.1 $g/m^2$ to 8 $g/m^2$, or 0.1 $g/m^2$ to 7 $g/m^2$, or 0.1 $g/m^2$ to 6 $g/m^2$, or 0.1 $g/m^2$ to 5 $g/m^2$, or 0.1 $g/m^2$ to 4 $g/m^2$, or 0.1 $g/m^2$ to 3 $g/m^2$, or 0.1 $g/m^2$ to 2 $g/m^2$, or 0.1 $g/m^2$ to 1 $g/m^2$, or 0.5 $g/m^2$ to 10 $g/m^2$, or 0.5 $g/m^2$ to 9 $g/m^2$, or 0.5 $g/m^2$ to 8 $g/m^2$, or 0.5 $g/m^2$ to 7 $g/m^2$, or 0.5 $g/m^2$ to 6 $g/m^2$, or 0.5 $g/m^2$ to 5 $g/m^2$, or 0.5 $g/m^2$ to 4 $g/m^2$, or 0.5 $g/m^2$ to 3 $g/m^2$, or 0.5 $g/m^2$ to 2 $g/m^2$, or 0.5 $g/m^2$ to 1 $g/m^2$, or 1 $g/m^2$ to 10 $g/m^2$, or 1 $g/m^2$ to 9 $g/m^2$, or 1 $g/m^2$ to 8 $g/m^2$, or 1 $g/m^2$ to 7 $g/m^2$, or 1 $g/m^2$ to 6 $g/m^2$, or 1 $g/m^2$ to 5 $g/m^2$, or 1 $g/m^2$ to 4 $g/m^2$, or 1 $g/m^2$ to 3 $g/m^2$, or 1 $g/m^2$ to 2 $g/m^2$ on the substrate.

Seventh Embodiments

Seventh embodiments are methods of disgorging 1-MCP from the modified particulate of first through fourth embodiments, the modified particulate pouches of fifth embodiments, or the coated substrates of sixth embodiments by subjecting the modified particulate of first through sixth embodiments to disgorgement conditions.

Disgorgement conditions refer to the atmospheric conditions of ambient pressure (about 1 atm), temperature between 0° C. and about 50° C., and relative humidity of about 80% to 100%. Subjecting the modified particulate of first through fourth embodiments, the modified particulate pouches of fifth embodiments, or the coated substrates of sixth embodiments to disgorgement conditions will cause release of 1-MCP gas therefrom. Such conditions maintained over a period of between 1 minute and 1 year will cause continuous release of 1-MCP until the gas is depleted. Disgorgement conditions of the modified particulates of first through fourth embodiments, pouches of fifth embodiments, and coated substrates of sixth embodiments are the same as disgorgement conditions for the (unmodified) particulate products, including pouches and coated substrates comprising unmodified particulate products. When subjected to identical disgorgement conditions of humidity, temperature, and pressure, the modified and unmodified particulates exhibit different rates of 1-MCP disgorgement. When subjected to identical disgorgement conditions of humidity, temperature, and pressure, pouches or coated substrates comprising a modified particulate exhibit different rates of 1-MCP disgorgement from pouches or coated substrates comprising the unmodified particulate.

We have found that differences in mean particle size as small as 1 μm are sufficient to cause a measurable difference in the rate of 1-MCP disgorgement from 1-MCP clathrate particulates, when the particulates are subjected to disgorgement conditions. Thus, a first modified particulate having a mean particle size of 4 μm releases measurably faster than a second modified particulate having a mean particle size of 5 μm, and so on for any selected mean particle size.

While further presence of liquid water proximal to or even in contact with the modified particulates of first through fourth embodiments, pouches of fifth embodiments, and coated substrates of sixth embodiments is not excluded herein, it is not necessary to include or use liquid water to obtain disgorgement of 1-MCP.

In some seventh embodiments, a portion of the water vapor contacting the modified particulates of first through fourth embodiments, pouches of fifth embodiments, or coated substrates of sixth embodiments is supplied by biological respiration of a living plant or portion thereof, wherein the living plant or portion thereof is situated proximal to the modified particulates of first through fourth embodiments, pouches of fifth embodiments, or coated substrates of sixth embodiments. Accordingly, in such seventh embodiments, subjecting to disgorgement conditions suitably includes placing the modified particulates of first through fourth embodiments, pouches of fifth embodiments, or coated substrates of sixth embodiments proximal to living plant material, wherein water vapor from respiration of the living plant material can contact the modified particulate, pouch, or coated substrate.

EXPERIMENTAL

General Procedures

Characterization of Particle Size of Alpha-Cyclodextrin/1-Methyl Cyclopropene Complexes Mean particle size, median particle size, mode size, specific surface area, and diameter on cumulative were measured using a HORIBA LA-950 Laser Particle Size Analyzer, available from Horiba Scientific.

Concentration of 1-Methylcyclopropene (1-MCP) in Container Headspaces

Concentration of 1-methyl cyclopropene volume/volume) in container headspace gas was measured by removing 250 mL of the headspace gas using a six port, two-position gas sampling valve (available for example as Valco #EC6W from Valco Instruments Inc. of Houston, Tex.) interfaced directly to a gas chromatograph (e.g. Agilent 7890B) using a RTx-5 GC column, 30 m×0.25 mm I.D., 0.25 μm film (available from Restek, Inc., of Bellefonte, Pa.) equipped with a flame ionization detector (FID) and calibrated against a 6-point 1-butene (99.0% pure, available for example from Scott Specialty Gases, Plumsteadville, Pa.; also known as Air Liquide America Specialty Gases LLC) calibration curve. Employing this method, the amount of 1-MCP released (measured as μL/L-volume/volume (v/v)) from the sample of 1-MCP/alpha-cyclodextrin complex was obtained.

Drying of Liquids

Liquid such as overprint varnish, polymer solutions, and organic solvents were dried as follows: A vacuum oven equipped with a vacuum pump and solvent trap was preheated to 220° C. Molecular sieve (Delta Adsorbents 4 Å 8×12B) of nominal pore size 4 Å and 8×12 mesh was placed in Pyrex® pans in the vacuum oven, and the molecular sieve was dried for eight hours at 220° C. Then the oven was shut off and the molecular sieve was allowed to cool for about 16 hours under vacuum. The following day, the molecular sieve was transferred to and enclosed in one-gallon glass jars.

About 2.5 gallons of the liquid to be dried was disposed in a five-gallon pail. Dried molecular sieve (25% by weight of the liquid) was added to the liquid in the pail. The five-gallon pail was sealed, the lid of the pail was vented, and the mixture of molecular sieve and the liquid was allowed to dry for five days before the dried liquid was decanted off the molecular sieve into an airtight pail that was then sealed.

Measurement of Moisture Content of Organic Liquids

Moisture content of liquids such as overprint varnish was measured for moisture content by Karl Fisher moisture analysis using a Metrohm TITRANDO 851 coulometer.

Measurement of Percent Solids of Solutions

The percent solids of solutions such as overprint varnish was determined as follows: About 1 ml of the solution was added to each of three pre-weighed aluminum dishes. Each dish was reweighed. The dishes were then heated at 160° C. for one hour. Each dish was then reweighed. The percent solids of each sample was calculated from the weight difference between the weight of the dish before heating and after heating. Then the mean of the three individual values was calculated.

Measurement of Coating Weights

To measure coating weight, 1000 feet (304.8 meters) of a 13-inch wide (0.3302-meter wide) of coated roll was wound onto a weighed core having a diameter of three inches (0.0762 meters). The wound roll was reweighed, and the weight of the core was subtracted from the weight of the coated roll to reveal the weight of the coated substrate. Next 1000 feet (304.8 meters) of the uncoated substrate used in the coating of for Coating Rolls 1-4 was wound onto a weighed core having a diameter of three inches (0.0762 meters). The weight of the substrate was calculated. The weight of the substrate was then subtracted from the weight of the coated substrate to yield the weight of the coating. The coating weight was then converted to grams per square inch and grams per square meter.

Examples

Example 1

A sample of Batch Y of alpha-cyclodextrin complex of 1-methylcyclopropene (HAIP, obtained from AgroFresh Solutions), was taken and the particle size measured by HORIBA LA-950 Laser Particle Size Analyzer. A portion of Batch Y was milled by Jet milling to reduce the mean particle size of the HAIP (as measured by HORIBA LA-950 Laser Particle Size Analyzer) from an initial mean particle size of about 46 microns to a mean particle size of about 5 microns to produce Batch Z. Therefore Batch Z was a portion of Batch Y that had been milled by jet milling. The particle size of the milled material, Batch Z, was also measured by HORIBA LA-950 Laser Particle Size Analyzer. The particle sizes of Batch Y and Batch Z are displayed in TABLE 1.

Figure 2:
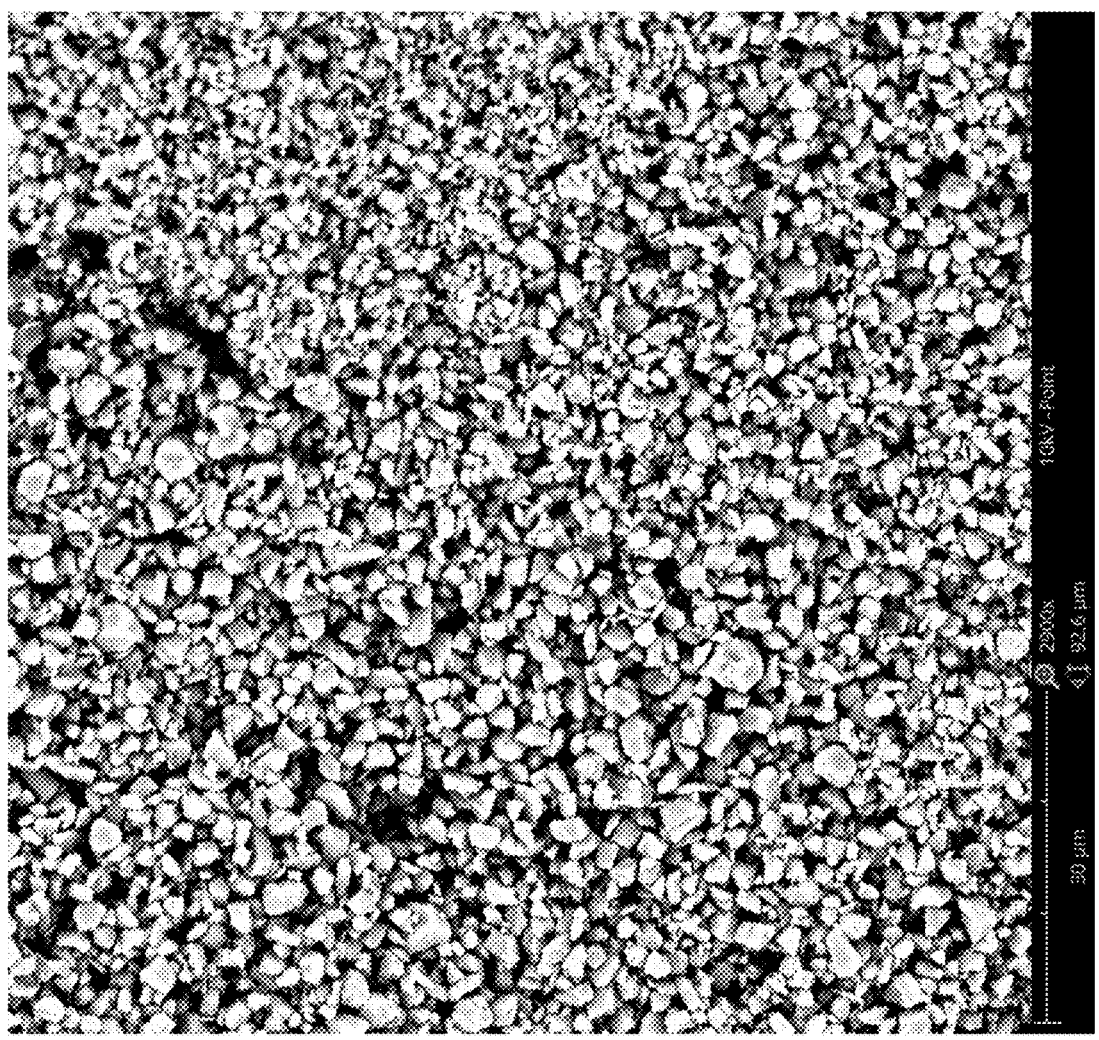
FIG. 2 is a micrographic image of a modified particulate of the invention.

Images of Batch Y and Batch Z were obtained using scanning electron microscopy. FIG. 1 shows the scanning electron micrograph of Batch Y (i.e. before milling) and FIG. 2 shows the scanning electron micrograph of the same material but after milling—Batch Z. The much smaller particle size of Batch Z than Batch Y is evident from the two images.

TABLE 1

Alpha-cyclodextrin/1-MCP complex particle size results

| | | Batch Y | Batch Z |
|---|---|---|---|
| Mean particle size (μm) | | 46.2 | 5.0 |
| Diameter on | D10 | 11.1 | 2.2 |
| cumulative | D50 | 40.2 | 4.3 |
| % (μm) | D90 | 88.9 | S.5 |

Example 2

An oriented polypropylene (PP) (Q00061, 100 gauge from Profol Kunststoffe GmbH), was used to prepare six plastic pouches as follows. Six 4-inch by 8-inch (10.16 cm by 20.32 cm) sheets were cut from the polypropylene. Each sheet was folded in half so that the resulting folded substrate was four inches by four inches (10.16 cm by 10.16 cm). Two edges of each folded substrate were heat-sealed using a heat sealer (H-1254 from Uline) to form a pouch with an open end. Six open pouches were formed in that way.

Each of three of the pouches was filled with 0.05 g of Batch Y. Each of the remaining three pouches was filled with 0.05 g of Batch Z. The open ends of all six open-ended pouches were heat-sealed using a heat sealer (H-1254 from Uline) to provide six sealed pouches as shown in TABLE 2.

| Sealed pouch | Batch of alpha-cyclodextrin/ 1-MCP HAIP complex |
|---|---|
| P1 | Y |
| P2 |  |
| P3 |  |
| P4 | Z |
| P5 |  |
| P6 |  |

Example 3

Each of pouches P1 to P6 was rolled up and inserted into a 250 mL glass Boston round bottle. One mL of deionized water was injected into each bottle with care taken to avoid injection of water directly onto the pouch. After injection of the water, each bottle was immediately sealed with a TEFLON®-faced silicone rubber septum. For each bottle, 1-MCP in the headspace was measured by removing a 250 µL sample of the headspace gas. A gas sample was removed at 30 minutes, one hour, two hours, four hours, eight hours, and 24 hours after the water injection.

The 1-MCP was measured in each gas sample by removing the 250 µL sample of headspace gas using the method described above in General Procedures. Employing this method, the amount of 1-MCP released (measured as µL/L-volume/volume (v/v), or parts per million (ppm) by volume) from each sealed pouch versus time was obtained. The data are displayed in TABLE 3.

TABLE 3

Concentration of 1-MCP released into headspace as measured by GC in Example 3.

| Batch of complex | Pouch | 1-MCP concentration (ppm) in headspace | | | | | |
|---|---|---|---|---|---|---|---|
| | | 0.5 hours | 1 hour | 2 hours | 4 hours | 8 hours | 24 hours |
| Z | P1 | 0 | 0.364 | 0.979 | 12.585 | 94.683 | 332.620 |
| | P2 | 8.744 | 27.310 | 49.873 | 106.63 | 241.65 | 500.87 |
| | P3 | 0 | 0.561 | 5.205 | 118.46 | 349.95 | 872.82 |
| | Average P1-P3 | 2.91 | 9.41 | 18.69 | 79.23 | 228.76 | 568.77 |
| Y | P4 | 0 | 0 | 0 | 0.369 | 2.131 | 11.612 |
| | P5 | 0 | 0 | 0 | 0 | 0 | 3.406 |
| | P6 | 0 | 0 | 0 | 0 | 0.973 | 6.276 |
| | Average P4-P6 | 0 | 0 | 0 | 0.12 | 1.03 | 7.10 |

Figure 3:
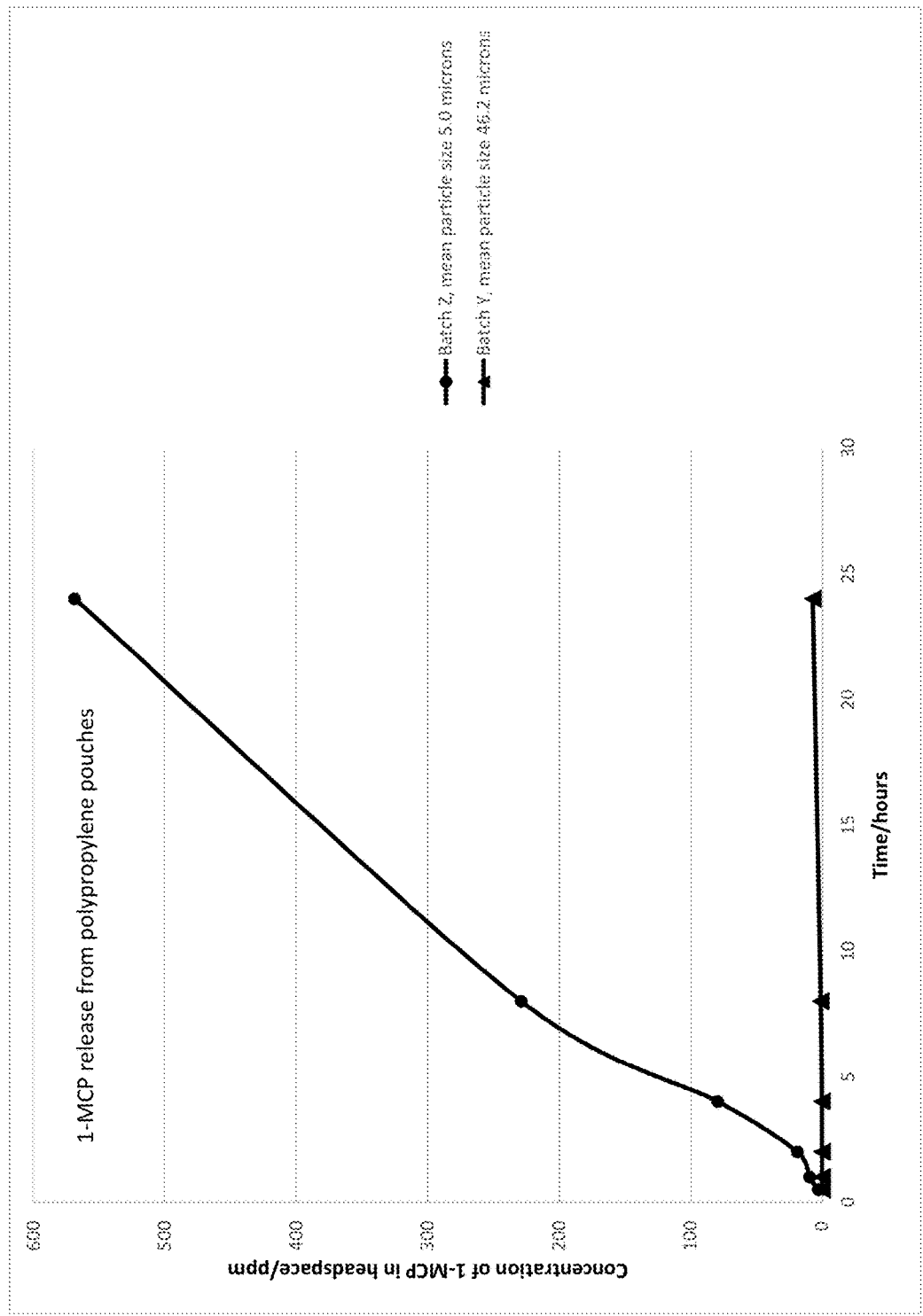
FIG. 3 is a plot of 1-MCP concentration in a headspace as a function of time, in accordance with the procedure of Example 3.

In FIG. 3, the average 1-MCP concentration (volume/volume) released from each pouch into the headspace (displayed in TABLE 3) is plotted against time after water injection.

The concentration of the 1-MCP released into the headspace of the bottles was greater for Batch Z (mean particle size 5.0 microns) than the same batch not subjected to the described milling step, Batch Y (mean particle size 46.2 microns).

Example 4

Four batches of alpha-cyclodextrin complex of 1-methylcyclopropene (HAIP, obtained from AgroFresh Solutions), Batch i, Batch ii, Batch iii, and Batch iv were taken. Batches iii and iv had been pre-milled to a smaller particle size. Each of the four batches was measured for particle size distribution by laser-diffraction analysis using a Horiba LA-950 particle size analyzer. Particle size results are given in TABLE 4:

TABLE 4

| Alpha-cyclodextrin/1-MCP complex particle size results | | | | | |
|---|---|---|---|---|---|
| | | Batch i | Batch ii | Batch iii | Batch iv |
| Mean particle size (µm) | | 50.5 | 44.9 | 7.2 | 5.4 |
| Diameter on cumulative % (µm) | D10 | 8.9 | 11.5 | 2.9 | 2.4 |
| | D50 | 30.9 | 43.2 | 6.3 | 4.7 |
| | D90 | 100.9 | 98.6 | 12.6 | 9.4 |

Example 5

Two substrates, polyethylene terephthalate (PET) (SKYROL® SM 30, 75 gauge, from SKC Inc.) and polypropylene (PP) (Q00061, 100 gauge from Profol Kunststoffe GmbH), were used to prepare four plastic pouches from each substrate as follows. Four 4-inch by 8-inch (10.16 cm by 20.32 cm) sheets were cut from each substrate. Each sheet was folded in half so that the resulting folded substrate was four inches by four inches (10.16 cm by 10.16 cm). Two edges of each folded substrate were heat-sealed using a heat sealer (H-1254 from Uline) to form a pouch with an open end.

A known weight of each of the four HAIP Batches i-iv of Example 4 was placed in each of the four open-ended polypropylene pouches. A known weight of each of the four HAIP Batches i-iv was further placed in each of the four open-ended polyester pouches. The open ends of all eight open-ended pouches were heat-sealed using a heat sealer (H-1254 from Uline) to provide eight sealed pouches, as shown in TABLE 5.

TABLE 5

Measured weight of HAIP in sealed pouches

| Sealed pouch | Batch of alpha-cyclodextrin/ 1-MCP HAIP complex | Substrate | Weight of HAIP in pouch (grams) |
|---|---|---|---|
| P7 | i | PET | 0.0997 |
| P8 | ii | | 0.1010 |
| P9 | iii | | 0.1003 |
| P10 | iv | | 0.1009 |
| P11 | i | PP | 0.0504 |
| P12 | ii | | 0.0497 |
| P13 | iii | | 0.0504 |
| P14 | iv | | 0.0504 |

Example 6

Each of pouches P7 to P14 was rolled up and inserted into a 250 mL glass Boston round bottle. One mL of deionized water was injected into each bottle with care taken to avoid injection of water directly onto the pouch. After injection of the water, each bottle was immediately sealed with a TEFLON®-faced silicone rubber septum. For each bottle, 1-MCP in the headspace was measured by removing a 250 μL sample of the headspace gas. A gas sample was removed at one hour, two hours, four hours, eight hours, 24 hours, 49 hours, and 172 hours after the water injection.

The 1-MCP was measured in each gas sample by removing the 250 μL sample of headspace gas using the method described above in General Procedures. Employing this method, the amount of 1-MCP released (measured as μL/L-volume/volume (v/v)) from each sealed pouch was obtained. It was noted that Pouch P12 had a pinhole. Accordingly, the data from Pouch P12 were not included. The remaining data are displayed in TABLE 6.

TABLE 6

Concentration of 1-MCP released into headspace as measured by GC in Example 6.

| Pouch | Weight of HAIP in pouch (grams) | 1-MCP concentration (ppm) in headspace | | | | | | |
|---|---|---|---|---|---|---|---|---|
| | | 1 hour | 2 hours | 4 hours | 8 hours | 24 hours | 49 hours | 172 hours |
| P7 | 0.0997 | 0.288 | 0.287 | 0.306 | 0.326 | 0.295 | 0.550 | 0.802 |
| P8 | 0.1010 | 0.396 | 0.582 | 0.720 | 0.710 | 0.705 | 0.886 | 1.338 |
| P9 | 0.1003 | 0.533 | 0.644 | 0.850 | 1.497 | 4.998 | 10.776 | 39.219 |
| P10 | 0.1009 | 3.307 | 4.446 | 5.623 | 8.469 | 25.975 | 52.703 | 159.8 |
| P11 | 0.0504 | 0.088 | 0.126 | 0.403 | 1.780 | 6.855 | 15.775 | 141.000 |
| P13 | 0.0504 | 0.000 | 0.000 | 0.616 | 5.661 | 31.099 | 70.128 | 220.760 |
| P14 | 0.0504 | 0.590 | 1.031 | 2.673 | 8.385 | 37.539 | 77.291 | 233.220 |

The concentrations of 1-MCP in TABLE 6 were normalized for the various weights of HAIP in each pouch by dividing the measured concentration (displayed in TABLE 6) by the weight of the HAIP in the pouch (in grams): The results are displayed in TABLE 7.

TABLE 7

Normalized concentrations of 1-MCP released into headspace, converted from the data of TABLE 6.

| Pouch | Pouch material | Mean particle size (μm) | 1-MCP concentration (ppm) in headspace per gram of HAIP | | | | | | |
|---|---|---|---|---|---|---|---|---|---|
| | | | 1 hour | 2 hours | 4 hours | 8 hours | 24 hours | 49 hours | 172 hours |
| P7 | PET | 50.5 | 2.89 | 2.88 | 3.07 | 3.27 | 2.96 | 5.52 | 8.04 |
| P8 | PET | 44.9 | 3.92 | 5.76 | 7.13 | 7.03 | 6.98 | 8.77 | 13.25 |
| P9 | PET | 7.2 | 5.31 | 6.42 | 8.47 | 14.93 | 49.83 | 107.44 | 391.02 |
| P10 | PET | 5.4 | 32.78 | 44.06 | 55.73 | 83.93 | 257.43 | 522.33 | 1583.8 |
| P11 | PP | 50.5 | 1.75 | 2.50 | 8.00 | 35.32 | 136.01 | 313.00 | 2797.6 |
| P13 | PP | 7.7 | 0 | 0 | 12.22 | 112.32 | 617.04 | 1391.4 | 4380.2 |
| P14 | PP | 5.4 | 11.71 | 20.46 | 53.04 | 166.4 | 744.82 | 1533.6 | 4627.4 |

Figure 4:
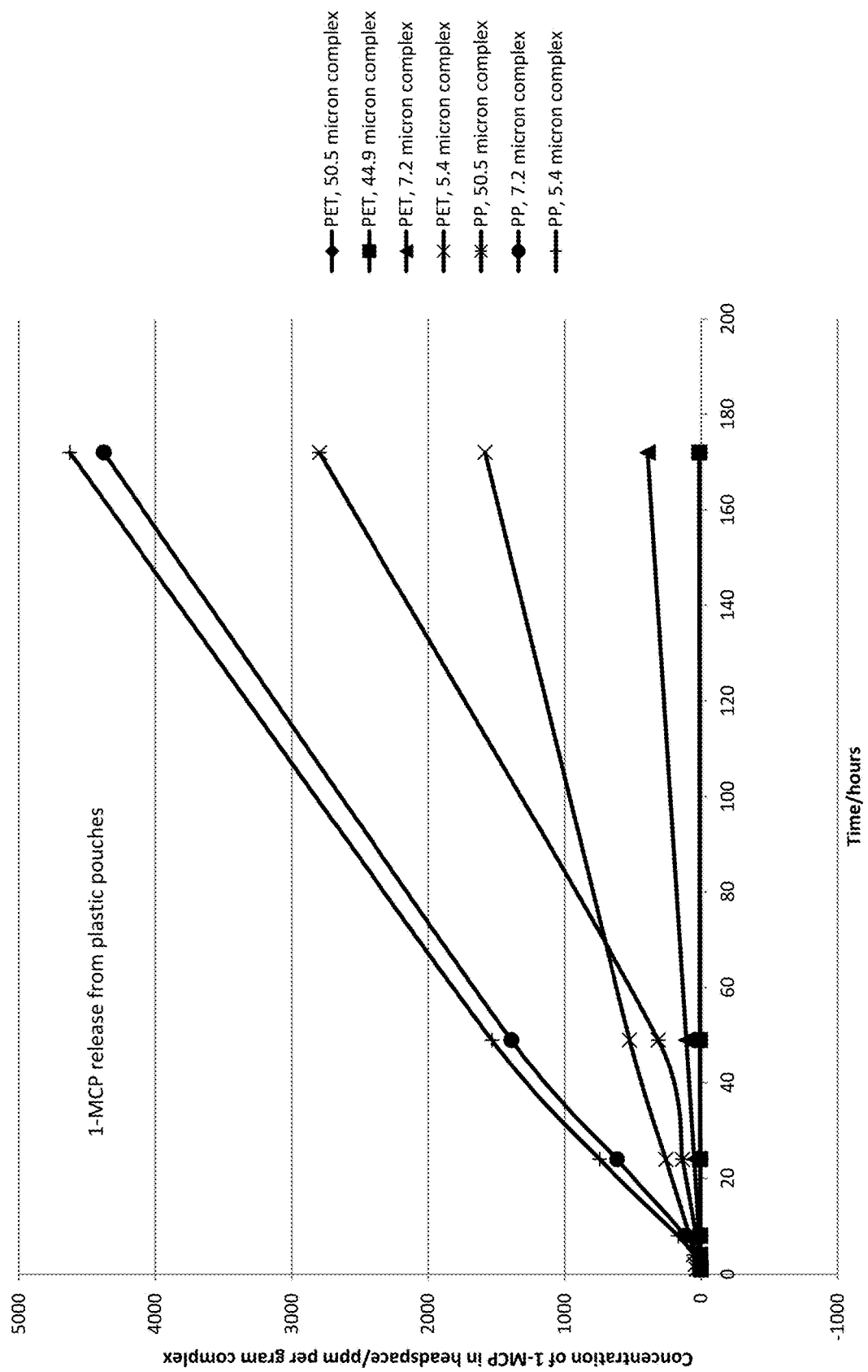
FIG. 4 is a plot of 1-MCP concentration in a headspace as a function of time, in accordance with the procedure of Example 6.

In FIG. 4, the 1-MCP concentration (volume/volume) from each pouch into the headspace is plotted against time after water injection.

The concentration of the 1-MCP (normalized for weight of complex) released into the headspace was greater from the polypropylene pouches than from the polyester pouches.

With a given pouch material, the concentration of the 1-MCP (normalized for weight of complex) released into the headspace was greater the smaller the measured particle size of the complex.

Example 7

Four batches of alpha-cyclodextrin complex of 1-methylcyclopropene (HAIP, obtained from AgroFresh Solutions), Batch v, Batch vi, Batch vii, and Batch viii were taken. Batches v, vii, and viii had been pre-milled to a smaller particle size. Batch vi was the same batch as Batch ii in Examples 4-6. Batch vii was the same batch as Batch iv in Examples 4-6.

In addition, a blend, Batch ix, was obtained by combining a sample of Batch v and a sample of Batch vi in a 1:1 ratio by weight.

Each of the five batches was measured for particle size distribution by laser-diffraction analysis using a Horiba LA-950 particle size analyzer. Particle size results are given in TABLE 8.

TABLE 8

Particle size analysis of alpha-cyclodextrin/1-MCP complex

|  | Batch v | Batch vi | Batch vii | Batch viii | Batch ix |
|---|---|---|---|---|---|
| Mean size (μm) | 6.8 | 44.9 | 5.4 | 6.2 | 20.2 |
| Median size (μm) | 6.2 | 30.9 | 4.7 | 5.3 | 11.8 |

TABLE 8-continued

Particle size analysis of alpha-cyclodextrin/1-MCP complex

|  |  | Batch v | Batch vi | Batch vii | Batch viii | Batch ix |
|---|---|---|---|---|---|---|
| Standard deviation (μm) | | 3.3 | 41.8 | 3.0 | 3.7 | 22.6 |
| Mode size (μm) | | 7.1 | 27.3 | 4.8 | 5.5 | 12.4 |
| Specific surface area ($cm^2/cm^3$) | | 11413 | 3485.9 | 14543 | 13405 | 7548 |
| Diameter on cumulative % (μm) | D05 | 2.5 | 4.7 | 2.0 | 2.0 | 2.6 |
| | D10 | 3.1 | 8.9 | 2.4 | 2.5 | 3.5 |
| | D50 | 6.2 | 30.9 | 4.7 | 5.3 | 11.8 |
| | D90 | 11.3 | 101.0 | 9.4 | 11.0 | 51.2 |
| | D99 | 16.5 | 200.3 | 15.6 | 18.9 | 108.4 |

Example 8: Analysis of Complex Batches for 1-MCP Release

Five samples of each of Batch v, Batch vi, Batch vii, and Batch viii of the complex from Example 7 were analyzed for 1-methylcyclopropene (1-MCP) content as follows: A sample of each batch was deposited into a separate 250 mL Boston round bottle. To each bottle was added 3 mL of water, and the bottle was immediately sealed with a PTFE-coated septum and phenolic septum cap. Each bottle was shaken for one hour, during which time the complex completely dissolved in the water. The headspace of each bottle was analyzed for 1-MCP concentration, c, in parts per million (μL/L).

The expected release of 1-MCP from Batch ix (1:1 combination by weight of complex from Batch v and complex from Batch vi was calculated from the average of Batch v and Batch vi. The results obtained are displayed in TABLE 9.

TABLE 9

Alpha-cyclodextrin/1-MCP complex 1-MCP release results

| Sample | Batch | Mean particle size (μm) | Sample weight (grams) | Measured concentration of 1-MCP ($\mu L \cdot L^{-1}$) | Concentration of 1-MCP normalized for release from 0.01 grams of complex ($\mu L \cdot L^{-1}$) | Mean release, c, per 0.01 grams of complex ($\mu L \cdot L^{-1}$) | Standard deviation ($\mu L \cdot L^{-1}$) |
|---|---|---|---|---|---|---|---|
| v.a | v | 6.8 | 0.0223 | 1892 | 848.4 | 832 | 11 |
| v.b | | | 0.0246 | 2035 | 828.9 | | |
| v.c | | | 0.0186 | 1525 | 819.9 | | |
| v.d | | | 0.0273 | 2254 | 825.6 | | |
| v.e | | | 0.0161 | 1347 | 836.6 | | |
| vi.a | vi | 44.9 | 0.0182 | 1400 | 769.2 | 787 | 10 |
| vi.b | | | 0.0154 | 1220 | 791.9 | | |
| vi.c | | | 0.0207 | 1629 | 787.0 | | |
| vi.d | | | 0.0191 | 1513 | 791.6 | | |
| vi.e | | | 0.0211 | 1679 | 795.8 | | |
| vii.a | vii | 5.4 | 0.0196 | 1384 | 706.1 | 707 | 3 |
| vii.b | | | 0.0226 | 1602 | 708.8 | | |
| vii.c | | | 0.0189 | 1343 | 710.6 | | |
| vii.d | | | 0.0196 | 1389 | 708.7 | | |
| vii.e | | | 0.0224 | 1572 | 701.6 | | |
| viii.a | viii | 6.2 | 0.0144 | 994.5 | 690.6 | 685 | 5 |
| viii.b | | | 0.0152 | 1028 | 676.4 | | |
| viii.c | | | 0.013 | 892.8 | 686.8 | | |
| viii.d | | | 0.0209 | 1433.4 | 685.8 | | |
| viii.e | | | 0.0171 | 1172 | 685.6 | | |
| | ix | 20.2 | | | | 810 | |

Example 9: Preparation of Coating Mixtures

An overprint varnish (OPV) comprised between 1% and 2% by weight water as measured by Karl Fisher analysis and comprised about 39.9 parts by weight of polyamide resin, about 0.2 parts by weight of ethyl acetate, about 2.8 parts by weight of heptane, about 21.2 parts by weight of ethanol, about 11.1 parts by weight of hydrotreated light naphtha (CAS number 64742-49-0), about 11.6 parts by weight of light aliphatic solvent naphtha (CAS number 64742-89-8), and about 13.3 parts by weight of propan-1-ol.

The overprint varnish (about 2.5 gallons) was dried using the procedure described above in General Procedures. The dried overprint varnish had a moisture content of less than 0.50 wt %.

The kinematic viscosity of the overprint varnish was adjusted before use as follows: A sample of the dried overprint varnish was tested using a #3 Zahn cup (available from Cole-Parmer, 795-104). If the effluent time exceeded 23 seconds, a small amount of diluent (described below) was added incrementally and mixed in until the dried overprint varnish had an effluent time of about 23 seconds (corresponding to a kinematic viscosity of about 250 centistokes). Between 10 ml and 100 ml of diluent was required per one gallon of overprint varnish, depending on batch and mixing conditions. The diluent comprised 80% propan-1-ol, 16% of hydrotreated light naphtha (CAS number 64742-49-0), and 4% heptane by weight.

The mean percent solids of the dried overprint varnish (adjusted as described above) was 45.94% by weight.

The overprint varnish was sealed in a pail with an airtight lid and left overnight.

Five batches of known weight of the dried adjusted overprint varnish were prepared as described; Batch 1, Batch 2, Batch 3, Batch 4, and Batch 5, each of which was sealed into a two-gallon bucket.

To each of Batches 1, 2, 3, 4, and 5 of dried overprint varnish was respectively added four parts by weight of one of Batches v, vi, vii, viii, and ix of alpha-cyclodextrin/1-MCP complex, as shown in TABLE 10. For every 96 parts by weight of the dried overprint varnish, 4 parts by weight of the alpha-cyclodextrin complex were added as follows: A two-gallon capacity bucket of the dried overprint varnish was mixed using a three-inch Cowles blade at 540 rpm (revolutions per minute). The alpha-cyclodextrin/1-MCP complex was slowly added to the dried overprint varnish being mixed. The mixture was tested for homogeneity by dipping a wooden tongue depressor into the mixture, removing the tongue depressor, and visually inspecting the mixture on the tongue depressor for agglomerations. Mixing was continued until the mixture was homogeneous, i.e. no large agglomerations were visible on the tongue depressor. The final mixture comprised about 48.1 percent solids including 4 weight percent of the complex. The final mixture was coated immediately following mixing.

TABLE 10

Coating mixtures of Example 9

| Coating composition | Batch number of complex | Batch of OPV | Wt % of complex | % solids | Mean particle size of complex (μm) |
|---|---|---|---|---|---|
| I | v | 1 | 4.0 | 48.1 | 6.8 |
| II | vi | 2 | | | 44.9 |
| III | vii | 3 | | | 5.4 |
| IV | viii | 4 | | | 6.2 |
| V | ix | 5 | | | 20.2 |

Example 10

Coating of each of Coating Compositions I, II, III, IV, and V was carried out on a flexographic press fitted with an anilox roll of 400 lines per inch and having a volume of 7.06 BCM (billions of cubic microns) and a 100% screen flexographic plate.

Coating was carried out at a web speed of about 200 feet per minute (61 meters per minute) onto a 75 gauge film substrate (0.75 thousands of an inch thick or 19 microns thick). The treated substrate was dried in line in an impingement oven of about six feet (1.83 meters) in length set at about 145° F. (63° C.) with a residence time of about two seconds.

Compositions I-IV were coated onto polyethylene terephthalate film. Composition V was coated onto clear coextruded oriented polypropylene film (T 523-3 available from Taghleef Industries).

Coatings were produced as shown in TABLE 11.

TABLE 11

Flexographic coatings of Example 10.

| Coating Roll | Coating Composition | Complex Batch | Mean particle size of complex (microns) |
|---|---|---|---|
| 1 | I | v | 6.8 |
| 2 | II | vi | 44.9 |
| 3 | III | vii | 5.4 |
| 4 | IV | viii | 6.2 |
| 5 | V | ix | 20.2 |

Example 11

Using a paper cutter, seven rectangular samples 4 inches by 12 inches (10.2 cm by 30.5 cm) were cut from each of coating Rolls 1, 2, 3, 4, and 5 from Example 10. One of the rectangular samples was labeled A, one B, one C, one D, one E, one F and one G. Each sample was individually placed in a 250 mL glass Boston round bottle. Then 50 μL of deionized water was injected into each bottle. Care was taken so that the liquid water did not directly contact the sample. Each bottle was then sealed with a TEFLON® faced silicone rubber septum. Then the concentration of 1-MCP was measured in the headspace at one, two, four, eight, and 24 hours after the injection of water into each bottle.

Employing this method, the amount of 1-MCP released (measured as μL/L-v/v) from the printed sheets is recorded in TABLE 12 below.

TABLE 12

Release of 1-MCP from Coating Samples at room temperature (at about 22° C.).

| Coating Roll | Sample | Complex Batch | Time after wafer-addition (hrs) | 1-MCP (ppm (uL/L)) |
|---|---|---|---|---|
| 1 | A | v | 1 | 103.9 |
| 1 | B | v | 1 | 105.7 |
| 1 | C | v | 1 | 126.7 |
| 1 | D | v | 1 | 105.4 |
| 1 | E | v | 1 | 112.6 |
| 1 | F | v | 1 | 106.6 |
| 1 | G | v | 1 | 114.0 |
| 2 | A | vi | 1 | 20.42 |
| 2 | B | vi | 1 | 24.90 |
| 2 | C | vi | 1 | 22.49 |
| 2 | D | vi | 1 | 24.59 |
| 2 | E | vi | 1 | 30.43 |
| 2 | F | vi | 1 | 25.38 |
| 2 | G | vi | 1 | 25.02 |
| 3 | A | vii | 1 | 114.2 |
| 3 | B | vii | 1 | 86.17 |
| 3 | C | vii | 1 | 93.65 |
| 3 | D | vii | 1 | 95.56 |
| 3 | E | vii | 1 | 90.39 |
| 3 | F | vii | 1 | 95.12 |
| 3 | G | vii | 1 | 73.31 |
| 4 | A | viii | 1 | 85.49 |
| 4 | B | viii | 1 | 79.38 |
| 4 | C | viii | 1 | 80.82 |
| 4 | D | viii | 1 | 74.95 |
| 4 | E | viii | 1 | 81.20 |
| 4 | F | viii | 1 | 68.43 |
| 4 | G | viii | 1 | 76.70 |
| 5 | A | ix | 1 | 75.72 |
| 5 | B | ix | 1 | 74.19 |
| 5 | C | ix | 1 | 74.38 |
| 5 | D | ix | 1 | 66.89 |
| 5 | E | ix | 1 | 59.94 |
| 5 | F | ix | 1 | 72.74 |
| 5 | G | ix | 1 | 65.56 |
| 1 | A | v | 2 | 163.8 |
| 1 | B | v | 2 | 174.4 |
| 1 | C | v | 2 | 192.4 |
| 1 | D | v | 2 | 180.9 |
| 1 | E | v | 2 | 161.0 |
| 1 | F | v | 2 | 179.5 |
| 1 | G | v | 2 | 178.4 |
| 2 | A | vi | 2 | 28.95 |
| 2 | B | vi | 2 | 31.68 |
| 2 | C | vi | 2 | 31.37 |
| 2 | D | vi | 2 | 32.90 |
| 2 | E | vi | 2 | 34.02 |
| 2 | F | vi | 2 | 32.90 |
| 2 | G | vi | 2 | 32.40 |
| 3 | A | vii | 2 | 144.2 |
| 3 | B | vii | 2 | 129.6 |
| 3 | C | vii | 2 | 142.2 |
| 3 | D | vii | 2 | 136.6 |
| 3 | E | vii | 2 | 141.8 |
| 3 | F | vii | 2 | 140.6 |
| 3 | G | vii | 2 | 116.2 |
| 4 | A | viii | 2 | 125.6 |
| 4 | B | viii | 2 | 122.2 |
| 4 | C | viii | 2 | 118.6 |
| 4 | D | viii | 2 | 116.9 |
| 4 | E | viii | 2 | 137.5 |
| 4 | F | viii | 2 | 111.2 |
| 4 | G | viii | 2 | 124.0 |
| 5 | A | ix | 2 | 103.6 |
| 5 | B | ix | 2 | 101.1 |
| 5 | C | ix | 2 | 112.5 |
| 5 | D | ix | 2 | 97.63 |
| 5 | E | ix | 2 | 93.30 |
| 5 | F | ix | 2 | 106.7 |
| 5 | G | ix | 2 | 106.9 |
| 1 | A | v | 4 | 207.9 |
| 1 | B | v | 4 | 230.9 |
| 1 | C | v | 4 | 240.2 |
| 1 | D | v | 4 | 239.1 |
| 1 | E | v | 4 | 198.9 |
| 1 | F | v | 4 | 234.1 |
| 1 | G | v | 4 | 221.9 |
| 2 | A | vi | 4 | 33.66 |
| 2 | B | vi | 4 | 36.68 |
| 2 | C | vi | 4 | 37.16 |
| 2 | D | vi | 4 | 37.23 |
| 2 | E | vi | 4 | 36.34 |
| 2 | F | vi | 4 | 36.80 |
| 2 | G | vi | 4 | 36.55 |
| 3 | A | vii | 4 | 179.9 |
| 3 | B | vii | 4 | 168.8 |
| 3 | C | vii | 4 | 189.5 |
| 3 | D | vii | 4 | 179.2 |
| 3 | E | vii | 4 | 191.2 |
| 3 | F | vii | 4 | 193.1 |
| 3 | G | vii | 4 | 165.2 |
| 4 | A | viii | 4 | 158.2 |
| 4 | B | viii | 4 | 161.3 |
| 4 | C | viii | 4 | 149.5 |
| 4 | D | viii | 4 | 150.5 |
| 4 | E | viii | 4 | 168.1 |
| 4 | F | viii | 4 | 143.6 |
| 4 | G | viii | 4 | 165.2 |
| 5 | A | ix | 4 | 118.9 |
| 5 | B | ix | 4 | 121.3 |
| 5 | C | ix | 4 | 126.4 |
| 5 | D | ix | 4 | 119.5 |
| 5 | E | ix | 4 | 116.7 |
| 5 | F | ix | 4 | 121.4 |
| 5 | G | ix | 4 | 126.0 |
| 1 | A | v | 8 | 236.9 |
| 1 | B | v | 8 | 247.6 |
| 1 | C | v | 8 | 249.9 |
| 1 | D | v | 8 | 248.0 |
| 1 | E | v | 8 | 227.0 |
| 1 | F | v | 8 | 249.0 |
| 1 | G | v | 8 | 242.1 |
| 2 | A | vi | 8 | 36.79 |
| 2 | B | vi | 8 | 38.86 |
| 2 | C | vi | 8 | 38.48 |
| 2 | D | vi | 8 | 37.70 |
| 2 | E | vi | 8 | 38.09 |
| 2 | F | vi | 8 | 37.98 |
| 2 | G | vi | 8 | 38.45 |
| 3 | A | vii | 8 | 200.9 |
| 3 | B | vii | 8 | 192.5 |
| 3 | C | vii | 8 | 211.6 |
| 3 | D | vii | 8 | 201.6 |
| 3 | E | vii | 8 | 211.5 |
| 3 | F | vii | 8 | 213.4 |
| 3 | G | vii | 8 | 193.1 |
| 4 | A | viii | 8 | 175.4 |
| 4 | B | viii | 8 | 182.0 |
| 4 | C | viii | 8 | 166.2 |
| 4 | D | viii | 8 | 174.7 |
| 4 | E | viii | 8 | 184.9 |
| 4 | F | viii | 8 | 164.4 |
| 4 | G | viii | 8 | 182.2 |
| 5 | A | ix | 8 | 124.0 |
| 5 | B | ix | 8 | 126.8 |
| 5 | C | ix | 8 | 127.7 |
| 5 | D | ix | 8 | 126.7 |
| 5 | E | ix | 8 | 125.2 |
| 5 | F | ix | 8 | 124.8 |
| 5 | G | ix | 8 | 127.2 |
| 1 | A | v | 24 | 247.5 |
| 1 | B | v | 24 | 245.6 |
| 1 | C | v | 24 | 244.9 |
| 1 | D | v | 24 | 243.6 |
| 1 | E | v | 24 | 244.3 |
| 1 | F | v | 24 | 246.6 |

TABLE 12-continued

Release of 1-MCP from Coating Samples at room temperature (at about 22° C.).

| Coating Roll | Sample | Complex Batch | Time after wafer-addition (hrs) | 1-MCP (ppm (uL/L)) |
|---|---|---|---|---|
| 1 | G | v | 24 | 246.7 |
| 2 | A | vi | 24 | 37.05 |
| 2 | B | vi | 24 | 38.71 |
| 2 | C | vi | 24 | 37.83 |
| 2 | D | vi | 24 | 37.07 |
| 2 | E | vi | 24 | 38.06 |
| 2 | F | vi | 24 | 37.61 |
| 2 | G | vi | 24 | 38.30 |
| 3 | A | vii | 24 | 213.3 |
| 3 | B | vii | 24 | 209.2 |
| 3 | C | vii | 24 | 215.8 |
| 3 | D | vii | 24 | 212.8 |

TABLE 12-continued

Release of 1-MCP from Coating Samples at room temperature (at about 22° C.).

| Coating Roll | Sample | Complex Batch | Time after wafer-addition (hrs) | 1-MCP (ppm (uL/L)) |
|---|---|---|---|---|
| 3 | E | vii | 24 | 215.7 |
| 3 | F | vii | 24 | 216.0 |
| 3 | G | vii | 24 | 210.9 |
| 4 | A | viii | 24 | 185.5 |
| 4 | B | viii | 24 | 187.5 |
| 4 | C | viii | 24 | 183.6 |
| 4 | D | viii | 24 | 185.7 |
| 4 | E | viii | 24 | 187.0 |
| 4 | F | viii | 24 | 179.9 |
| 4 | G | viii | 24 | 187.9 |
| 5 | A | ix | 24 | 120.1 |
| 5 | B | ix | 24 | 123.0 |
| 5 | C | ix | 24 | 124.6 |
| 5 | D | ix | 24 | 123.6 |
| 5 | E | ix | 24 | 122.4 |
| 5 | F | ix | 24 | 120.2 |
| 5 | G | ix | 24 | 123.4 |

The coating weight of the coating of Rolls 1, 2, 3, 4, and 5 was determined, and is reported in TABLE 13.

TABLE 13

Coating weights of Rolls 1 to 5

| | Coating Weight | |
|---|---|---|
| Roll | grams per square inch | grains per square meter |
| 1 | 0.000768 | 1.190 |
| 2 | 0.000823 | 1.276 |
| 3 | 0.000799 | 1.238 |
| 4 | 0.000726 | 1.125 |
| 5 | 0.000749 | 1.161 |

The mean release for each Coating Roll is set out in TABLE 14, with the standard deviation in parentheses and the coating weights. The value of c for each batch of complex was obtained in Example 8 and is set forth in TABLE 9.

TABLE 14

Average 1-MCP release from coatings at room temperature (about 22° C.).

| Coating Roll | Coating weight, C (g·m$^{-2}$) | Mean release c of 1-MCP per 0.01 g of complex (μL/L) | Mean particle size of complex (μm) | 1 hour | 2 hours | 4 hours | 8 hours | 24 hours |
|---|---|---|---|---|---|---|---|---|
| | | | | Average 1-MCP Release (μL/L) (Standard deviation (ppm) in parentheses) | | | | |
| 1 | 1.190 | 832 | 6.8 | 110.7 (8.0) | 175.8 (10.7) | 224.7 (16.0) | 242.9 (8.4) | 245.6 (1.4) |
| 2 | 1.276 | 787 | 44.9 | 24.75 (3.07) | 32.03 (1.62) | 36.35 (1.23) | 38.05 (0.67) | 37.81 (0.61) |
| 3 | 1.238 | 707 | 5.4 | 92.62 (12.25) | 135.9 (10.0) | 181.0 (11.0) | 203.5 (8.8) | 213.4 (2.6) |
| 4 | 1.125 | 685 | 6.2 | 78.14 (5.46) | 122.3 (8.3) | 156.6 (9.0) | 175.7 (8.0) | 185.3 (2.8) |
| 5 | 1.161 | 810 | 20.2 | 69.92 (5.88) | 103.1 (6.4) | 121.5 (3.6) | 126.1 (1.4) | 122.5 (1.7) |

The amount of the complex in each 12×4 inch sample in TABLE 12 was calculated from the coating formulation and the coating weight reported in TABLE 13. From the amount of 1-MCP released by each batch of complex (reported in TABLE 9), the amount of 1-MCP released from the coatings compared with the theoretical amount of 1-MCP expected from the amount of the complex present in the coatings could be calculated. In order to calculate the theoretical release of the 1-MCP, the following calculations were used.

One 12 inch by 4 inch sample (48 square inches, or 0.03097 square meters) of coated roll gave rise to the released 1-MCP. If the coating weight (in g/m$^2$) is C, then the weight (M) of coating (in grams) giving rise to the 1-MCP release (from the 12×4 inch sample is given by M=0.03097·C. The weight of complex (W) in this portion of coating (in grams) is given by W=4.0M/(44.1+4.0), therefore W=4*0.03097C/48.1, therefore W=0.002575C.

The theoretical amount (E in microliters per liter) of 1-MCP release based on the amount of the complex in a 0.03097 square meter sample (assuming the complex has not lost any 1-MCP during processing and coating) is given by E=W·c/0.01, therefore E=0.002575C·c/0.01, therefore E=0.2575C·c Accordingly, E values for each coating roll can be calculated. These are set forth with associated data from TABLE 14 in TABLE 15.

TABLE 15

Theoretical amounts of 1-MCP release from 12 × 4 inch coating samples, based on yield of 1-MCP in TABLE 9.

| Coating Roll | Coating weight C (g·m$^{-2}$) | Complex c value (µL/L) | E (µL/L) | Mean particle size of complex (µm) | 1 hour | 2 hours | 4 hours | 8 hours | 24 hours |
|---|---|---|---|---|---|---|---|---|---|
| | | | | | Average 1-MCP Release (µL/L) (Standard deviation (ppm) in parentheses) | | | | |
| 1 | 1.190 | 832 | 254.9 | 6.8  | 110.7 (8.0)   | 175.8 (10.7) | 224.7 (16.0) | 242.9 (8.4)  | 245.6 (1.4) |
| 2 | 1.276 | 787 | 258.6 | 44.9 | 24.75 (3.07)  | 32.03 (1.62) | 36.35 (1.23) | 38.05 (0.67) | 37.81 (0.61) |
| 3 | 1.238 | 707 | 225.4 | 5.4  | 92.62 (12.25) | 135.9 (10.0) | 181.0 (11.0) | 203.5 (8.9)  | 213.4 (2.6) |
| 4 | 1.125 | 685 | 198.4 | 6.2  | 78.14 (5.46)  | 122.3 (8.3)  | 156.6 (9.0)  | 175.7 (8.0)  | 185.3 (2.8) |
| 5 | 1.161 | 810 | 242.2 | 20.2 | 69.92 (5.88)  | 103.1 (6.4)  | 121.5 (3.6)  | 126.1 (1.4)  | 122.5 (1.7) |

Finally, the mean percent of the expected release of 1-MCP actually achieved by the coatings, T, is given by multiplying the actual release values by 100/E. The values of T are set forth accordingly in TABLE 16.

TABLE 16

Percent expected 1-MCP release (at about 22° C.) from Coating Rolls 1-5.

| Coating Roll | Complex mean particle size (µm) | 1 hour | 2 hours | 4 hours | 8 hours | 24 hours |
|---|---|---|---|---|---|---|
| | | T (%) (Percent of expected 1-MCP actually released) | | | | |
| 1 | 6.8  | 43.4 | 69.0 | 88.2 | 95.3 | 96.3 |
| 2 | 44.9 | 9.6  | 12.4 | 14.1 | 14.7 | 14.6 |
| 3 | 5.4  | 38.1 | 55.8 | 74.4 | 83.6 | 87.7 |
| 4 | 6.2  | 39.4 | 61.6 | 79.1 | 88.5 | 93.4 |
| 5 | 20.2 | 28.9 | 42.6 | 50.2 | 52.1 | 50.6 |

Figure 5:
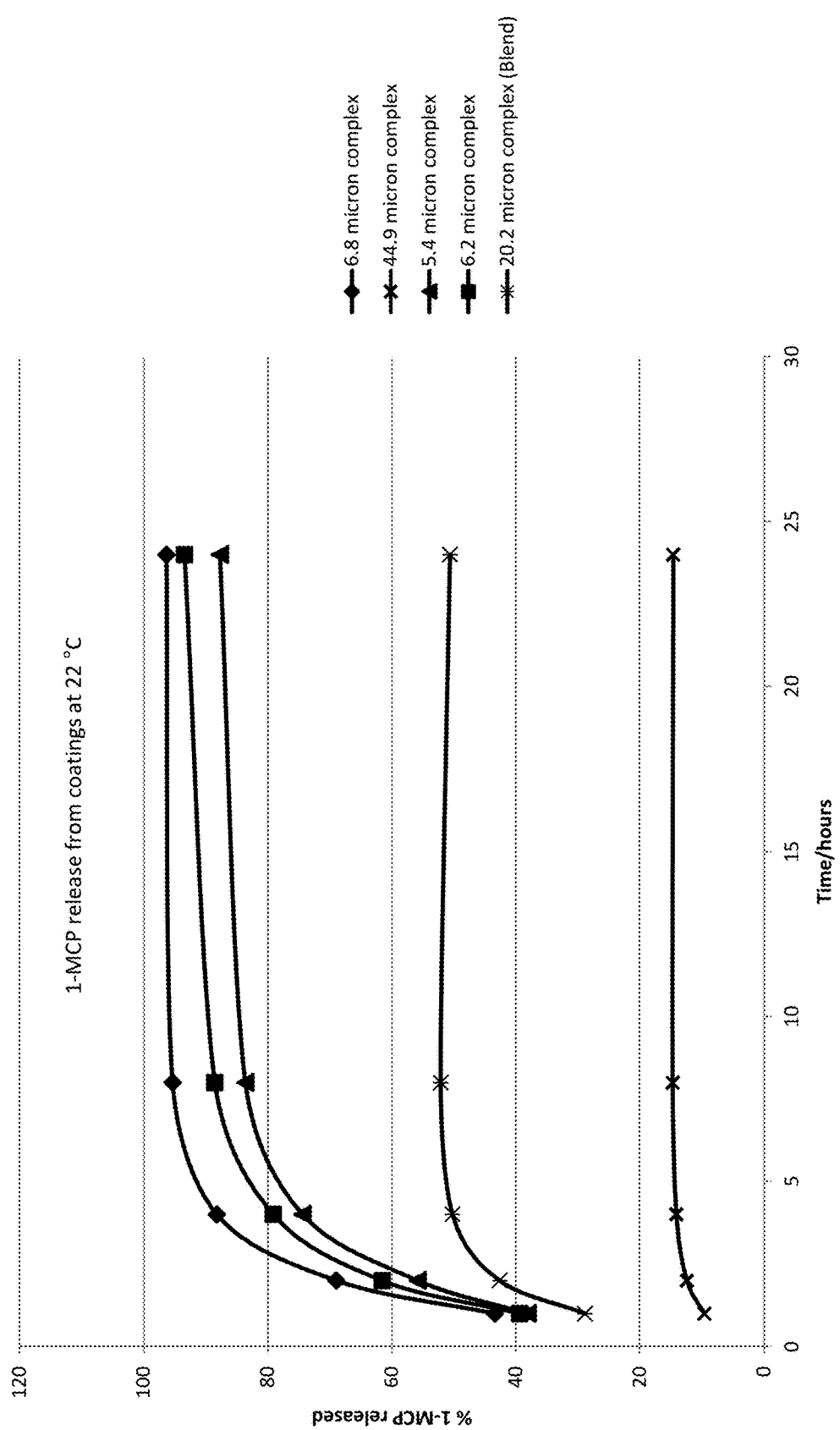
FIG. 5 is a plot of percent 1-MCP released into a headspace as a function of time, in accordance with the procedure of Example 11.

The data in TABLE 16 provide comparative data to show the effect of particle size on the amount of 1-MCP released normalized for coating weight variation and different amounts of 1-MCP per batch of complex. The data are plotted in FIG. 5.

At any given time after exposure to water, the percent expected release of 1-MCP from coatings made from cyclodextrin/1-MCP complex having mean particle size of about 5-7 microns was greater than the percent expected release from those coatings made from complex of mean particle size of about 20 microns, which in turn was greater than the percent expected release from those coatings made from complex of mean particle size of about 45 microns.

Example 12

Using a paper cutter, seven rectangular samples A-G of 4 inches by 12 inches (10.2 cm by 30.5 cm) were cut from each of coating Rolls 1, 2, 3, 4, and 5 from Example 10.

Each sample was stored at 2° C. for about 48 hours. Each sample was individually placed in a 250 mL glass Boston round bottle that had been pre-chilled to 2° C. Then 50 µL of deionized water that had been pre-chilled to 2° C. was injected into each bottle. Care was taken so that the liquid water did not directly contact the sample. Each bottle was then sealed with a TEFLON® faced silicone rubber septum and the bottle was returned to storage at 2° C. The concentration of 1-MCP was measured in the headspace at one, two, four, eight, and 24 hours after the injection of water into each bottle. The bottles were kept at 2° C. over this time. The concentration of the 1-MCP in the headspace gas was measured. The amount of 1-MCP released (measured as µL/L-v/v) from the printed sheets is recorded in TABLE 17 below.

TABLE 17

Release of 1-MCP from Coating Samples at 2° C.

| Coating Roll | Sample | Complex Batch | Time after water-addition (hrs) | 1-MCP Release at 2° C. (ppm (uL/L)) |
|---|---|---|---|---|
| 1 | A | v    | 1 | 39.35 |
| 1 | B | v    | 1 | 20.72 |
| 1 | C | v    | 1 | 39.75 |
| 1 | D | v    | 1 | 29.95 |
| 1 | E | v    | 1 | 36.36 |
| 1 | F | v    | 1 | 32.17 |
| 1 | G | v    | 1 | 42.48 |
| 2 | A | vi   | 1 | 8.499 |
| 2 | B | vi   | 1 | 7.777 |
| 2 | C | vi   | 1 | 8.726 |
| 2 | D | vi   | 1 | 9.563 |
| 2 | E | vi   | 1 | 5.278 |
| 2 | F | vi   | 1 | 13.16 |
| 2 | G | vi   | 1 | 10.96 |
| 3 | A | vii  | 1 | 22.41 |
| 3 | S | vii  | 1 | 35.33 |
| 3 | C | vii  | 1 | 28.18 |
| 3 | D | vii  | 1 | 26.87 |
| 3 | E | vii  | 1 | 31.11 |
| 3 | A | vii  | 2 | 34.43 |
| 3 | B | vii  | 2 | 45.82 |
| 3 | C | vii  | 2 | 36.97 |
| 3 | D | vii  | 2 | 34.94 |
| 3 | E | vii  | 2 | 36.53 |
| 3 | F | vii  | 2 | 34.13 |
| 3 | G | vii  | 2 | 23.10 |
| 4 | A | viii | 2 | 32.92 |
| 4 | B | viii | 2 | 31.79 |
| 4 | C | viii | 2 | 31.87 |
| 4 | D | viii | 2 | 34.60 |
| 4 | E | viii | 2 | 39.33 |
| 4 | F | viii | 2 | 22.07 |
| 4 | G | viii | 2 | 36.11 |
| 5 | A | ix   | 2 | 23.95 |
| 5 | B | ix   | 2 | 22.10 |
| 5 | C | ix   | 2 | 17.49 |
| 5 | D | ix   | 2 | 18.59 |
| 5 | E | ix   | 2 | 36.45 |
| 5 | F | ix   | 2 | 17.30 |
| 5 | G | ix   | 2 | 22.84 |
| 1 | A | v    | 4 | 87.40 |
| 1 | B | v    | 4 | 70.30 |
| 1 | C | v    | 4 | 91.02 |
| 1 | D | v    | 4 | 82.47 |
| 1 | E | v    | 4 | 84.76 |
| 1 | F | v    | 4 | 72.80 |
| 1 | G | v    | 4 | 75.18 |
| 2 | A | vi   | 4 | 14.89 |
| 2 | B | vi   | 4 | 18.77 |
| 2 | C | vi   | 4 | 17.32 |
| 2 | D | vi   | 4 | 17.57 |
| 2 | E | vi   | 4 | 12.63 |
| 2 | F | vi   | 4 | 20.31 |
| 2 | G | vi   | 4 | 19.66 |

TABLE 17-continued

Release of 1-MCP from Coating Samples at 2° C.

| Coating Roll | Sample | Complex Batch | Time after water-addition (hrs) | 1-MCP Release at 2° C. (ppm (uL/L)) |
|---|---|---|---|---|
| 3 | A | vii | 4 | 50.83 |
| 3 | B | vii | 4 | 61.22 |
| 3 | C | vii | 4 | 59.95 |
| 3 | D | vii | 4 | 56.70 |
| 3 | E | vii | 4 | 66.08 |
| 3 | F | vii | 4 | 52.19 |
| 3 | G | vii | 4 | 42.12 |
| 4 | A | viii | 4 | 50.45 |
| 4 | B | viii | 4 | 46.96 |
| 4 | C | viii | 4 | 54.33 |
| 4 | D | viii | 4 | 43.38 |
| 4 | E | viii | 4 | 51.45 |
| 4 | F | viii | 4 | — |
| 4 | G | viii | 4 | 43.91 |
| 5 | A | ix | 4 | 41.38 |
| 5 | B | ix | 4 | 34.11 |
| 5 | C | ix | 4 | 27.65 |
| 5 | D | ix | 4 | 29.64 |
| 5 | E | ix | 4 | 41.47 |
| 5 | F | ix | 4 | 23.73 |
| 5 | G | ix | 4 | 26.95 |
| 1 | A | v | 8 | 95.16 |
| 1 | B | v | 8 | 96.56 |
| 1 | C | v | 8 | 108.0 |
| 1 | D | v | 8 | 100.1 |
| 1 | E | v | 8 | 103.0 |
| 1 | F | v | 8 | 83.86 |
| 1 | G | v | 8 | 82.32 |
| 2 | A | vi | 8 | 16.07 |
| 2 | B | vi | 8 | 21.90 |
| 2 | C | vi | 8 | 18.65 |
| 2 | D | vi | 8 | 18.14 |
| 2 | E | vi | 8 | 15.65 |
| 2 | F | vi | 8 | 21.54 |
| 2 | G | vi | 8 | 22.96 |
| 3 | A | vii | 8 | 57.06 |
| 3 | B | vii | 8 | 61.87 |
| 3 | C | vii | 8 | 60.50 |
| 3 | D | vii | 8 | 56.85 |
| 3 | E | vii | 8 | 65.67 |
| 3 | F | vii | 8 | 52.66 |
| 3 | G | vii | 8 | 49.60 |
| 4 | A | viii | 8 | 52.87 |
| 4 | B | viii | 8 | 57.83 |
| 4 | C | viii | 8 | 60.71 |
| 4 | D | viii | 8 | 57.36 |
| 4 | E | viii | 8 | 63.26 |
| 4 | F | viii | 8 | 61.55 |
| 4 | G | viii | 8 | 56.26 |
| 5 | A | ix | 8 | 48.02 |
| 5 | B | ix | 8 | 40.50 |
| 5 | C | ix | 8 | 35.24 |
| 5 | D | ix | 8 | 38.17 |
| 5 | E | ix | 8 | 45.85 |
| 5 | F | ix | 8 | 28.72 |
| 5 | G | ix | 8 | 34.27 |
| 1 | A | v | 24 | 116.0 |
| 1 | B | v | 24 | 118.6 |
| 1 | C | v | 24 | 131.6 |
| 1 | D | v | 24 | 129.2 |
| 1 | E | v | 24 | 120.6 |
| 1 | F | v | 24 | 102.1 |
| 1 | G | v | 24 | 99.60 |
| 2 | A | vi | 24 | 20.12 |
| 2 | B | vi | 24 | 22.62 |
| 2 | C | vi | 24 | 22.56 |
| 2 | D | vi | 24 | 21.94 |
| 2 | E | vi | 24 | 19.60 |
| 2 | F | vi | 24 | 23.57 |
| 2 | G | vi | 24 | 25.01 |
| 3 | A | vii | 24 | 71.63 |
| 3 | B | vii | 24 | 63.16 |
| 3 | C | vii | 24 | 76.54 |
| 3 | D | vii | 24 | 56.82 |
| 3 | E | vii | 24 | 69.58 |
| 3 | F | vii | 24 | 55.24 |
| 3 | G | vii | 24 | 61.51 |
| 4 | A | viii | 24 | 61.80 |
| 4 | B | viii | 24 | 59.82 |
| 4 | C | viii | 24 | 59.69 |
| 4 | D | viii | 24 | 60.82 |
| 4 | E | viii | 24 | 66.51 |
| 4 | F | viii | 24 | 62.76 |
| 4 | G | viii | 24 | 54.43 |
| 5 | A | ix | 24 | 65.93 |
| 5 | B | ix | 24 | 50.90 |
| 5 | C | ix | 24 | 45.39 |
| 5 | D | ix | 24 | 44.41 |
| 5 | E | ix | 24 | 51.02 |
| 5 | F | ix | 24 | 36.77 |
| 5 | G | ix | 24 | 40.50 |

From the values in TABLE 17 were calculated the expected (E) values, which latter values are set forth in TABLE 18. The calculations were done using the methods set forth in Example 11.

TABLE 18

Average 1-MCP release from coatings at 2° C.

| Coating Roll | Coating weight (g·m$^{-2}$) | Complex c value (μL/L) | E (μL/L) | Complex mean particle size (μm) | 1 hour | 2 hours | 4 hours | 8 hours | 24 hours |
|---|---|---|---|---|---|---|---|---|---|
| | | | | | \multicolumn{5}{c}{Average 1-MCP Release/ppm (Standard deviation/ppm in parentheses)} |
| 1 | 1.190 | 832 | 254.9 | 6.8 | 34.40 (7.46) | 56.92 (9.92) | 80.56 (7.88) | 95.57 (9.52) | 116.82 (12.27) |
| 2 | 1.276 | 787 | 258.6 | 44.9 | 9.14 (2.48) | 12.65 (2.52) | 17.31 (2.72) | 19.27 (2.91) | 22.20 (1.88) |
| 3 | 1.238 | 707 | 225.4 | 5.4 | 27.15 (5.78) | 35.13 (6.66) | 55.58 (7.93) | 57.74 (5.49) | 64.93 (7.91) |
| 4 | 1.125 | 685 | 198.4 | 6.2 | 21.18 (6.34) | 32.67 (5.38) | 48.41 (4.38) | 58.55 (3.54) | 60.83 (3.66) |
| 5 | 1.161 | 810 | 242.2 | 20.2 | 12.27 (8.45) | 22.67 (6.64) | 32.13 (7.08) | 38.68 (6.74) | 47.84 (9.49) |

Finally, from the values in TABLE 18 were calculated the T values, which latter are set forth in TABLE 19. The calculations were done using the methods set forth in Example 11.

TABLE 19

Percent theoretical 1-MCP release (2° C. measurements)

| Coating Roll | Complex mean particle size/μm | 1 hour | 2 hours | 4 hours T (%) (Percent of expected 1-MCP actually released) | 8 hours | 24 hours |
|---|---|---|---|---|---|---|
| 1 | 6.8 | 13.5 | 22.3 | 31.6 | 37.5 | 45.8 |
| 2 | 44.9 | 3.5 | 4.8 | 6.7 | 7.5 | 8.6 |
| 3 | 5.4 | 12.0 | 15.6 | 24.7 | 25.6 | 28.8 |
| 4 | 6.2 | 10.7 | 16.5 | 24.4 | 29.5 | 30.7 |
| 5 | 20.2 | 5.1 | 9.4 | 13.3 | 16.0 | 19.8 |

Figure 6:
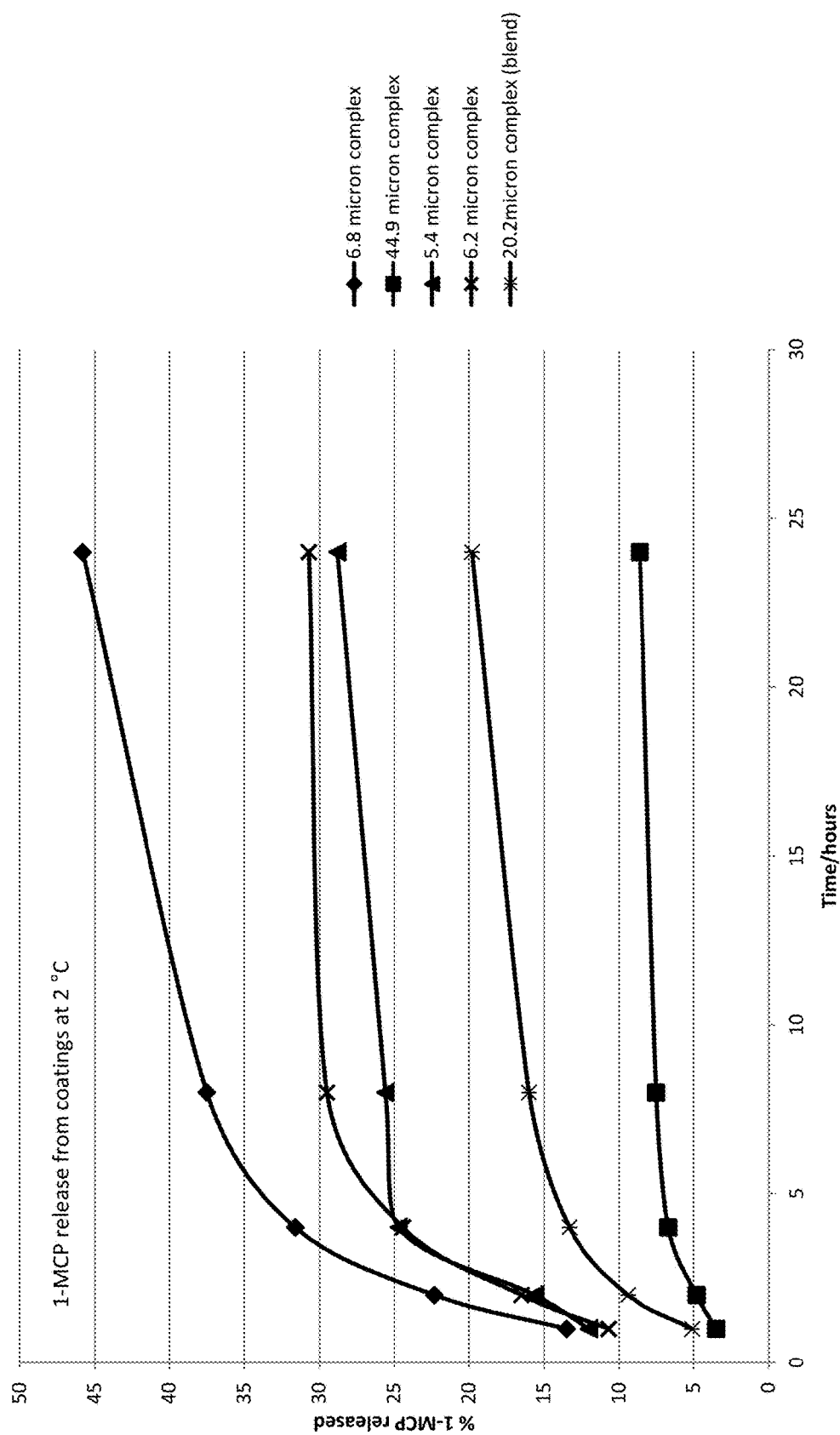
FIG. 6 is a plot of percent 1-MCP released into a headspace as a function of time, in accordance with the procedure of Example 12.

The data in TABLE 19 provide comparative data to show the effect of particle size on the amount of 1-MCP released at 2° C., where the release is normalized for coating weight variation and different amounts of 1-MCP per batch of complex. The data are plotted in FIG. 6.

At any given time after exposure to water, the percent expected release of 1-MCP from coatings made from cyclodextrin/1-MCP complex having mean particle size of about 5-7 microns was greater than the percent expected release from those coatings made from complex of mean particle size of about 20 microns, which in turn was greater than the percent expected release from those coatings made from complex of mean particle size of about 45 microns.

Example 13

Each of five petrolatum compositions, Compositions VI, VII, VIII, IX, and X, is formed by immersing a container having a known weight of petrolatum (VASELINE®, melting point 38-56° C., obtained from Sigma Aldrich Corporation of St. Louis, Mo.) in a water bath at 70° C. until liquefied, and mechanically dispersing 4 wt % of an alpha-cyclodextrin complex of 1-methylcyclopropene (HAIP, obtained from AgroFresh Solutions) into the liquefied petrolatum using low shear mixing. As shown in TABLE 20, each composition is made with a different batch of complex, and each of the five petrolatum-based cyclodextrin compositions is individually applied to a continuously moving flexible web using flexographic printing methodology to produce five treated laminates as described below. The batches of complex used are the same as those described in Examples 7 and 8.

TABLE 20

Petrolatum coatings

| Treated Laminate | Petrolatum Composition | Complex Batch | Mean particle size of complex (microns) | Mean release, c, per 0.01 grams of complex (μL-L$^{-1}$) |
|---|---|---|---|---|
| 6 | VI | v | 6.8 | 832 |
| 7 | VII | vi | 44.9 | 787 |
| 8 | VIII | vii | 5.4 | 707 |
| 9 | IX | viii | 6.2 | 685 |
| 10 | X | ix | 20.2 | 810 |

Flexographic printing is carried out using a narrow web rotary printing press (340 mm wide flexographic press obtained from Gallus Inc. of Philadelphia, Pa.). Flexible plates made of engineered photopolymer and having a raised discontinuous diamond relief pattern covering 40% of the plate surface area are adhered to the plate cylinder. The film substrate used for printing is a high barrier film (EXXON MOBIL® BICOR® 210 ASB-X, acrylic and polyvinyldene chloride coated oriented polypropylene, 33 cm wide, obtained from the EXXON MOBIL® Corporation of Irving, Tex.). The fountain trough is loaded with one of the petrolatum compositions, Composition VI, VII, VIII, IX, or X. Hot air is blown over the fountain roll to keep the petrolatum composition liquefied. The liquefied petrolatum composition is applied to the photopolymer plate using an anilox roll. The printing press is run at 100 to 150 ft/min (30.5 to 45.7 m/min). The printed petrolatum composition is then 'hard-set' using a chill roll filled with dry ice pellets. Then the entire web surface is coated inline with a UV lamination adhesive (RAAL00160/1060DHV UV/EB Curable Adhesive, obtained from ACTEGA WIT, Inc. of Lincolnton, N.C.) coated via flexographic printing, using a 500 lines/in (197 lines/cm, 5.02 bcm) anilox roll before joining a second substrate to the adhesive. The second substrate is a 1 mil (25.4 μm) thick, low density polyethylene (LDPE) web (MI=1.8 g/10 min, density 0.921 g/ml, Vicat softening point 100° C.) which is applied at a nip, and radiation curing of the adhesive is carried out using UV lamps mounted immediately after the nip point to prevent separation or air pockets in the laminated film. Curing is accomplished with a 300 watt/inch lamp. The completed Treated Laminate Roll, a treated laminate containing one of Compositions VI, VII, VIII, IX, or X printed in a diamond pattern, is wound up.

In this manner, each of Petrolatum Compositions VI, VII, VIII, IX, and X is disposed between the two substrate layers of Treated Laminates 6, 7, 8, 9, and 10 respectively, wherein direct substrate-adhesive-substrate contact in the interstitial areas provided by the diamond pattern effectively isolates the Petrolatum Composition into "islands". The isolated islands of the cyclodextrin composition provide for ease of windup, storage, and use. Further, when placed in a container having an item of produce also contained therein, the Petrolatum Composition will not contact the produce directly. No petrolatum can contact with the packaged food, and no petrolatum migration is possible.

Three 10 cm×30.5 cm rectangular samples are cut from each of Treated Laminates 6-10. Each sample is loosely rolled up and placed into a separate clean 250 mL bottle for testing according to the analytical test method used in Example 11. Each bottle is injected with 50 μL of deionized water. Care is taken so that the liquid water does not directly contact the film. Bottle headspace is analyzed for 1-MCP at four time periods; 2, 22, 44, and 72 hours after the injection of water. The average headspace concentration of 1-MCP for each of the three samples is tabulated in TABLE 21.

Mean particle sizes were measured in Example 7 and mean release per 0.01 g of complex (c) was measured in Example 8.

TABLE 21

1-MCP release from petrolatum treated laminate samples

| Treated laminate | Average amount of 1-MCP released, average three samples after t hours (μL/L) | | | | Batch of complex | Mean release, c, per 0.01 g of complex (μL/L) | Meas particle size of complex (microns) |
|---|---|---|---|---|---|---|---|
| | t = 2 hours | t = 22 hours | t = 44 hours | t = 72 hours | | | |
| 6 | 3.2 | 116.4 | 135.1 | 133.7 | v | 832 | 6.8 |
| 7 | 0.5 | 16.7 | 19.4 | 19.2 | vi | 787 | 44.9 |
| 8 | 2.1 | 90.1 | 103.5 | 104.6 | vii | 707 | 5.4 |
| 9 | 2.3 | 93.0 | 106.8 | 107.9 | viii | 685 | 6.2 |
| 10 | 1.9 | 59.6 | 69.1 | 68.4 | ix | 810 | 20.2 |

The average release per 0.01 g of complex for all five batches was 764 μL/L. Normalizing for the different amount of 1-MCP in each batch by multiplying by 764/c gives the results in TABLE 22.

TABLE 22

1-MCP release from petrolatum treated laminate samples, normalized for complex batch variability

| Treated laminate | Amount of 1-MCP released after t hours normalized for complex batch variability (μL/L) | | | | Mean particle size of complex (microns) |
|---|---|---|---|---|---|
| | t = 2 hours | t = 22 hours | t = 44 hours | t = 72 hours | |
| 6 | 2.9 | 106.9 | 124.1 | 122.8 | 6.8 |
| 7 | 0.5 | 16.2 | 18.8 | 18.6 | 44.9 |
| 8 | 2.3 | 97.4 | 111.8 | 113.0 | 5.4 |
| 9 | 2.6 | 103.7 | 119.1 | 120.3 | 6.2 |
| 10 | 1.8 | 56.2 | 65.2 | 64.5 | 20.2 |

At any given time after exposure to water, the normalized release of 1-MCP from the treated laminate samples made from cyclodextrin/l-MCP complex having mean particle size of about 5-7 microns is greater than the normalized release from those treated laminate samples made from complex of mean particle size of about 20 microns, which in turn is greater than the normalized release from those treated laminate samples made from complex of mean particle size of about 45 microns.

Example 14

A 20 mL bottle is charged with 9.8 g of UV Coating VP 10169/60 MF-2NE (obtained from Verga GmbH of Aschau am Inn, Germany) and 0.2 g of an alpha-cyclodextrin/1-MCP complex. The 20 mL bottle is firmly capped and the components are mixed by shaking the bottle by hand until uniformly dispersed, resulting in a UV-curable blend comprising 2 wt % of the alpha-cyclodextrin/1-MCP complex.

A portion of the mixture is removed from the bottle with a dropper and dispensed on a glass pan. A rubber ink roller is used to spread the mixture on the glass and roller. Next, the roller is used to coat the mixture on the coated side of a 20 cm by 20 cm section of polyethylene extrusion coated paper (REYNOLDS® Freezer Paper, 90 microns total thickness). A razor blade is used to cut a 5 cm by 10 cm rectangle from the coated portion of the sheet. Then the coated cut rectangle is passed by hand about 10 cm beneath a medium pressure mercury arc lamp operating at 200 watts per inch (79 watts per cm). After 1.5 seconds exposure to the lamp, the cured rectangle is removed. The cured rectangle is allowed to sit on a laboratory bench overnight coating side down. Six replicate coated rectangles of each formulation are made in this fashion.

The above procedure is carried out for each of the five batches of HAIP described in Examples 7 and 8; Batch v, Batch vi, Batch vii, Batch viii, and Batch ix. Accordingly, 30 rectangles, six made from each batch of complex, are made.

Each rectangle is placed in a 250 mL serum bottle. Then the 30 bottles are sealed with TEFLON® faced silicone septa. The 1-MCP headspace concentration in each serum bottle is quantified using gas chromatography by removing 250 μL of gas from the serum bottle using a six port, two-position gas sampling valve interfaced directly to the GC column having FID detector. No measurable concentration of 1-MCP is detected in the headspace of any of the serum bottles.

Then 50 μL of deionized water is injected into each bottle. Care is taken so that the liquid water does not directly contact the coated rectangle. The headspace of each of the 30 sealed serum bottles is analyzed at 1, 2, 4, 8, 24, and 96 hours after the injection of water, wherein about 3 mL of the 250 mL bottle headspace volume is removed for each analysis. In each sampling, the amount of 1-MCP released from the UV coated rectangles is quantified by gas chromatography against a 6-point 1-butene calibration curve having a 0.998 correlation coefficient. TABLE 23 illustrates the average of six replicate samples of 1-MCP headspace concentration for each Batch.

TABLE 23

1-MCP release from UV-cured coatings

| | t (hours) | Batch v | Batch vi | Batch vii | Batch viii | Batch ix |
|---|---|---|---|---|---|---|
| 1-MCP released (μL/L) after time t | t = 1 hour | 7.4 | 1.5 | 5.5 | 5.5 | 4.8 |
| | t = 2 hours | 18.2 | 3.1 | 12.5 | 13.4 | 10.9 |
| | t = 4 hours | 33.4 | 5.0 | 23.9 | 24.6 | 18.5 |
| | t = 8 hours | 47.8 | 6.2 | 36.2 | 36.9 | 24.6 |
| | t = 24 hours | 54.6 | 7.8 | 42.3 | 43.6 | 28.0 |
| | t = 96 hours | 56.0 | 8.0 | 43.4 | 44.7 | 28.7 |
| Mean release, c, per 0.01 g of complex (μL/L) | | 832 | 787 | 707 | 685 | 810 |
| Mean particle size of complex (microns) | | 6.8 | 44.9 | 5.4 | 6.2 | 20.2 |

The average release per 0.01 g of complex for all five batches was 764 μL/L. Normalizing for the different release from the different batches by multiplying by 764/c gives the results in TABLE 24.

TABLE 24

1-MCP release from UV-cured coatings, normalized for complex batch variability

| t (hours) | | Batch v | Batch vi | Batch vii | Batch viii | Batch ix |
|---|---|---|---|---|---|---|
| 1-MCP released (μL/L) after time t | t = 1 hour | 6.8 | 1.5 | 6.0 | 6.1 | 4.5 |
| | t = 2 hours | 16.7 | 3.0 | 13.5 | 14.9 | 10.2 |
| | t = 4 hours | 30.7 | 4.9 | 25.8 | 27.4 | 17.4 |
| | t = 8 hours | 43.9 | 6.0 | 39.1 | 41.1 | 23.2 |
| | t = 24 hours | 50.1 | 7.6 | 45.7 | 48.6 | 26.4 |
| | t = 96 hours | 51.3 | 7.8 | 46.8 | 49.8 | 27.0 |
| Mean particle size of complex (microns) | | 6.8 | 44.9 | 5.4 | 6.2 | 20.2 |

At any given time after exposure to water, the normalized release of 1-MCP from coatings made from cyclodextrin/1-MCP complex having mean particle size of about 5-7 microns is greater than the normalized release from those coatings made from complex of mean particle size of about 20 microns, which in turn is greater than the normalized release from those coatings made from complex of mean particle size of about 45 microns.

Example 15

A new electrostatic printing toner cartridge (Brother TN-225Y replacement yellow toner cartridge, obtained from Brother International Corp. of Bridgewater, N.J.) is emptied by cutting a 17 mm filling hole using a tool that melts a ring into the toner cartridge and collecting the free-flowing toner in a tared 6 oz. HDPE plastic bottle. After emptying the cartridge, the hole is resealed. Then 25 grams of X-Generation® yellow toner no. 18532 (yellow replacement toner obtained from 123Toner.com) is added to a 6.5 oz. polyester beaker, then 2.8 wt % of HAIP alpha-cyclodextrin/1-MCP complex is added to the yellow toner material slowly while mixing. This mixture is mixed for one hour using the technique described in U.S. Pat. No. 6,599,673 using a mixing blade similar to FIG. 5 in that patent. Following the mixing/blending process, the toner is returned to the cartridge via the aforementioned hole. After refilling the cartridge, it is gently shaken side to side to distribute the toner mixture.

The refilled cartridge is mounted in a Brother MFC-9340 CDW laser multi-function color copier (obtained from the Brother International Corp. of Bridgewater, N.J.) according to the manufacturer's directions. The copier thus refitted is referred to as the modified copier.

A solid yellow continuous rectangle image having a total printable area of 20 cm×26.4 cm and having a maximum yellow density is designed on a computer using MICROSOFT® Excel software. The image is then printed onto standard photocopier paper using a HP Laser Jet 5550dn (obtained from the Hewlett-Packard Company of Palo Alto, Calif.). This is referred to as 100% printed paper.

A second image consisting of a maximum yellow density diamond pattern having overall dimensions of 20 cm×26.4 cm but representing 50% of total yellow area of the image of the 100% image is designed on a computer using MICROSOFT® Excel software. The image is then printed onto standard photocopier paper using a HP Laser Jet 5550dn (obtained from the Hewlett-Packard Company of Palo Alto, Calif.). This is referred to as a 50% printed paper.

The 100% printed paper is placed onto the Brother MFC-9340 CDW copier image scanner glass. The modified printer settings were set to print to "plain paper", print emulation of "HP LaserJet", and a paper setting of "thin paper".

The modified copier is loaded with plain white copy paper (Boise copier paper, 20 lb.), and then six paper sheets are printed with the scanned image and discarded. Then two additional sheets are printed and kept for testing. Then the printer is loaded with polyester film (8.5"×11"×110 μm thick, obtained from the ACCO Brands of Zurich, Ill.) and two film sheets are printed and kept for testing. Fuser temperature measurements are acquired during printing, and are shown in TABLE 25.

A paper cutter is used to cut two replicate 7.6 cm by 20.3 cm rectangles from each of the two paper sheets and each of the two transparency film sheets. The samples are individually placed in 250 mL glass serum bottles. Then 200 μL of deionized water is injected into each bottle. Care is taken so that the liquid water does not directly contact the sample sheets. The bottles are then sealed with TEFLON® faced silicone rubber septa. Then 1-MCP is measured in the headspace at about 1, 2, 4, 8, 24 and 96 hours after the injection of water into the bottle by removing 250 μL of headspace gas using a six port, two-position gas sampling valve (Valco #EC6W, obtained from Valco Instruments Inc. of Houston, Tex.) interfaced directly to a gas chromatograph (GC; Hewlett Packard 5890, obtained from the Hewlett Packard Company of Palo Alto, Calif.) using a RTx-5 GC column, 30 m×0.25 mm I.D., 0.25 μm film (obtained from Restek, Inc., of Bellefonte, Pa.) equipped with a flame ionization detector (FID) and quantitated against a 6-point 1-butene (99.0% pure, Scott Specialty Gases, Plumsteadville, Pa.; also known as Air Liquide America Specialty Gases LLC) calibration curve.

Next, the 50% printed paper was placed onto the Brother MFC-9340 CDW copier image scanner glass and the scanning, printing, cutting, and headspace analysis procedures employed for the 100% image were repeated using the 50% image.

The above procedure is carried out for each of the HAIP Batches v, vi, vii, viii, and ix (described in Examples 7 and 8).

The average 1-MCP release of the two paper replicates at 100% area printing and at 50% area printing at one hour, two hours, four hours, eight hours, and 24 hours results for each of the complex batches is reported in TABLE 25.

TABLE 25

Release of 1-MCP from the printed paper samples of Example 15

| Fuser Temp (° C.) | % Print Coverage | 1 Hr μL/L | 2 Hrs μL/L | 4 Hrs μL/L | 8 Hrs μL/L | 24 Hrs μL/L | Batch of complex |
|---|---|---|---|---|---|---|---|
| 170 | 100 | 0.64 | 1.15 | 1.98 | 3.46 | 10.78 | v |
| | | 0.13 | 0.20 | 0.30 | 0.50 | 1.55 | vi |
| | | 0.48 | 0.79 | 1.42 | 2.58 | 8.34 | vii |
| | | 0.46 | 0.82 | 1.42 | 2.57 | 8.37 | viii |
| | | 0.41 | 0.69 | 1.09 | 1.84 | 5.52 | ix |
| 165 | 50 | 0.25 | 0.42 | 0.82 | 1.34 | 2.37 | v |
| | | 0.05 | 0.07 | 0.12 | 0.20 | 0.34 | vi |
| | | 0.18 | 0.29 | 0.59 | 1.00 | 1.84 | vii |
| | | 0.18 | 0.31 | 0.6 | 1.03 | 1.89 | viii |
| | | 0.16 | 0.26 | 0.45 | 0.71 | 1.21 | ix |

The average release per 0.01 g of complex for all five batches was 764 μL/L. Normalizing for the different release from the different batches by multiplying by 764/c gives the results in TABLE 26.

TABLE 26

Normalized release of 1-MCP from the printed paper samples of Example 15

| Fuser Temp (° C.) | % Print Coverage | 1 Hr μL/L | 2 Hrs μL/L | 4 Hrs μL/L | 8 Hrs μL/L | 24 Hrs μL/L | Batch of complex |
|---|---|---|---|---|---|---|---|
| 170 | 100 | 0.59 | 1.06 | 1.82 | 3.18 | 9.90 | v |
|  |  | 0.13 | 0.19 | 0.29 | 0.49 | 1.50 | vi |
|  |  | 0.52 | 0.85 | 1.53 | 2.79 | 9.01 | vii |
|  |  | 0.51 | 0.91 | 1.58 | 2.87 | 9.34 | viii |
|  |  | 0.38 | 0.65 | 1.03 | 1.74 | 5.21 | ix |
| 165 | 50 | 0.23 | 0.39 | 0.75 | 1.23 | 2.18 | v |
|  |  | 0.05 | 0.07 | 0.12 | 0.19 | 0.33 | vi |
|  |  | 0.19 | 0.31 | 0.64 | 1.08 | 1.99 | vii |
|  |  | 0.20 | 0.35 | 0.67 | 1.15 | 2.11 | viii |
|  |  | 0.15 | 0.24 | 0.42 | 0.67 | 1.14 | ix |

At any given time after exposure to water, the normalized release of 1-MCP from prints made from cyclodextrin/1-MCP complex having mean particle size of about 5-7 microns is greater than the normalized release from those prints made from complex of mean particle size of about 20 microns, which in turn is greater than the normalized release from those prints made from complex of mean particle size of about 45 microns. This is the case for both 100% printed area and for 50% printed area on paper.

The average 1-MCP release of the two film replicates at 100% area printing and at 50% area printing at one hour, two hours, four hours, eight hours, and 24 hours results for each of the complex batches is reported in TABLE 27.

TABLE 27

Release of 1-MCP from the printed film samples of Example 15

| Fuser Temp (° C.) | % Print Coverage | 1 Hr μL/L | 2 Hrs μL/L | 4 Hrs μL/L | 8 Hrs μL/L | 24 Hrs μL/L | Batch of complex |
|---|---|---|---|---|---|---|---|
| 175 | 100 | 1.28 | 4.18 | 5.73 | 9.88 | 14.37 | v |
|  |  | 0.27 | 0.71 | 0.86 | 1.44 | 2.06 | vi |
|  |  | 0.96 | 2.87 | 4.10 | 7.37 | 11.12 | vii |
|  |  | 0.96 | 3.07 | 4.22 | 7.56 | 11.48 | viii |
|  |  | 0.83 | 2.52 | 3.17 | 5.25 | 7.36 | ix |
| 165 | 50 | 0.44 | 1.33 | 2.86 | 4.52 | 6.04 | v |
|  |  | 0.09 | 0.23 | 0.43 | 0.66 | 0.87 | vi |
|  |  | 0.33 | 0.92 | 2.05 | 3.37 | 4.67 | vii |
|  |  | 0.37 | 0.98 | 2.11 | 3.45 | 4.82 | viii |
|  |  | 0.29 | 0.80 | 1.62 | 2.42 | 3.09 | ix |

The average release per 0.01 g of complex for all five batches was 764 μL/L. Normalizing for the different release from the different batches by multiplying by 764/c gives the results in TABLE 28.

TABLE 28

Normalized release of 1-MCP from the printed film samples of Example 15

| Fuser Temp (° C.) | % Print Coverage | 1 Hr μL/L | 2 Hrs μL/L | 4 Hrs μL/L | 8 Hrs μL/L | 24 Hrs μL/L | Batch of complex | Mean particle size of complex (microns) |
|---|---|---|---|---|---|---|---|---|
| 175 | 100 | 1.18 | 3.84 | 5.26 | 9.07 | 13.20 | v | 6.8 |
|  |  | 0.26 | 0.69 | 0.83 | 1.40 | 2.00 | vi | 44.9 |
|  |  | 1.04 | 3.10 | 4.43 | 7.96 | 12.02 | vii | 5.4 |
|  |  | 1.07 | 3.42 | 4.71 | 8.43 | 12.80 | viii | 6.2 |
|  |  | 0.78 | 2.38 | 2.99 | 4.95 | 6.94 | ix | 20.2 |
| 165 | 50 | 0.40 | 1.22 | 2.63 | 4.15 | 5.55 | v | 6.8 |
|  |  | 0.09 | 0.22 | 0.42 | 0.64 | 0.84 | vi | 44.9 |
|  |  | 0.36 | 0.99 | 2.22 | 3.64 | 5.05 | vii | 5.4 |
|  |  | 0.41 | 1.09 | 2.35 | 3.85 | 5.38 | viii | 6.2 |
|  |  | 0.27 | 0.75 | 1.53 | 2.28 | 2.91 | ix | 20.2 |

At any given time after exposure to water, the normalized release of 1-MCP from prints made from cyclodextrin/1-MCP complex having mean particle size of about 5-7 microns is greater than the normalized release from those prints made from complex of mean particle size of about 20 microns, which in turn is greater than the normalized release from those prints made from complex of mean particle size of about 45 microns. This is the case for both 100% printed area and for 50% printed area on film.

What is claimed is:

1. A particulate composition consisting essentially of a mixture of a first particulate portion and a second particulate portion, wherein
   i) the first particulate portion is a modified portion of a source particulate and has a mean particle size between 1 μm and 10 μm, or between 10 μm and 20 μm as determined by a volume-based method, and the second particulate portion is an unmodified portion of the source particulate and has a mean particle size between 30 μm and 100 μm, as determined by a volume-based method, wherein the source particulate consists essentially of a 1-methylcyclopropene clathrate of α-cyclodextrin;
   ii) the first particulate portion and the second particulate portion have a first rate of 1-methylcyclopropene release and a second rate of 1-methylcyclopropene release, respectively, when subjected to a set of disgorgement conditions; and iii) the particulate composition has a rate of 1-methylcyclopropene release that is intermediate between said first rate of 1-methylcyclopropene release and said second rate of 1-methylcyclopropene release when subjected to said set of disgorgement conditions.

2. The particulate composition of claim 1 wherein the volume-based method is light scattering.

3. The particulate composition of claim 1 wherein the first particulate portion has a mean particle size between 1 μm and 3 μm, between 2 μm and 4 μm, between 3 μm and 5 μm, between 4 μm and 6 μm, between 5 μm and 7 μm, between 6 μm and 8 μm, between 7 μm and 9 μm, between 8 μm and 10 μm, between 10 μm and 12 μm, between 11 μm and 13 μm, between 12 μm and 14 μm, between 13 μm and 15 μm, between 1 μm and 5 μm, between 5 μm and 10 μm, between 10 μm and 15 μm, between 15 μm and 20 μm, between 2 μm and 10 μm, between 3 μm and 10 μm, between 3 μm and 9 μm, between 3 μm and 8 μm, or between 3 μm and 7 μm.

4. The particulate composition of claim 1 wherein the first particulate portion mean particle size is about 4 μm.

5. The particulate composition of claim 1 wherein the first particulate portion mean particle size is about 5 μm.

6. The particulate composition of claim 1 wherein the first particulate portion mean particle size is about 6 μm.

7. The particulate composition of claim 1 wherein the first particulate portion mean particle size is about 7 μm.

8. The particulate composition of claim 1 wherein the second particulate portion has a mean particle size between 40 μm and 70 μm.

9. The particulate composition of claim 1 wherein the particulate composition comprises about 1 to 1000 parts by weight of the first particulate portion and about 1 to 1000 parts by weight of the second particulate portion.

10. The particulate composition of claim 1 wherein the mixture has a bimodal mean particle size distribution.

11. The particulate composition of claim 1 wherein the disgorgement conditions are a pressure of about 1 atm, a temperature between 0° C. and about 50° C., and a relative humidity between about 80% and 100%.

12. The particulate composition of claim 1, wherein a portion of the source particulate is comminuted to produce the first particulate portion.

13. The particulate composition of claim 1, wherein a portion of the source particulate is classified to produce the first particulate portion.

14. A method of disgorging 1-methylcyclopropene gas from the particulate composition according to claim 1, the method comprising
a. obtaining the particulate composition comprising the mixture of the first particulate portion and the second particulate portion; and
b. situating the particulate composition proximal to a living plant or portion thereof.

15. A method of making the particulate composition according to claim 1, the method comprising:
a. obtaining a source particulate consisting essentially of a 1-methylcyclopropene clathrate of α-cyclodextrin, the source particulate having a mean particle size between 30 μm and 100 μm as determined by a volume-based method;
b. modifying a first portion of the source particulate to provide a first particulate portion having a mean particle size between 1 μm and 10 μm, or between 10 μm and 20 μm as determined by the volume-based method; and
c. admixing at least a portion of the first particulate portion with at least a portion of the source particulate to obtain the particulate composition.

* * * * *